(12) United States Patent  
Overbeek et al.

(10) Patent No.: US 12,180,194 B2
(45) Date of Patent: *Dec. 31, 2024

(54) MULTI-AZIRIDINE COMPOUND

(71) Applicant: Covestro (Netherlands) B.V., Geleen (NL)

(72) Inventors: Gerardus Cornelis Overbeek, Echt (NL); Patrick Johannes Maria Stals, Echt (NL); Daan Van Der Zwaag, Echt (NL); Alfred Jean Paul Bückmann, Echt (NL)

(73) Assignee: Covestro (Netherlands) B.V., Geleen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/526,220

(22) Filed: Dec. 1, 2023

(65) Prior Publication Data
US 2024/0166634 A1 May 23, 2024

Related U.S. Application Data

(63) Continuation of application No. 17/261,282, filed as application No. PCT/EP2019/069198 on Jul. 17, 2019, now Pat. No. 11,878,969.

(30) Foreign Application Priority Data

Jul. 23, 2018 (EP) ..................... 18184969

(51) Int. Cl.
| C07D 403/14 | (2006.01) |
| C08K 5/3432 | (2006.01) |
| C09D 7/40 | (2018.01) |
| C09D 133/08 | (2006.01) |
| C09D 133/12 | (2006.01) |
| C09D 167/02 | (2006.01) |
| C09D 175/04 | (2006.01) |

(52) U.S. Cl.
CPC .......... *C07D 403/14* (2013.01); *C08K 5/3432* (2013.01); *C09D 7/40* (2018.01); *C09D 133/08* (2013.01); *C09D 133/12* (2013.01); *C09D 167/02* (2013.01); *C09D 175/04* (2013.01)

(58) Field of Classification Search
CPC ...... C07D 403/14; C09D 7/40; C09D 133/08; C09D 133/12; C09D 167/02; C09D 175/04; C08K 5/3432
See application file for complete search history.

(56) References Cited

U.S. PATENT DOCUMENTS

| 3,329,674 A | 7/1967 | Bulbenko et al. |
| 3,337,533 A | 8/1967 | Ham |
| 3,523,750 A | 8/1970 | Tesoro |
| 3,560,415 A | 2/1971 | Grogler et al. |
| 3,583,977 A | 6/1971 | Uelzmann |
| 3,763,132 A | 10/1973 | Meiser, Jr. |
| 3,933,936 A | 1/1976 | Smith et al. |
| 5,106,993 A | 4/1992 | Kania |
| 5,164,467 A | 11/1992 | Kania |
| 5,241,001 A | 8/1993 | Kania et al. |
| 5,258,481 A | 11/1993 | Hesselmans et al. |
| 5,359,005 A | 10/1994 | Kania et al. |
| 5,741,543 A | 4/1998 | Winslow et al. |
| 9,328,065 B2 | 5/2016 | Bottcher et al. |
| 2007/0298006 A1 | 12/2007 | Tomalia et al. |
| 2015/0118501 A1 | 4/2015 | Lu et al. |

FOREIGN PATENT DOCUMENTS

| CN | 108084870 A | 5/2018 |
| EP | 0507407 B1 | 6/1996 |
| EP | 0758662 A2 | 2/1997 |
| EP | 1865014 A1 | 12/2007 |
| EP | 2279230 B1 | 1/2012 |
| EP | 2516391 B1 | 3/2015 |
| GB | 1344725 A | 1/1974 |
| JP | S4727971 Y1 | 8/1972 |

(Continued)

OTHER PUBLICATIONS

International Search Report for PCT/EP2019/069198 dated Sep. 18, 2019, 3 pages.

(Continued)

*Primary Examiner* — Timothy R Rozof
(74) *Attorney, Agent, or Firm* — The Webb Law Firm

(57) ABSTRACT

The present invention relates to a multi-aziridine compound having:

a) from 2 to 6 of the following structural units (A):

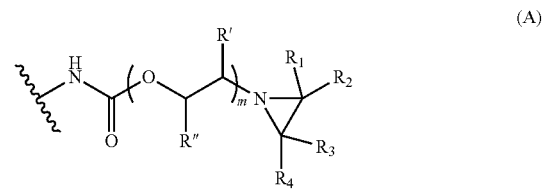

(A)

whereby

R', R", $R_1$, $R_2$, $R_3$ and $R_4$ are as defined herein m is an integer from 1 to 6;

b) one or more linking chains wherein each one of these linking chains links two of the structural units A; and c) a molecular weight in the range from 600 Daltons to 5000 Daltons.

The multi-aziridine compound can be used for example for crosslinking of for example carboxylic acid functional polymers dissolved and/or dispersed in an aqueous medium.

50 Claims, 15 Drawing Sheets

(56) References Cited

FOREIGN PATENT DOCUMENTS

| | | |
|---|---|---|
| JP | S51141860 A | 12/1976 |
| JP | S59128291 A | 7/1984 |
| JP | H11500152 A | 1/1999 |
| JP | 2012529473 A | 11/2012 |
| JP | 2015505889 A | 2/2015 |
| WO | 2006115547 A2 | 11/2006 |
| WO | 2013089927 A1 | 6/2013 |
| WO | 2015066868 A1 | 5/2015 |
| WO | 2020020714 A1 | 1/2020 |

OTHER PUBLICATIONS

Written Opinion of the ISA for PCT/EP2019/069198 dated Sep. 18, 2019, 5 pages.

MULTI-AZIRIDINE COMPOUND

CROSS-REFERENCE TO RELATED APPLICATIONS

This application is a continuation of U.S. application Ser. No. 17/261,282, filed on Jul. 17, 2019, which is the U.S. national phase of International Application No. PCT/EP2019/069198, filed Jul. 17, 2019, which designated the U.S. and claims priority to EP Patent Application No. 18184969.6, filed Jul. 23, 2018, the entire contents of each of which are hereby incorporated by reference.

FIELD

The present invention relates to compounds with at least two aziridinyl groups which can be used for example for crosslinking of for example carboxylic acid functional polymers dissolved and/or dispersed in an aqueous medium.

Over the years, the need for coatings with improved resistances, like stain and solvent resistance, improved mechanical properties and improved adhesive strength is more and more growing. One or more of those properties can be elevated to a higher level by means of crosslinking. Many crosslink mechanisms have been studied over the years and for waterborne dispersions, the most useful ones include isocyanate crosslinking of hydroxyl functional dispersions, the reaction between carbodiimide and carboxylic acid, epoxy crosslinking and crosslinking using aziridine based crosslinkers.

U.S. Pat. No. 5,133,997 describes coating compositions comprising an aqueous dispersion of linear aliphatic urethane resins, an anionic surfactant and a crosslinking agent capable of facilitating the cure of said resin. Trimethylolpropane tris(2-methyl-1-aziridinepropionate), CAS number 64265-57-2, a polyfunctional aziridine crosslinker, is used as crosslinking agent, which is a well-known and very active for crosslinking carboxylic acid functional polymers. This crosslinker however has an unfavourable genotoxic profile. There is a need in the industry to improve the safety, health and environmental profile of adhesives, inks and coatings and also of the substances used for preparing adhesives, inks and coatings. Genotoxicity describes the property of chemical or physical agents that cause any type of DNA damage, which may not always lead to a transmittable mutation. Mutagenicity refers to the induction of permanent transmissible DNA changes (as DNA composition or chromosome structure), which are retained in somatic cell division and passed onto progeny in germ cells. Genotoxicity must not be confused with mutagenicity. All mutagens are genotoxic whereas not all genotoxic substances are mutagenic.

The object of the present invention is to provide a compound with at least two aziridinyl groups which has reduced genotoxicity compared to trimethylolpropane tris (2-methyl-1-aziridinepropionate). Compounds with at least two aziridinyl groups are further referred herein as multi-aziridine compounds.

This object has surprisingly been achieved by providing a multi-aziridine compound having:
a) from 2 to 6 of the following structural units (A):

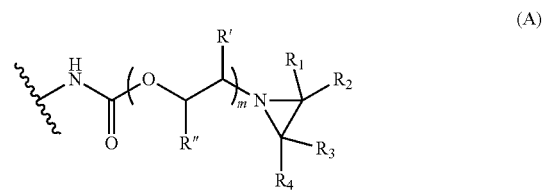

(A)

whereby
$R_1$ is H;
$R_2$ and $R_4$ are independently chosen from H, a linear group containing from 1 to 8 carbon atoms and optionally containing one or more heteroatoms in the chain, a branched or cyclic group containing from 3 to 8 carbon atoms and optionally containing one or more heteroatoms in the chain, phenyl, benzyl, or pyridinyl;
$R_3$ is a linear group containing from 1 to 8 carbon atoms and optionally containing one or more heteroatoms in the chain, a branched or cyclic group containing from 3 to 8 carbon atoms and optionally containing one or more heteroatoms in the chain, phenyl, benzyl, or pyridinyl;
whereby $R_2$ and $R_3$ (in case $R_2$ is different than H) may be part of the same cyclic group containing from 3 to 8 carbon atoms;
R'=H or an aliphatic hydrocarbon group containing from 1 to 12 carbon atoms;
R"=H, an aliphatic hydrocarbon group containing from 1 to 12 carbon atoms, a cycloaliphatic hydrocarbon group containing from 5 to 12 carbon atoms, an aromatic hydrocarbon group containing from 6 to 12 carbon atoms, $CH_2$—O—(C=O)—R''', $CH_2$—O—R'''', or $CH_2$—(OCR''''HCR''''H)—OR''''', whereby R''' is an aliphatic hydrocarbon group containing from 1 to 12 carbon atoms and R'''' is an aliphatic hydrocarbon group containing from 1 to 12 carbon atoms or an aromatic hydrocarbon group containing from 6 to 12 carbon atoms, n being from 1 to 35, R'''' independently being H or an aliphatic hydrocarbon group containing from 1 to 12 carbon atoms and R''''' being an aliphatic hydrocarbon group containing from 1 to 4 carbon atoms;
whereby R' and R" may be part of the same saturated cycloaliphatic hydrocarbon group containing from 5 to 8 carbon atoms;
m is an integer from 1 to 6;
b) one or more linking chains wherein each one of these linking chains links two of the structural units A present in the multi-aziridine compound; and
c) a molecular weight in the range of from 600 Daltons to 5000 Daltons.

DETAILED DESCRIPTION

Figure 1:
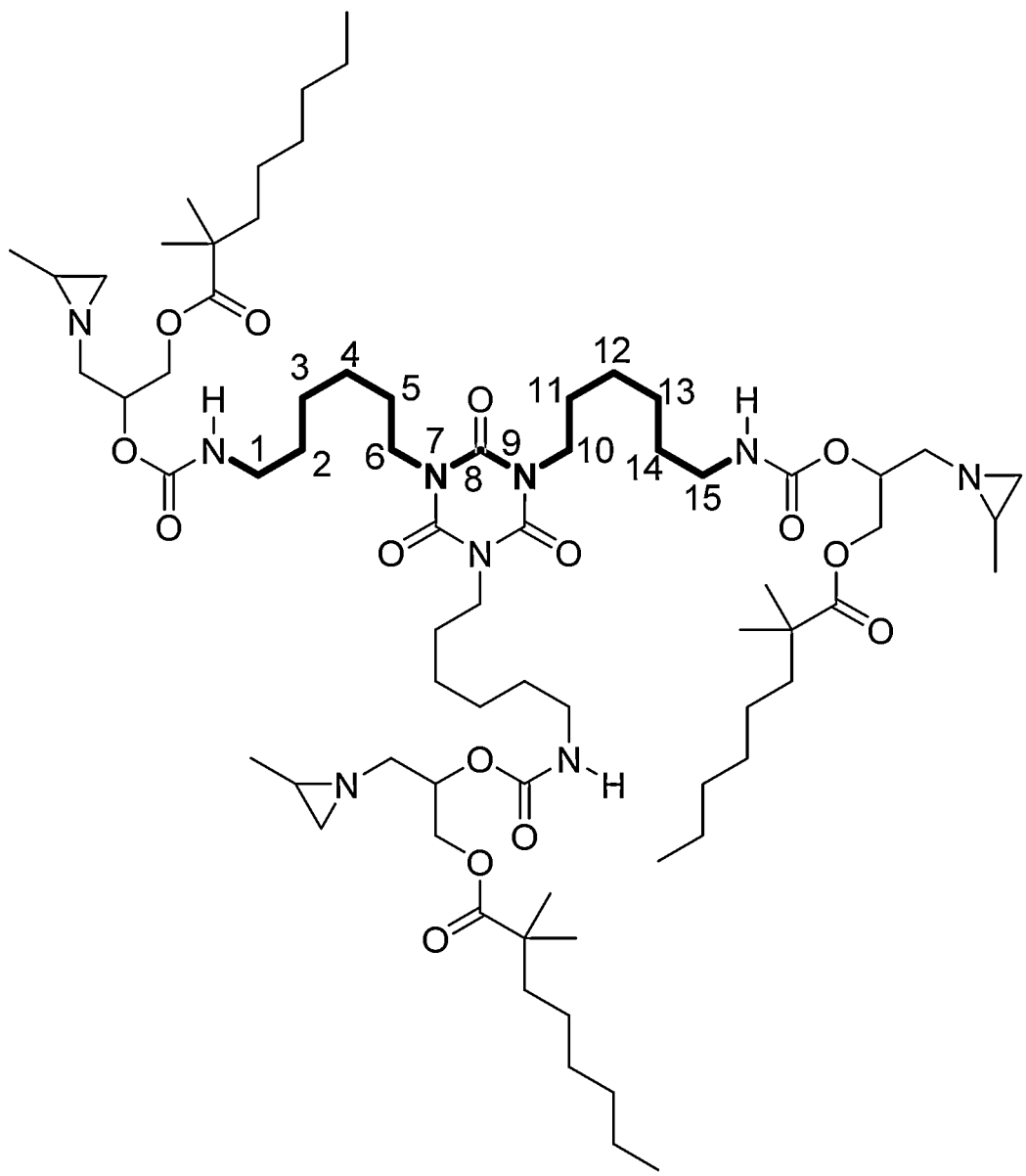
FIGS. 1-10 show non-limiting examples of chemical structures of multi-aziridine compounds according to the present disclosure.

It has surprisingly been found that the multi-aziridine compounds according to the invention have reduced genotoxicity compared to trimethylolpropane tris(2-methyl-1-aziridinepropionate). The multi-aziridine compounds according to the invention show either only weakly positive induced genotoxicity or even they do not show genotoxicity, i.e. they show a genotoxicity level comparable with the naturally occurring background.

The genotoxicity can be measured by the ToxTracker® assay (Toxys, Leiden, the Netherlands) as further described herein. The ToxTracker® assay can be applied for pure substances or for compositions which are the direct products obtained in the preparation of the multi-aziridine compounds of the invention. With positive induced genotoxicity is meant that the induction level of the biomarkers Bscl2-GFP and Rtkn-GFP is equal to or higher than 2-fold at at least one of 10, 25 and 50% cytotoxicity in the absence or presence of the metabolizing system rat S9 liver extract. With weakly positive induced genotoxicity is meant that the induction level of the biomarkers Bsc12-GFP and Rtkn-GFP is higher than 1.5-fold and lower than 2-fold at at least one of 10, 25 and 50% cytotoxicity (but lower than 2-fold at 10, 25 and 50% cytotoxicity) in the absence or presence of rat S9 liver extract-based metabolizing systems (aroclor1254-induced rats, Moltox, Boone, NC, USA). With genotoxicity comparable with the naturally occurring background is meant that the induction level of the biomarkers Bscl2-GFP and Rtkn-GFP is less than or equal to 1.5-fold at 10, 25 and 50% cytotoxicity in the absence and presence of rat S9 liver extract-based metabolizing systems (aroclor1254-induced rats, Moltox, Boone, NC, USA). The induction level of the genotoxicity reporters Bsc12-GFP and Rtkn-GFP is preferably less than or equal to 1.5-fold at 10, 25 and 50% cytotoxicity in the absence and presence of rat S9 liver extract-based metabolizing systems (aroclor1254-induced rats, Moltox, Boone, NC, USA). A substance showing an induction level less than or equal to 1.5-fold at 10, 25 and 50% cytotoxicity in the absence and presence of rat S9 liver extract-based metabolizing systems (aroclor1254-induced rats, Moltox, Boone, NC, USA) is not genotoxic.

For all upper and/or lower boundaries of any range given herein, the boundary value is included in the range given, unless specifically indicated otherwise. Thus, when saying from x to y, means including x and y and also all intermediate values.

The term "coating composition" encompasses, in the present description, paint, coating, varnish, adhesive and ink compositions, without this list being limiting. The term "aliphatic hydrocarbon group" refers to optionally branched alkyl, alkenyl and alkynyl group. The term "cycloaliphatic hydrocarbon group" refers to cycloalkyl and cycloalkenyl group optionally substituted with at least one aliphatic hydrocarbon group. The term "aromatic hydrocarbon group" refers to a benzene ring optionally substituted with at least one aliphatic hydrocarbon group. These optionally substituted aliphatic hydrocarbon groups are preferably alkyl groups. Examples of cycloaliphatic hydrocarbon groups with 7 carbon atoms are cycloheptyl and methyl substituted cyclohexyl. An example of an aromatic hydrocarbon group with 7 carbon atoms is methyl substituted phenyl. Examples of aromatic hydrocarbon groups with 8 carbon atoms are xylyl and ethyl substituted phenyl.

Whilst the structural units (A) present in the multi-aziridine compound according to the invention may independently have different $R_2$, $R_3$, $R_4$, R', R" and/or m, the structural units (A) present in the multi-aziridine compound are preferably identical to each other.

The multi-aziridine compound according to the invention is usually obtained in a composition in which, next to the multi-aziridine compound, remaining starting materials, side-products and/or solvent used for preparing the multi-aziridine compounds may be present. The composition may contain only one multi-aziridine compound according to the invention but may also contain more than one multi-aziridine compound according to the invention. Mixtures of multi-aziridine compounds are for example obtained when a mixture of polyisocyanates as starting material are used.

The urethane aziridine compound according to the invention contains from 2 to 6 of the structural units (A), preferably from 2 to 4 of the structural units (A), more preferably 2 or 3 structural units (A).

$R_2$ and $R_4$ are independently chosen from H, a linear group containing from 1 to 8 carbon atoms which optionally contains one or more heteroatoms (preferably selected from N, S and O) in the chain, a branched or cyclic group containing from 3 to 8 carbon atoms which optionally contains one or more heteroatoms (preferably selected from N, S and O) in the chain, phenyl, benzyl, or pyridinyl. In case $R_2$ is different than H, $R_2$ and $R_3$ may be part of the same cyclic group containing from 3 to 8 carbon atoms, preferably of the same saturated cycloaliphatic hydrocarbon group containing from 3 to 8 carbon atoms. Preferably, $R_2$ and $R_4$ are independently chosen from H, an aliphatic hydrocarbon group containing from 1 to 8 carbon atoms or a cycloaliphatic hydrocarbon group containing from 3 to 8 carbon atoms. More preferably, $R_2$ and $R_4$ are independently chosen from H or an aliphatic hydrocarbon group containing from 1 to 4 carbon atoms. More preferably, $R_2$ and $R_4$ are independently chosen from H or an aliphatic hydrocarbon group containing from 1 to 2 carbon atoms.

$R_3$ is a linear group containing from 1 to 8 carbon atoms and optionally containing one or more heteroatoms (preferably selected from N, S and O) in the chain, a branched or cyclic group containing from 3 to 8 carbon atoms and optionally containing one or more heteroatoms (preferably selected from N, S and O) in the chain, phenyl, benzyl, or pyridinyl. $R_3$ is preferably an aliphatic hydrocarbon group containing from 1 to 8 carbon atoms, a cycloaliphatic hydrocarbon group containing from 3 to 8 carbon atoms, phenyl, benzyl, or pyridinyl. $R_3$ is more preferably an aliphatic hydrocarbon group containing from 1 to 4 carbon atoms.

In a preferred embodiment of the invention, $R_2$ is H, $R_3$ is $C_2H_5$ and $R_4$ is H. In another and more preferred embodiment of the invention, $R_2$ is H, $R_3$ is $CH_3$ and $R_4$ is H or $CH_3$. In another and even more preferred embodiment of the invention, $R_2$ is H, $R_3$ is $CH_3$ and $R_4$ is H.

m is an integer from 1 to 6, preferably m is from 1 to 4, more preferably m is 1 or 2 and most preferably m is 1.

R' is H or an aliphatic hydrocarbon group containing from 1 to 12 carbon atoms, preferably an alkyl group containing from 1 to 12 carbon atoms. R' is preferably H or an alkyl group containing from 1 to 4 carbon atoms. More preferably R' is H or an alkyl group containing from 1 to 2 carbon atoms. Most preferably R' is H.

R" is preferably H, an aliphatic hydrocarbon group containing from 1 to 8 carbon atoms (more preferably from 1 to 4 carbon atoms), a cycloaliphatic hydrocarbon group containing from 5 to 12 carbon atoms, an aromatic hydrocarbon group containing from 6 to 12 carbon atoms, $CH_2$—O—(C=O)—R''', $CH_2$—O—R'''', or $CH_2$—(OCR''''HCR''''H), —OR'''', whereby R''' is an aliphatic hydrocarbon group containing from 1 to 12 carbon atoms and R'''' is an aliphatic hydrocarbon group containing from 1 to 12 carbon atoms or an aromatic hydrocarbon group containing from 6 to 12 carbon atoms, n being from 1 to 35, preferably from 6 to 20, R'''' independently being H or a methyl group and R'''''
being an aliphatic hydrocarbon group containing from 1 to
4 carbon atoms and preferably an alkyl group with 1 to 4
carbon atoms, or R' and R" may be part of the same saturated
cycloaliphatic hydrocarbon group containing from 5 to 8
carbon atoms. More preferably, R"=H, an aliphatic hydrocarbon group containing from 1 to 4 carbon atoms, $CH_2$—
O—(C=O)—R''', $CH_2$—O—R'''', or $CH_2$—
(OCR''''HCR''''H)$_n$—OR''''', whereby R''' is an alkyl group
containing from 1 to 12 carbon atoms and R'''' is an alkyl
group containing from 1 to 12 carbon atoms, n being from
1 to 35, R'''' independently being H or a methyl group and
R''''' being an alkyl group containing from 1 to 4 carbon
atoms;
or R' and R" may be part of the same saturated cycloaliphatic
hydrocarbon group containing from 5 to 8 carbon atoms.

More preferably, R' is H and R"=an alkyl group containing from 1 to 4 carbon atoms, $CH_2$—O—(C=O)—R''',
$CH_2$—O—R'''', or $CH_2$—(OCH$_2$CH$_2$)$_n$—OCH$_3$ whereby
R''' is preferably an alkyl group containing from 3 to 12
carbon atoms, more preferably a branched alkyl group with
from 3 to 12 carbon atoms, such as for example neopentyl
or neodecyl. Most preferably R''' is a branched C9 alkyl. R''''
is preferably an alkyl group containing from 1 to 12 carbon
atoms. Non-limited examples for R'''' are ethyl, butyl and
2-ethylhexyl.

The molecular weight of the multi-aziridine compound
according to the invention is from 600 to 5000 Daltons. The
molecular weight of the multi-aziridine compound according to the invention is preferably at most 3800 Daltons, more
preferably at most 3600 Daltons, more preferably at most
3000 Daltons, more preferably at most 1600 Daltons, even
more preferably at most 1200 Daltons. The molecular
weight of the multi-aziridine compound according to the
invention is preferably at least 700 Daltons, more preferably
at least 800 Daltons, even more preferably at least 840
Daltons and most preferably at least 1000 Daltons. As used
herein, the molecular weight of the multi-aziridine compound is the calculated molecular weight. The calculated
molecular weight is obtained by adding the atomic masses of
all atoms present in the structural formula of the multi-aziridine compound. If the multi-aziridine compound is
present in a composition comprising more than one multi-aziridine compound according to the invention, for example
when one or more of the starting materials to prepare the
multi-aziridine compound is a mixture, the molecular weight
calculation can be performed for each compound individually present in the composition. The molecular weight of the
multi-aziridine compound according to the invention can be
measured using MALDI-TOF mass spectrometry as
described in the experimental part below.

The multi-aziridine compound according to the invention
comprises one or more linking chains wherein each one of
these linking chains links two of the structural units A. The
linking chains present in the multi-aziridine compound
preferably consist of from 2 to 300 atoms, more preferably
from 5 to 250 and most preferably from 6 to 100 atoms. The
atoms of the linking chains are preferably C, N, O, S and/or
P, preferably C, N and/or O.

A linking chain is defined as the shortest chain of consecutive atoms that links two structural units A. FIG. 1
shows, for an example of a multi-aziridine compound
according to the invention, the linking chain between two
structural units A.

Any two of the structural units A present in the multi-aziridine compound of the invention are linked via a linking
chain as defined herein. Accordingly, each structural unit A
present in the multi-aziridine compound of the invention is
linked to every other structural unit A via a linking chain as
defined herein. In case the multi-aziridine compound
according to the invention has two structural units A, the
multi-aziridine compound has one such linking chain linking these two structural units. In case the multi-aziridine
compound according to the invention has three structural
units A, the multi-aziridine compound has three linking
chains, whereby each of the three linking chains is linking
a structural unit A with another structural unit A, i.e. a first
structural unit A is linked with a second structural unit A via
a linking chain and the first and second structural units A are
both independently linked with a third structural unit A via
their respective linking chains.

Figure 2A:
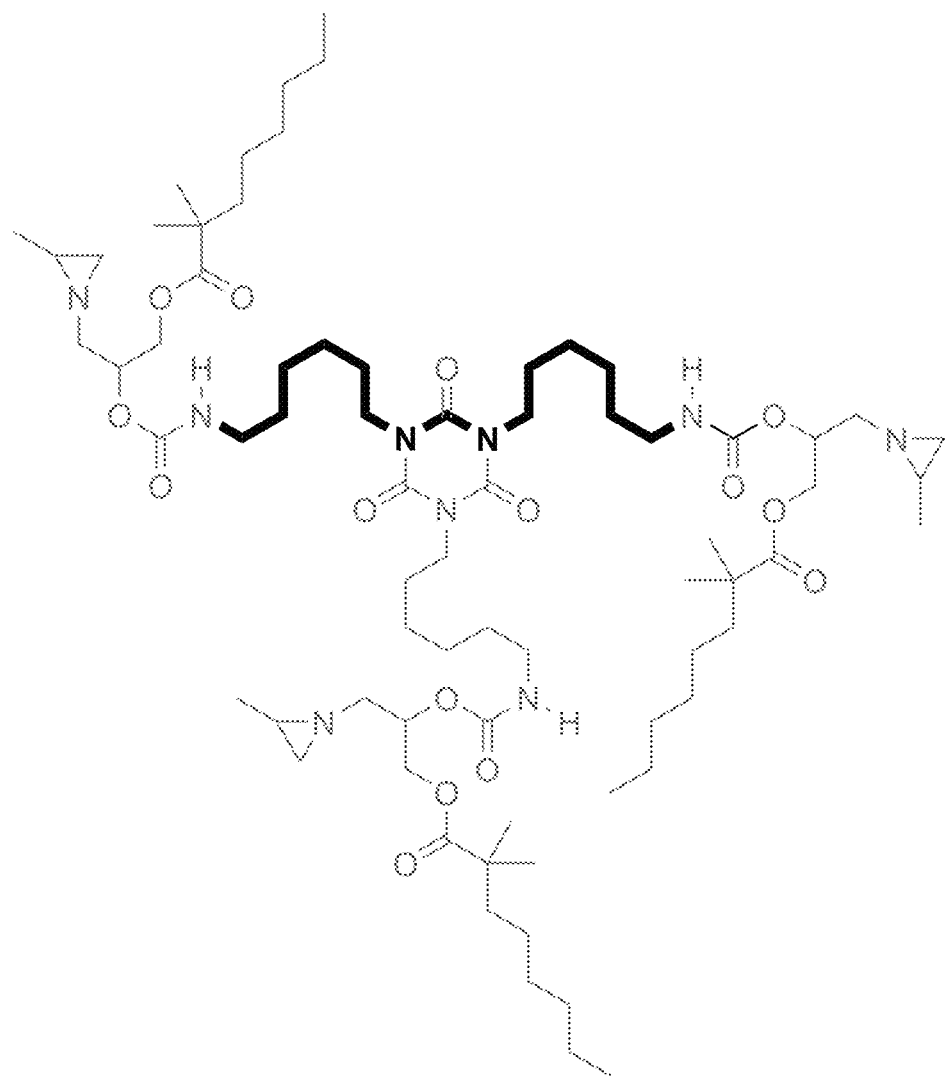
Figure 2B:
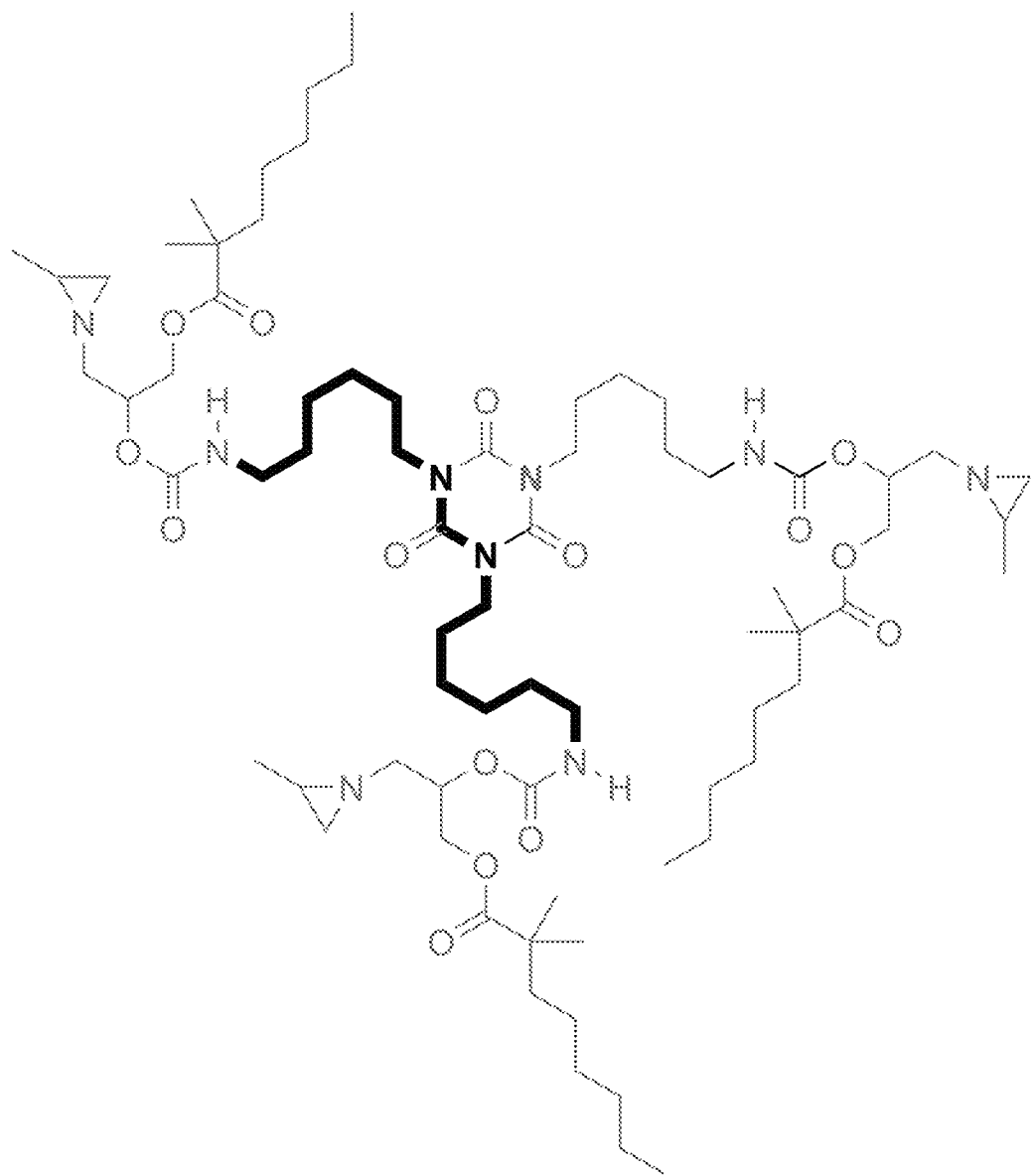
Figure 2C:
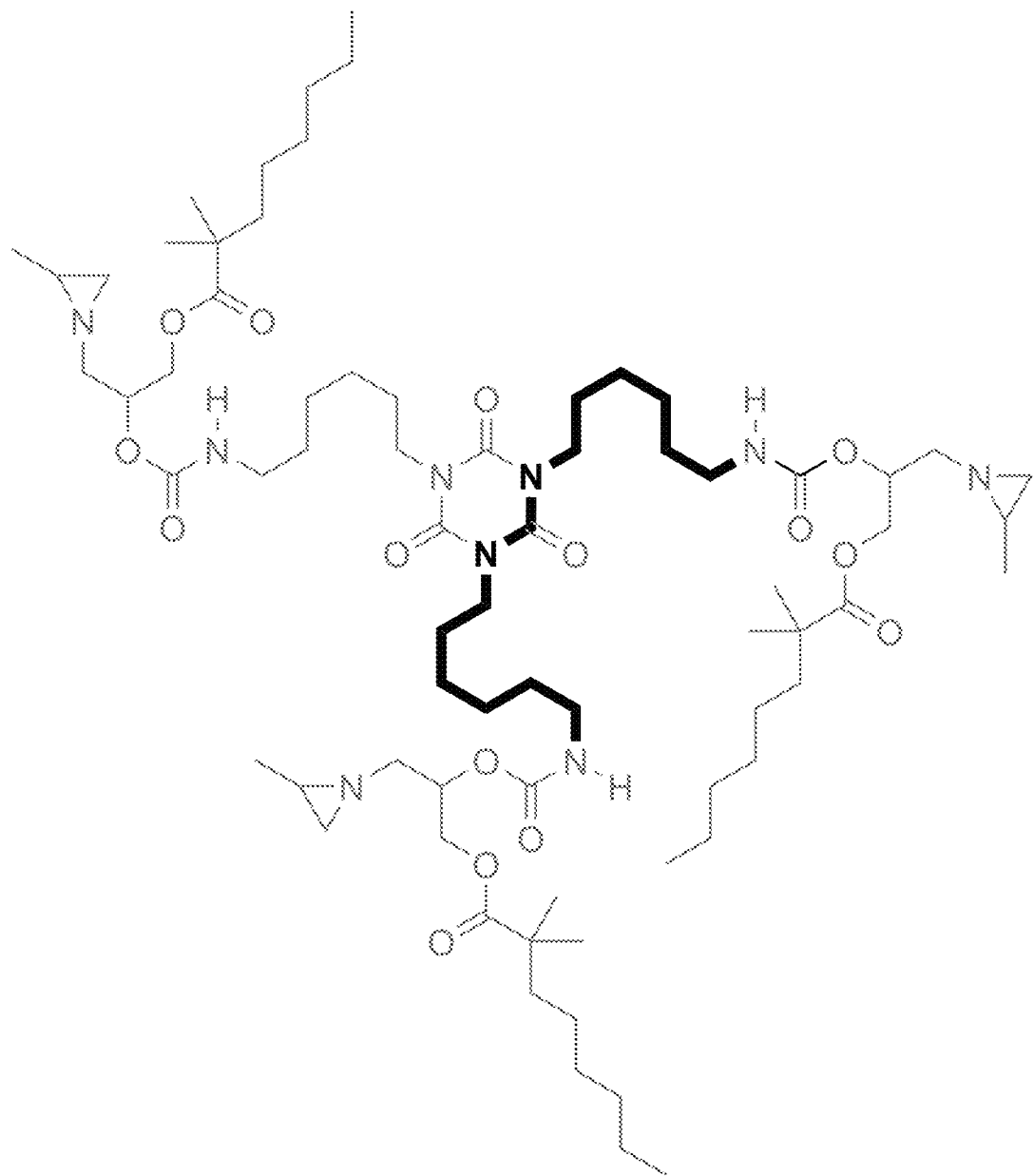

FIGS. 2A-2C show for an example of a multi-aziridine
compound having three structural units A, the three linking
chains whereby each one of the three linking chains links
two structural units A.

Multi-aziridine compounds according to the invention
with more than two structural units A have a number of
linking chains according to the following equation: $LC=\{(AN-1) \times AN\}/2$, whereby LC=the number of linking chains
and AN=the number of structural units A in the multi-aziridine compound. So for example if there are 5 structural
units A in the multi-aziridine compound, AN=5; which
means that there are $\{(5-1) \times 5\}/2=10$ linking chains.

Figure 3A:
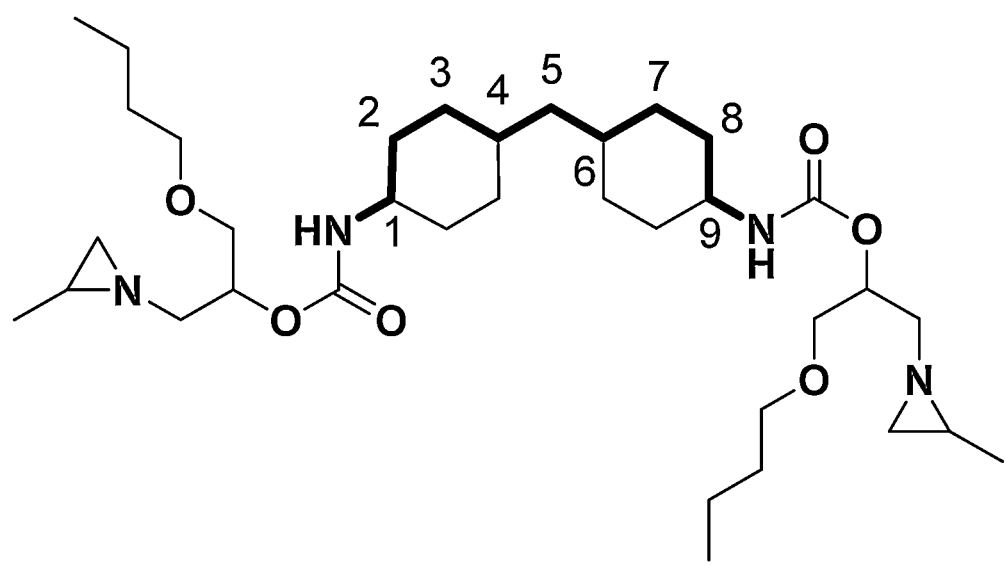
Figure 3B:
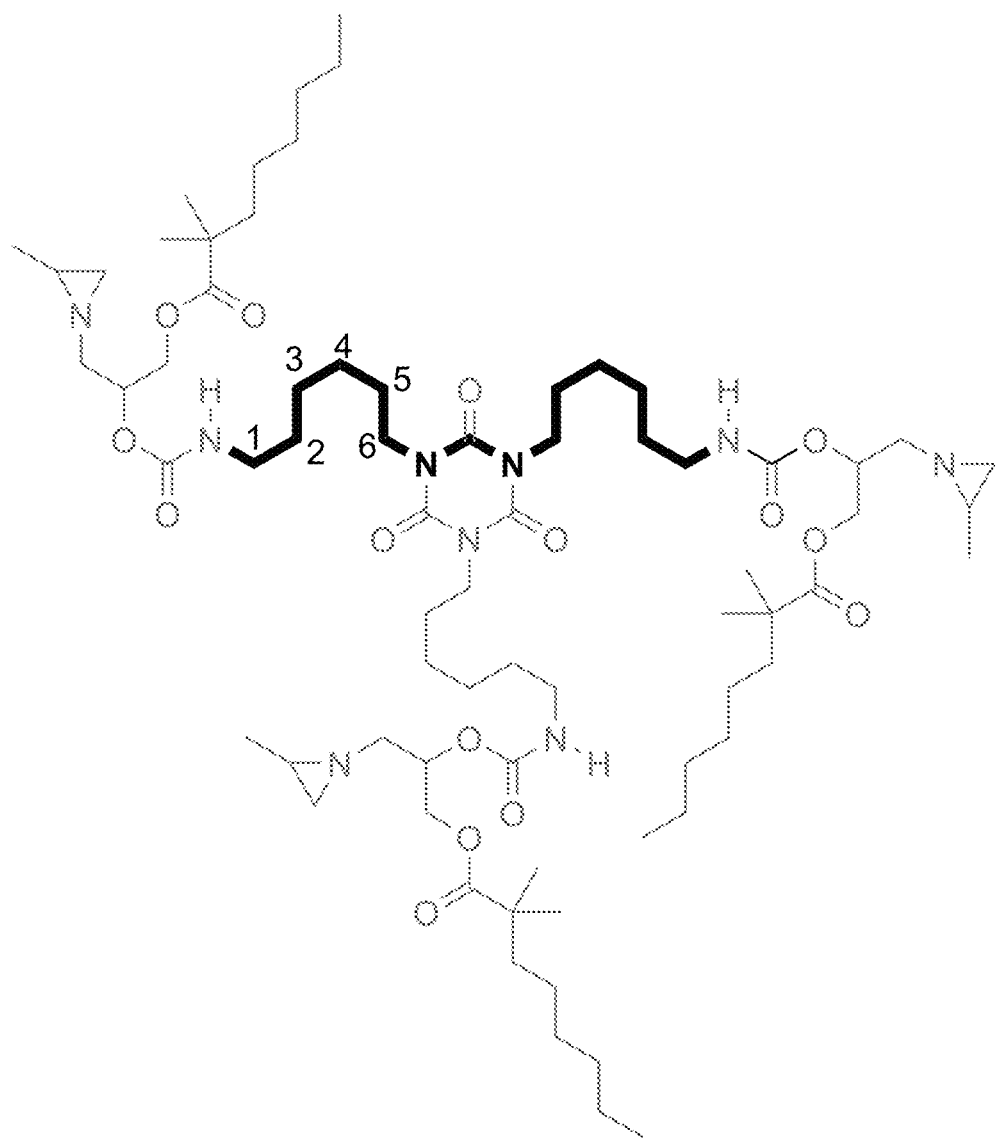

Preferably, the number of consecutive C atoms and
optionally O atoms between the N atom of the urethane
group in a structural unit A and the next N atom which is
either present in the linking chain or which is the N atom of
the urethane group of another structural unit A is at most 9,
as shown in for example FIGS. 3A-3B according to the
invention.

The multi-aziridine compound according to the invention
preferably comprises one or more connecting groups
wherein each one of these connecting groups connects two
of the structural units A, whereby a connecting group is
defined as the array of consecutive functionalities (functionalities as defined herein) connecting two structural units A.
In the present invention, the connecting groups preferably
consist of at least one functionality selected from the group
consisting of aliphatic hydrocarbon functionality (preferably
containing from 1 to 8 carbon atoms), cycloaliphatic hydrocarbon functionality (preferably containing from 4 to 10
carbon atoms), aromatic hydrocarbon functionality (preferably containing from 6 to 12 carbon atoms), isocyanurate
functionality, iminooxadiazindione functionality, ether functionality, ester functionality, amide functionality, carbonate
functionality, urethane functionality, urea functionality,
biuret functionality, allophanate functionality, uretdione
functionality and any combination thereof.

Figure 4:
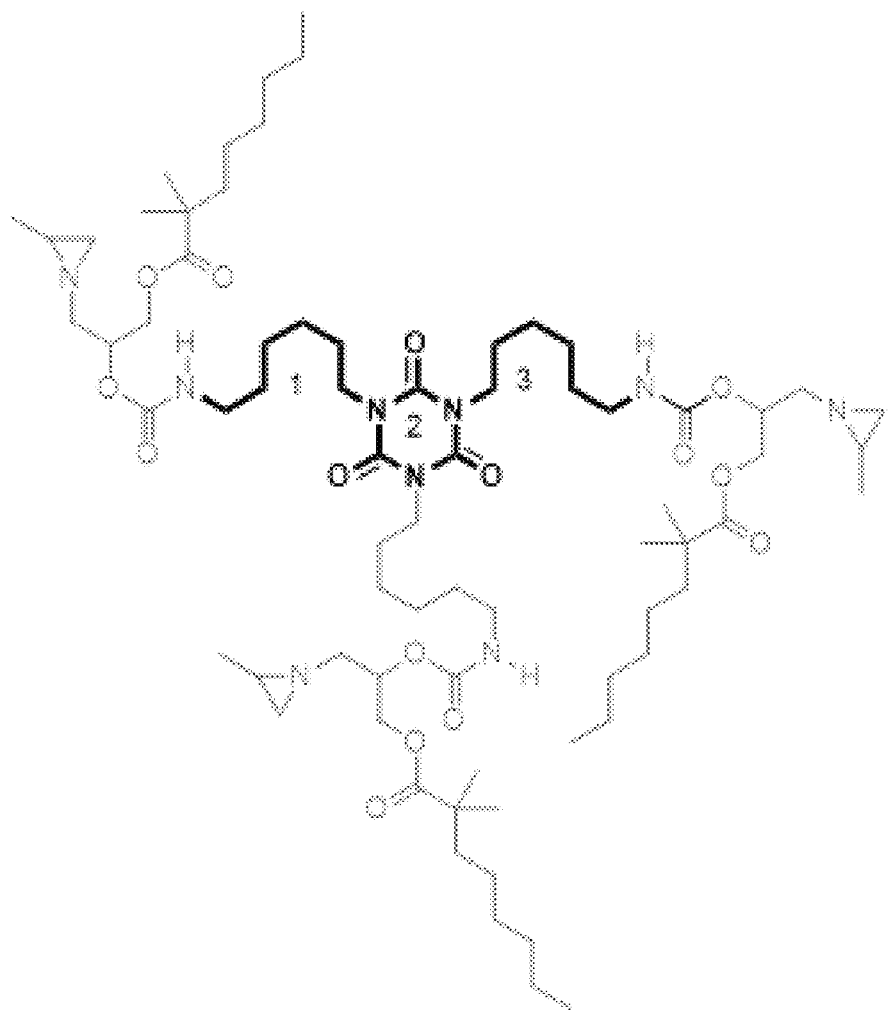

FIG. 4 shows in bold a connecting group for an example
of a multi-aziridine compound according to the invention. In
this example, the connecting group connecting two of the
structural units A consists of the array of the following
consecutive functionalities: aliphatic hydrocarbon functionality 1 (a linear $C_6H_{12}$), isocyanurate 2 (a cyclic $C_3N_3O_3$)
functionality and aliphatic hydrocarbon functionality 3 (a
linear $C_6H_{12}$).

Figure 5:
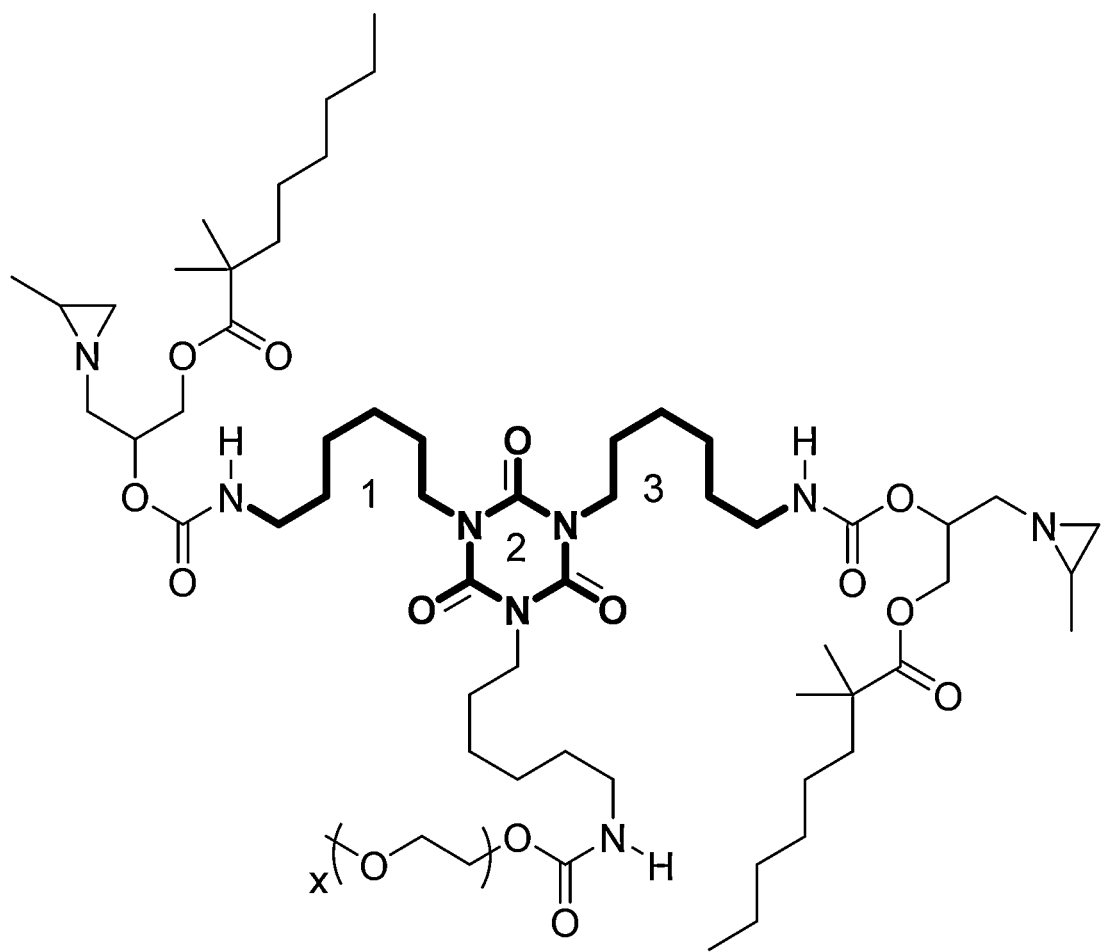

FIG. 5 shows in bold the connecting group for the
following example of a multi-aziridine compound according
to the invention. In this example, the connecting group
connecting the two structural units A consists of the array of
the following consecutive functionalities: aliphatic hydrocarbon functionality 1 (a linear $C_6H_{12}$), isocyanurate 2 (a
cyclic $C_3N_3O_3$) and aliphatic hydrocarbon functionality 3 (a
linear $C_6H_{12}$).

Any two of the structural units A present in the multi-aziridine compound of the invention are connected via a connecting group as defined herein. Accordingly, each structural unit A present in the multi-aziridine compound of the invention is connected to every other structural unit A with a connecting group as defined in the invention. In case the multi-aziridine compound according to the invention has two structural units A, the multi-aziridine compound has one such connecting group connecting these two structural units. In case the multi-aziridine compound according to the invention has three structural units A, the multi-aziridine compound has three such connecting groups, whereby each one of the three connecting groups is connecting a structural unit A with another structural unit A.

Figure 6A:
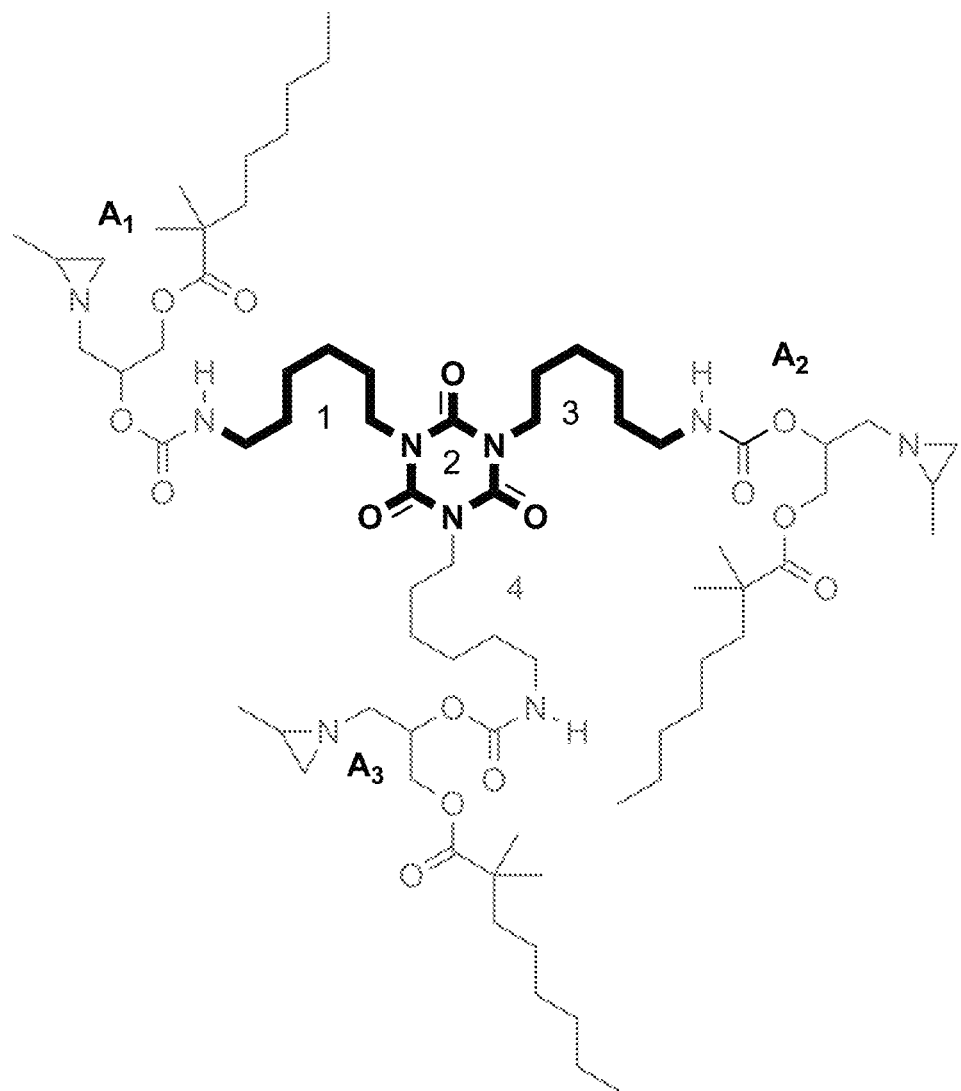
Figure 6B:
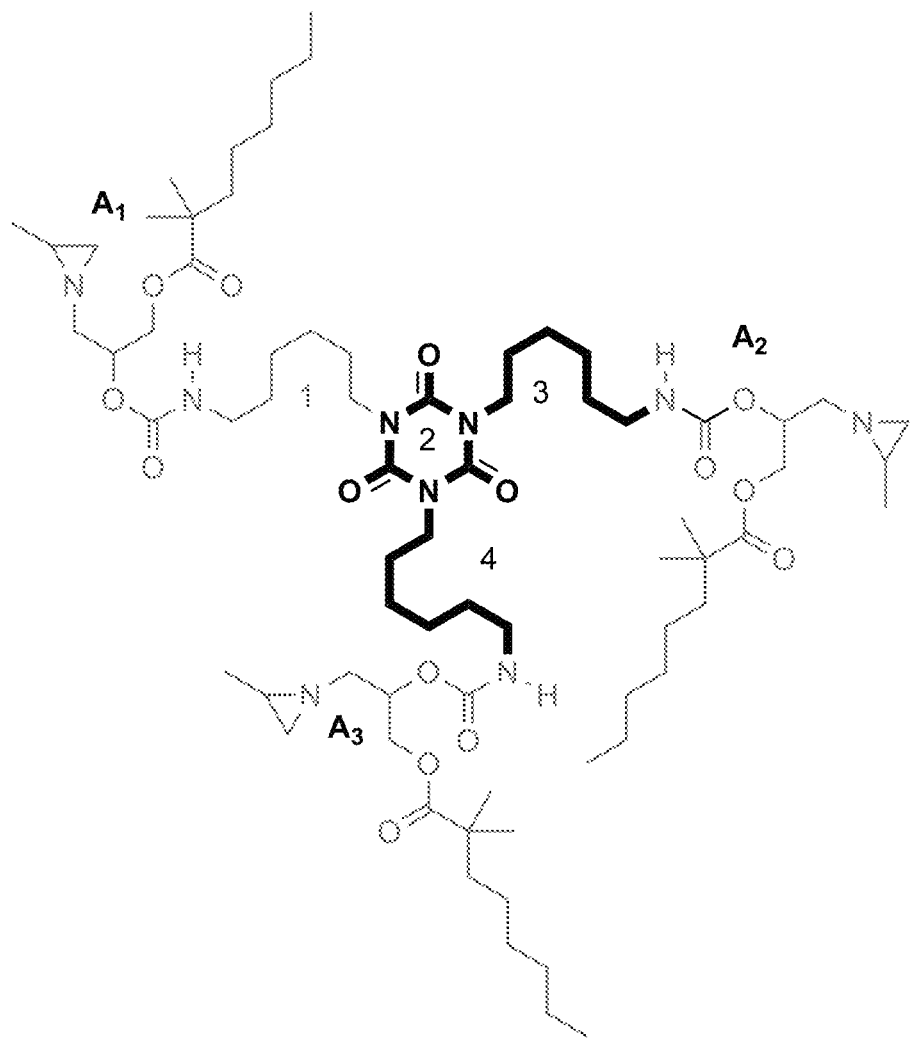
Figure 6C:
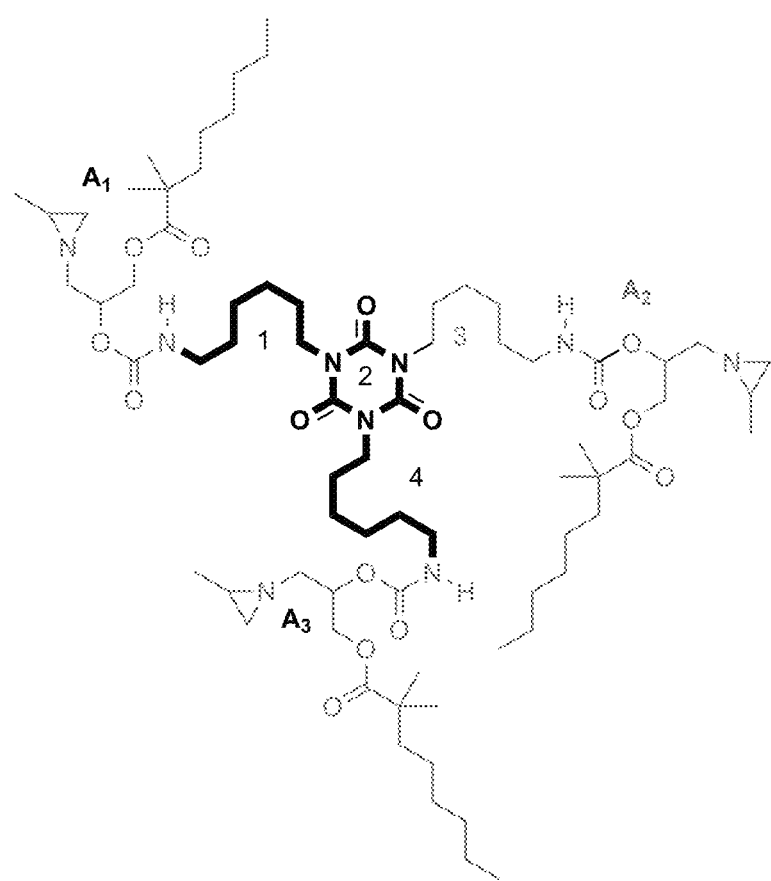

FIGS. 6A-6C show for an example of a multi-aziridine compound having three structural units A, the three connecting groups whereby each one of the three connecting groups is connecting two structural units A. One connecting group consists of the array of the following consecutive functionalities: aliphatic hydrocarbon functionality 1 (a linear $C_6H_{12}$), isocyanurate 2 (a cyclic $C_3N_3O_3$) and aliphatic hydrocarbon functionality 3 (a linear $C_6H_{12}$) connecting the structural units A which are labelled as A1 and A2. For the connection between structural units A which are labelled as A1 and A3, the connecting group consists of the array of the following consecutive functionalities: aliphatic hydrocarbon functionality 1 (a linear $C_6H_{12}$), isocyanurate 2 (a cyclic $C_3N_3O_3$) and aliphatic hydrocarbon functionality 4 (a linear $C_6H_{12}$), while for the connection between the structural units A which are labelled as A2 and A3, the connecting group consists of the array of the following consecutive functionalities: aliphatic hydrocarbon functionality 3 (a linear $C_6H_{12}$), isocyanurate 2 (a cyclic $C_3N_3O_3$) and aliphatic hydrocarbon functionality 4 (a linear $C_6H_{12}$).

Figure 7:
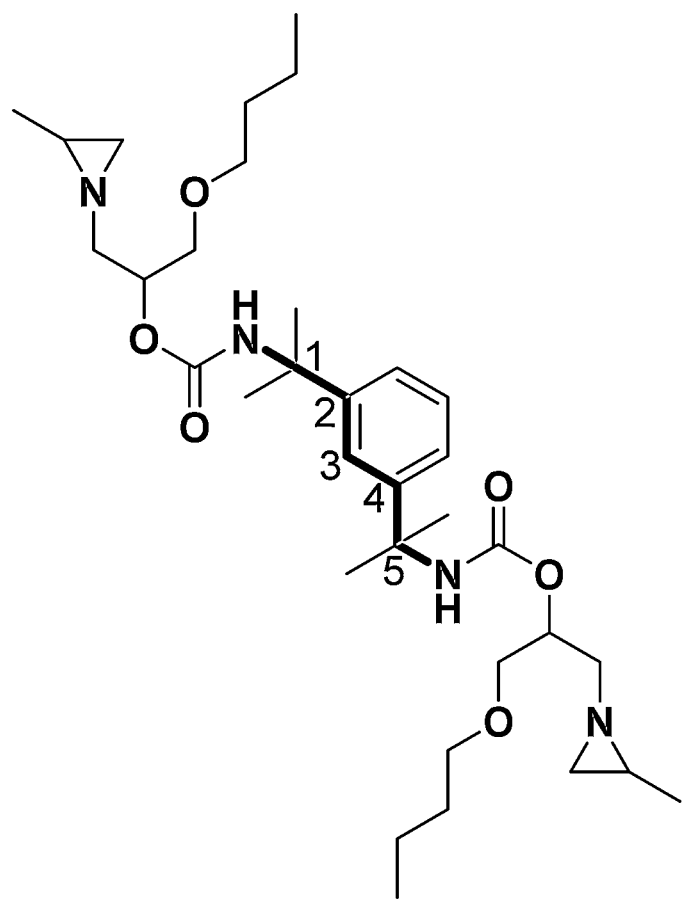

FIG. 7 shows, another example of a multi-aziridine compound according to the invention, with the linking chain between two structural units A.

Figure 8:
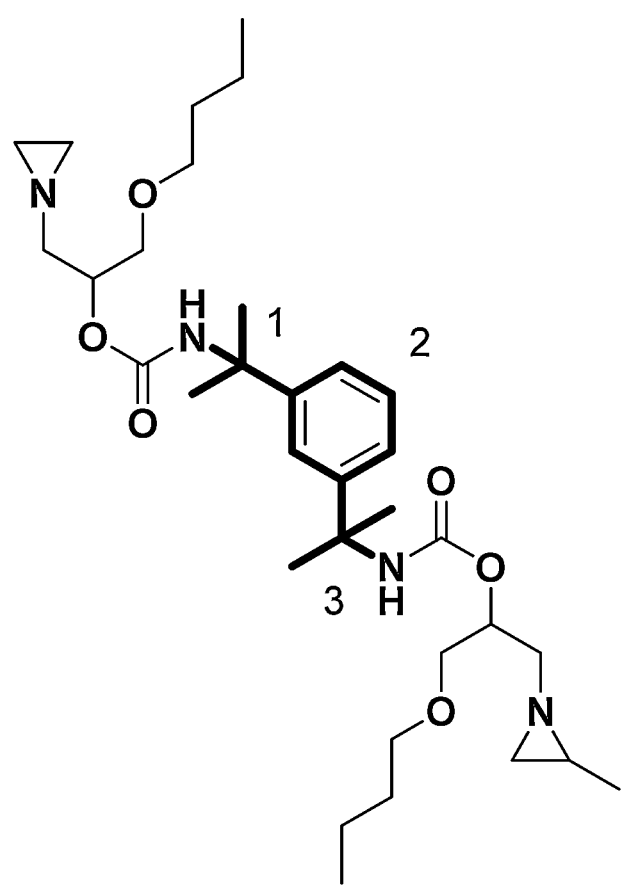

In FIG. 8, the connecting group connecting the two structural units A consists of the array of the following consecutive functionalities: aliphatic hydrocarbon functionality 1 (a branched $C_3H_6$), aromatic hydrocarbon functionality 2 (a benzene ring) and aliphatic hydrocarbon functionality 3 (a branched $C_3H_6$).

Figure 9:
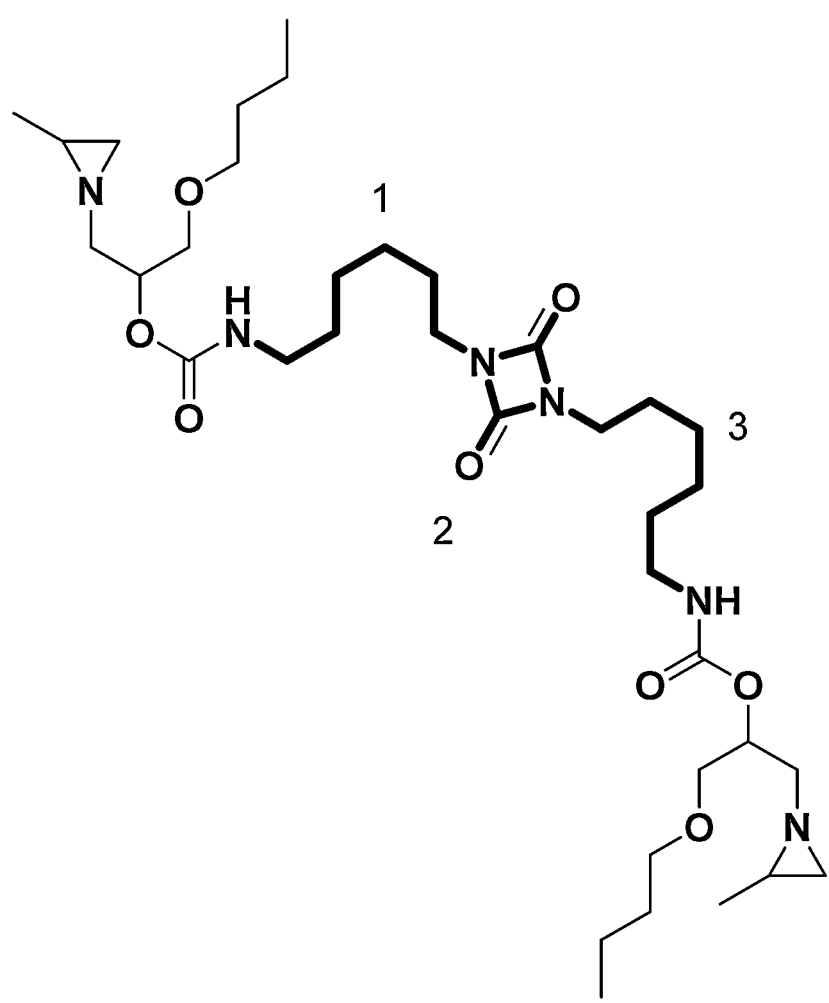

In FIG. 9 of the multi-aziridine compound according to the invention, the connecting group connecting the two structural units A consists of the array of the following consecutive functionalities: aliphatic hydrocarbon functionality 1 (a linear $C_6H_{12}$), uretdione 2 (a cyclic $C_2N_2O_2$) and aliphatic hydrocarbon functionality 3 (a linear $C_6H_{12}$).

Preferably, the connecting groups consist of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, urethane functionality, urea functionality, biuret functionality and any combination thereof. The connecting groups preferably contain an isocyanurate functionality, an iminooxadiazindione functionality, a biuret functionality, allophanate functionality or an uretdione functionality. More preferably, the connecting groups contain an isocyanurate functionality or an iminooxadiazindione functionality. For the sake of clarity, the multi-aziridine compound may be obtained from the reaction product of one or more suitable compound B and a hybrid isocyanurate such as for example a HDI/IPDI isocyanurate, resulting in a multi-aziridine compound with a connecting group consisting of the array of the following consecutive functionalities: a linear $C_6H_{12}$ (i.e. an aliphatic hydrocarbon functionality with 6 carbon atoms), an isocyanurate functionality (a cyclic $C_3N_3O_3$) and

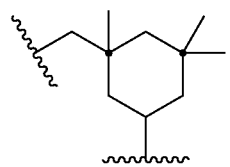

(i.e. a cycloaliphatic hydrocarbon functionality with 9 carbon atoms and an aliphatic hydrocarbon functionality with 1 carbon atom).

The term "aliphatic hydrocarbon functionality" refers to optionally branched alkyl, alkenyl and alkynyl groups. Whilst the optional branches of C atoms are part of the connecting group, they are not part of the linking chain. The term "cycloaliphatic hydrocarbon functionality" refers to cycloalkyl and cycloalkenyl groups optionally substituted with at least one aliphatic hydrocarbon group. Whilst the optional aliphatic hydrocarbon group substituents are part of the connecting group, they are not part of the linking chain. The term "aromatic hydrocarbon functionality" refers to a benzene ring optionally substituted with at least one aliphatic hydrocarbon group. The optionally substituted aliphatic hydrocarbon group is preferably an alkyl group. Whilst the optional aliphatic hydrocarbon group substituents are part of the connecting group, they are not part of the linking chain.

Figure 10:
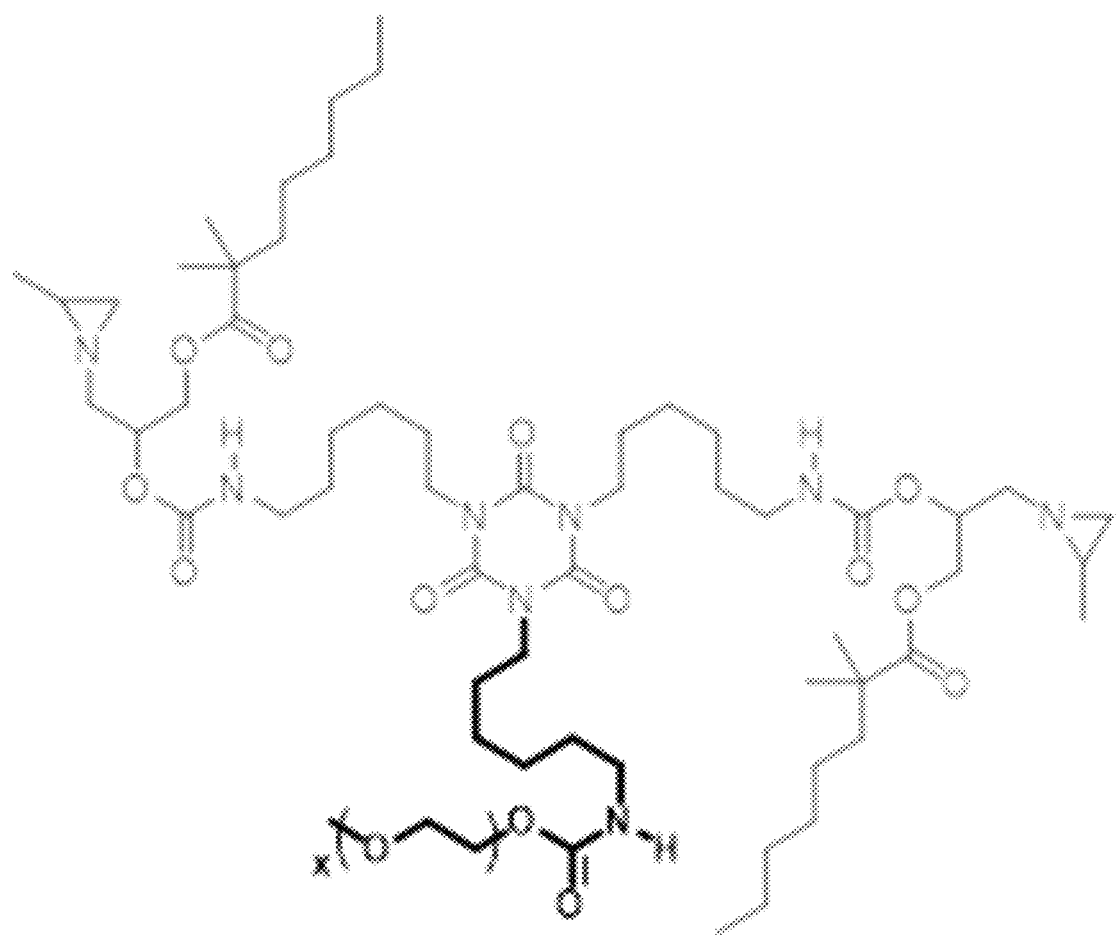

On the connecting groups, one or more substituents may be present as pendant groups on the connection group, as shown in bold in for example the following multi-aziridine compound of FIG. 10. These pendant groups are not part of the connecting groups.

An aziridinyl group has the following structural formula:

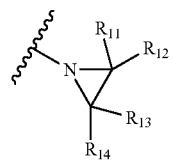

An isocyanurate functionality is defined as

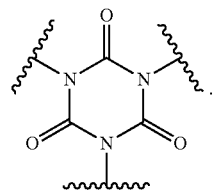 [SMILES: *n1c(=O)n(*)c(=O)n(*)c1=O]

An iminooxadiazindione functionality is defined as

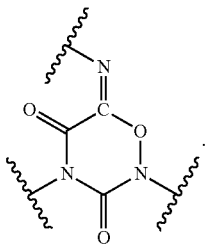 [SMILES: */N=c1/on(*)c(=O)n(*)c1=O]

An allophanate functionality is defined as

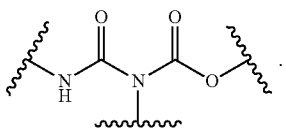 [SMILES: *NC(=O)N(*)C(=O)O*]

An uretdione functionality is defined as

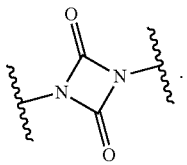 [SMILES: *N1C(=O)N(*)C1=O]

A biuret functionality is defined as

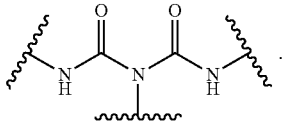 [SMILES: *NC(=O)N(*)C(=O)N*]

In a preferred embodiment of the invention, the connecting groups present in the multi-aziridine compound of the invention consist of the following functionalities: at least one aliphatic hydrocarbon functionality and/or at least one cycloaliphatic hydrocarbon functionality and optionally at least one aromatic hydrocarbon functionality and optionally an isocyanurate functionality or iminooxadiazindione functionality or allophanate functionality or uretdione functionality. Preferably, the connecting groups present in the multi-aziridine compound of the invention consist of the following functionalities: at least one aliphatic hydrocarbon functionality and/or at least one cycloaliphatic hydrocarbon functionality and optionally at least one aromatic hydrocarbon functionality and optionally an isocyanurate functionality or iminooxadiazindione functionality. A very suitable way of obtaining such multi-aziridine compound is reacting compound B with the following structural formula:

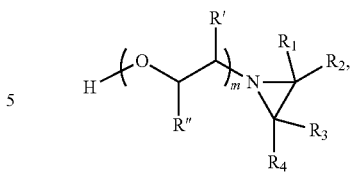

with a polyisocyanate with aliphatic reactivity. The term "a polyisocyanate with aliphatic reactivity" being intended to mean compounds in which all of the isocyanate groups are directly bonded to aliphatic or cycloaliphatic hydrocarbon groups, irrespective of whether aromatic hydrocarbon groups are also present. The polyisocyanate with aliphatic reactivity can be a mixture of polyisocyanates with aliphatic reactivity. Compounds based on polyisocyanate with aliphatic reactivity have a reduced tendency of yellowing over time when compared to a similar compound but based on polyisocyanate with aromatic reactivity. The term "a polyisocyanate with aromatic reactivity" being intended to mean compounds in which all of the isocyanate groups are directly bonded to aromatic hydrocarbon groups, irrespective of whether aliphatic or cycloaliphatic groups are also present. Preferred polyisocyanates with aliphatic reactivity are 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, tetramethylxylene diisocyanate TMXDI (all isomers) and higher molecular weight variants like for example their isocyanurates, or iminooxadiazindiones. In this embodiment, preferably the connecting groups consist of the array of the following consecutive functionalities: aliphatic hydrocarbon functionality, aromatic hydrocarbon functionality and aliphatic hydrocarbon functionality (for example when using TMXDI for preparing the multi-aziridine compound) or the connecting groups consist of the array of the following consecutive functionalities: cycloaliphatic hydrocarbon functionality, aliphatic hydrocarbon functionality and cycloaliphatic hydrocarbon functionality (for example when using H12MDI for preparing the multi-aziridine compound) or more preferably, the connecting groups consist of the array of the following consecutive functionalities: aliphatic hydrocarbon functionality, isocyanurate functionality or iminooxadiazindione functionality, and aliphatic hydrocarbon functionality. Most preferably, in this embodiment, the connecting group consists of the array of the following consecutive functionalities: aliphatic hydrocarbon functionality, isocyanurate functionality, and aliphatic hydrocarbon functionality (for example when using an isocyanurate of 1,6-hexamethylene diisocyanate and/or an isocyanurate of 1,5-pentamethylene diisocyanate for preparing the multi-aziridine compound).

In another embodiment of the present invention, the multi-aziridine compound according to the invention is according to the following structural formula:

$$Z\text{---}(D_i)_q$$

in which Z is a molecular residue obtained by removing isocyanate reactive groups XH of a molecule;
q is an integer from 2 to 6;
i is the index for the different groups D and is an integer from 1 to q;

$D_i$ independently have the following structural formula

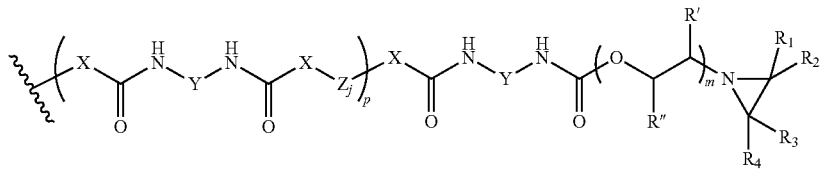

in which X is $NR_{11}$, S or O, whereby $R_{11}$ is H or an alkyl group with 1 to 4 carbon atoms;

Y is an aromatic hydrocarbon group, an aliphatic hydrocarbon group, a cycloaliphatic hydrocarbon group or a combination thereof;

j is an integer from 1 to p;

p is an integer from 0 to 10.

m, R', R'', $R_1$, $R_2$, $R_3$ and $R_4$ are as defined above. In this embodiment of the present invention, the multi-aziridine compound contains from 2 to 6 $D_i$ groups. Whilst the structural units $D_i$ may independently be the same or different, the structural units $D_i$ are preferably identical to each other.

Isocyanate reactive groups XH are herein defined as hydroxy groups (X is O), primary (X is NH) or secondary amines (X is $NR_{11}$ in which $R_{11}$ is an alkyl group with 1 to 4 carbon atoms) or mercaptans (X is S). Preferred isocyanate reactive groups XH are hydroxy groups (X is O), primary amines (X is NH) or secondary amines (X is $NR_{11}$ in which $R_{11}$ is an alkyl group with 1 to 4 carbon atoms). More preferred isocyanate reactive groups XH are hydroxy groups (X is O) and primary amines (X is NH). The molecule from which isocyanate reactive group are removed to obtain Z is preferably a diol, a triol, a polyether with terminal isocyanate reactive groups, a polyamide with terminal isocyanate reactive groups, a polycarbonate with terminal isocyanate reactive groups, or a polysiloxane with terminal isocyanate reactive groups which groups are linked to the siloxane via at least one carbon atom. In case Z is a molecular residue obtained by removing isocyanate reactive groups XH of a diol or a triol, the isocyanate reactive groups XH are hydroxy groups and thus X is O. In case Z is a molecular residue obtained by removing isocyanate reactive groups XH of a polyether with terminal isocyanate reactive groups or of a polyamide with terminal isocyanate reactive groups, the isocyanate reactive groups XH are preferably NH2 (thus X is NH) or OH (thus X is O) and more preferably the isocyanate reactive groups XH are OH (thus X is O). In case Z is a molecular residue obtained by removing isocyanate reactive groups XH of a polycarbonate with terminal isocyanate reactive groups, the isocyanate reactive groups are preferably OH and thus X is O.

In case j is larger than 1, Z can be the same or different.

Preferably, q is 2 or 3 and more preferably, q is 1.

Preferably, p is an integer from 0 to 10, more preferably from 0 to 5, most preferably from 0 to 3.

In this embodiment, p is most preferably 0 for all D, and accordingly $D_i$ independently have the following structural formula

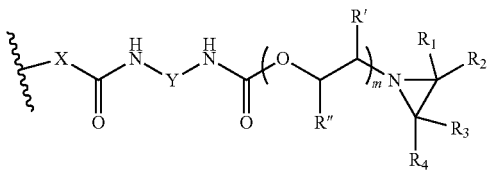

in which X, Y, m, R', R'', $R_1$, $R_2$, $R_3$ and $R_4$ are as defined above. Preferably m is 1.

Whilst the structural units $D_i$ may independently be the same or different, the structural units $D_i$ are preferably identical to each other.

The total amount of cyclic structures (apart from the aziridine groups) present in the multi-aziridine compound is preferably at most 3, since this results in a lower viscosity than when a higher amount of cyclic structures is present. Lower viscosity is easier to handle and/or less co-solvent is needed to make the compound more easy to handle. A multi-aziridine compound with more than three cyclic structures may result in more difficulties when dissolving such multi-aziridine if the multi-aziridine compound is solid at ambient temperature. The total amount of cyclic structures (apart from the aziridine groups) present in the multi-aziridine compound is more preferably from 0 to 2, even more preferably is 1 or 2, and most preferably is 1, which is preferably an isocyanurate or an iminooxadiazindione.

The multi-aziridine compound according to the invention preferably contains at least 5 wt. %, more preferably at least 5.5. wt. %, more preferably at least 6 wt. %, more preferably at least 9 wt. %, more preferably at least 12 wt. % and preferably less than 25 wt. %, preferably less than 20 wt. % of urethane bonds. The multi-aziridine compound according to the invention preferably has an aziridine equivalent weight (molecular weight of the multi-aziridine compound divided by number of aziridinyl groups present in the multi-aziridine compound) of at least 200, more preferably at least 230 and even more preferably at least 260 Daltons and preferably at most 2500, more preferably at most 1000 and even more preferably at most 500 Daltons.

The multi-aziridine compound can be stabilized if desired with 0.1 to 1 wt. % of a tertiary amine, preferably a betahydroxy amine like e.g. Amietol M21 or Amietol M-12.

The multi-aziridine compound according to the invention is preferably obtained by reacting at least a polyisocyanate and a compound B with the following structural formula:

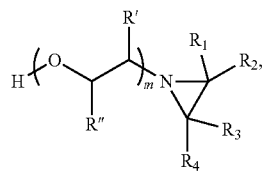

whereby the molar ratio of compound B to polyisocyanate is from 2 to 6, more preferably from 2 to 4 and most preferably from 2 to 3, and whereby m, R', R", $R_1$, $R_2$, $R_3$ and $R_4$ are as defined above. Reacting the polyisocyanate with compound B may be carried out by bringing equivalent amounts of the polyisocyanate into contact with the compound B at a temperature in the range of from 0 to 110° C., more suitable from 20° C. to 110° C., more suitable from 40° C. to 95° C., even more suitable from 60 to 85° C. in the presence of for example a tin catalyst such as for example dibutyltin laureate or a bismuth catalyst such as for example bismuth neodecanoate. A solvent may be used, such as for example dimethylformamide DMF, acetone and/or methyl ethyl ketone. The polyisocyanate contains at least 2 isocyanate groups, preferably at least 2.5 isocyanate groups on average and more preferably at least 2.8 isocyanate groups on average. Mixtures of polyisocyanates may also be used as starting materials. Preferred polyisocyanates are polyisocyanates with aliphatic reactivity. The term "a polyisocyanate with aliphatic reactivity" being intended to mean compounds in which all of the isocyanate groups are directly bonded to aliphatic or cycloaliphatic hydrocarbon groups, irrespective of whether aromatic hydrocarbon groups are also present. The polyisocyanate with aliphatic reactivity can be a mixture of polyisocyanates with aliphatic reactivity. Preferred polyisocyanates with aliphatic reactivity are 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, p-tetra-methylxylene diisocyanate (p-TMXDI) and its meta isomer, and higher molecular weight variants like for example their isocyanurates or iminooxadiazindiones or allophanates or uretdiones. More preferred polyisocyanates with aliphatic reactivity are 4,4'-dicyclohexyl methane diisocyanate H12MDI, m-TMXDI, an isocyanurate or iminooxadiazindione or allophanate or uretdione of 1,6-hexamethylene diisocyanate and an isocyanurate of 1,5-pentamethylene diisocyanate. A suitable HDI containing iminooxadiazindione trimer is Desmodur® N3900, obtainable from Covestro. A suitable HDI containing allophonate is Desmodur® XP2860, obtainable from Covestro. A suitable HDI containing uretdione is Desmodur® N3400, obtainable from Covestro. Suitable HDI based isocyanurates trimers can for example be obtained from Covestro (Desmodur® N3600), Vencorex (Tolonate™ HDT LV), Asahi Kasei (Duranate™ TPA-100), Evonik (Vestanat® HT 2500/LV) and Tosoh (Coronate® HXR LV). Methods for preparing compound (B) and derivatives are known in the art. For example, synthesis of 1-(2-methylaziridin-1-yl)propan-2-ol is described by S. Lesniak, M. Rachwalski, S. Jarzynski, E. Obijalska Tetrahedron Asymm. 2013, 24 1336-1340. Synthesis of 1-(aziridin-1-yl)propan-2-ol is described by A. Baklien, M. V. Leeding, J. Kolm Aust. J. Chem. 1968, 21, 1557-1570. Preferred aziridine compounds used for preparing compound B are propylene imine and ethylaziridine. Synthesis of ethylaziridine is for example described in EP0227461B1. Most preferred aziridine compounds used for preparing compound B is propylene imine.

Compound B is preferably obtained by reacting at least a non-OH functional monoepoxide compound with an aziridine compound with the following structural formula (C):

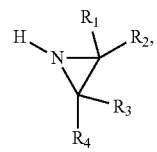

whereby $R_1$, $R_2$, $R_3$ and $R_4$ are as defined above. The non-OH functional monoepoxide may be a mixture of different non-OH functional monoepoxides. Non-limited examples of non-OH functional monoepoxide are ethylene oxide, propylene oxide, 2-ethyl oxirane, n-butylglycidylether, 2-ethylhexylglycidylether, phenyl glycidyl ether, 4-tert-butylphenyl 2,3-epoxypropyl ether (=t-butyl phenyl glycidyl ether), cresol glycidyl ether (ortho or para) and glycidyl neodecanoate. The non-OH functional monoepoxide is preferably selected from the group consisting of ethylene oxide (CAS number 75-21-8), propylene oxide (CAS number 75-56-9), 2-ethyl oxirane (CAS number 106-88-7), n-butylglycidylether (CAS number 2426-08-6), 2-ethylhexylglycidylether (CAS number 2461-15-6), glycidyl neodecanoate (CAS number 26761-45-5) and any mixture thereof. More preferably, the non-OH functional monoepoxide is selected from the group consisting of propylene oxide (CAS number 75-56-9), 2-ethyl oxirane (CAS number 106-88-7), n-butylglycidylether (CAS number 2426-08-6), 2-ethylhexylglycidylether (CAS number 2461-15-6), glycidyl neodecanoate (CAS number 26761-45-5) and any mixture thereof.

The multi-aziridine compound according to the invention is preferably obtained in a process comprising at least the following steps (i) and (ii):
  (i) Reacting an aziridine with formula (C) with at least a non-OH functional monoepoxide compound to obtain compound B, and
  (ii) Reacting compound B with a polyisocyanate.
    Step (i) can be carried out, for example, by bringing one equivalent of the epoxide compound into contact with one equivalent of the aziridine at a temperature in the range of from 20° C. to 110° C., more suitable from 40° C. to 95° C., even more suitable from 60 to 85° C. at atmospheric pressure. The reaction (step (ii)) of the adduct (compound (B)) obtained in step (i) with the polyisocyanate can be carried out, for example, by bringing equivalent amounts of the polyisocyanate into contact with the adduct at a temperature in the range of from 20° C. to 110° C., more suitable from 40° C. to 95° C. at atmospheric pressure, in the presence of for example a tin catalyst such as for example dibutyltin laureate.

In a preferred embodiment, the multi-aziridine compound according to the invention preferably contains polyoxyethylene ($-O-CH2-CH2-$)$_x$ group(s), polyoxypropylene ($-O-CHCH3-CH2-$)$_x$ group(s) and/or polytetrahydrofurane ($-O-CH2-CH2-CH2-CH2$)$_x$ groups, preferably in an amount of at least 0.1 wt. %, more preferably at least 6 wt. %, more preferably at least 10 wt. % and preferably in an amount of less than 45 wt. %, more preferably less than 25 wt. % and most preferably less than 16 wt. %, relative to the multi-aziridine compound. Preferably, the multi-aziridine compound contains polyoxyethylene ($-O-CH2-CH2-$)$_x$ group(s), preferably in an amount of at least 0.1 wt. %, more preferably at least 6 wt. %, more preferably at least 10 wt. % and preferably in an amount of less than 45 wt. %, more preferably less than 25 wt. % and most preferably less than 16 wt. %, relative to the multi-aziridine compound. For clarity, it should be noted that in case R'=H and R"=H respectively in case R'=H and R"=CH₃, one oxyethylene group respectively one oxypropylene group is present in the structural unit (A) and is then included in the preferred amount of oxyethylene group(s) or oxypropylene group(s) as defined herein. A multi-aziridine compound containing polyoxyethylene (—O—CH2-CH2-)$_x$ group(s) is preferably the reaction product of at least compound (B), a polyisocyanate and alkoxy poly(ethyleneglycol) (preferably methoxy poly(ethyleneglycol) (MPEG)) and/or poly(ethyleneglycol). The reaction product can be obtained by reacting at least compound (B), the polyisocyanate and alkoxy poly (ethyleneglycol) and/or poly(ethyleneglycol). The reaction product can also be obtained by reacting the polyisocyanate with alkoxy poly(ethyleneglycol) and/or poly(ethyleneglycol) and reacting the so-obtained compound with compound (B). The reaction product can also be obtained by reacting compound (B) with the polyisocyanate and reacting the so-obtained compound with alkoxy poly(ethyleneglycol) and/or poly(ethyleneglycol).

The amount of alkoxy poly(ethyleneglycol) (preferably methoxy poly(ethyleneglycol) (MPEG)) and/or poly(ethyleneglycol) (PEG) chains with a number average molecular weight $M_n$ higher than 2200 Daltons, preferably with a $M_n$ higher than 1600 Daltons in the multi-aziridine compound as defined above is preferably less than 35 wt. %, more preferably less than 15 wt. %, more preferably less than 5 wt. % and most preferably 0 wt. %. The methoxy poly(ethyleneglycol) (MPEG) and/or poly(ethyleneglycol) (PEG) chains present in the multi-aziridine compound preferably have a M, lower than 1100 Daltons, more preferably lower than 770 Daltons and most preferably lower than 570 Daltons.

Examples of preferred multi-aziridine compounds according to the invention are

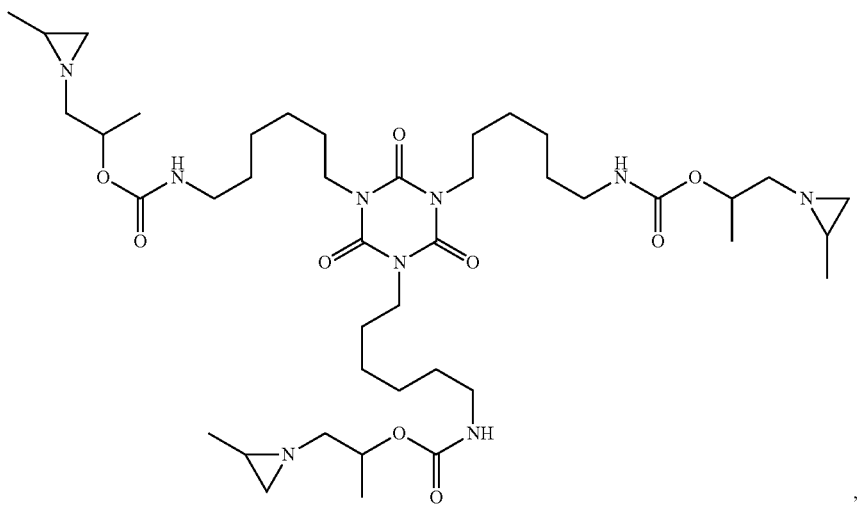

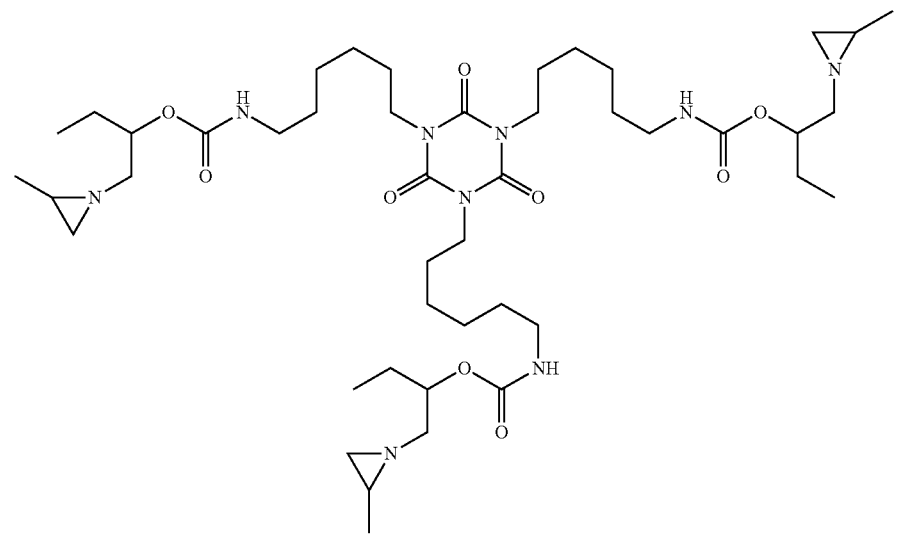

-continued

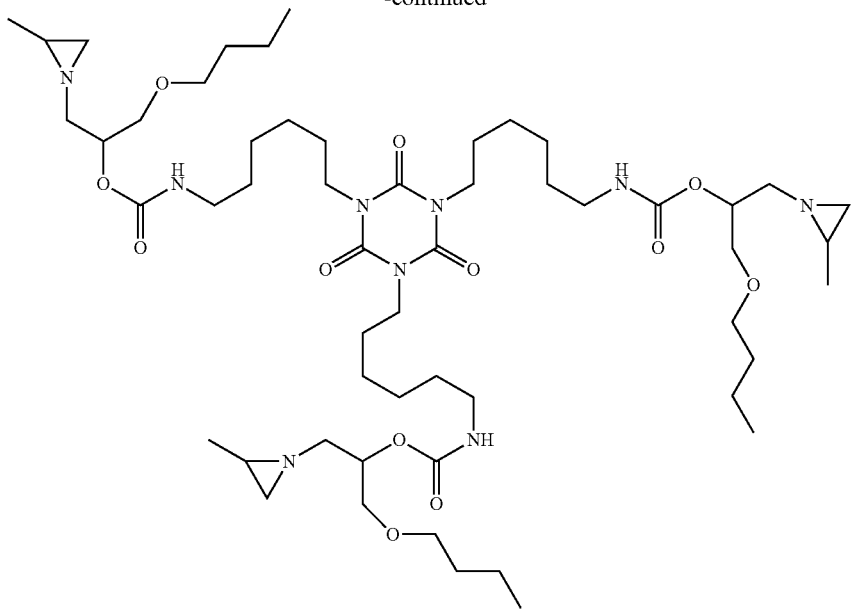

, and

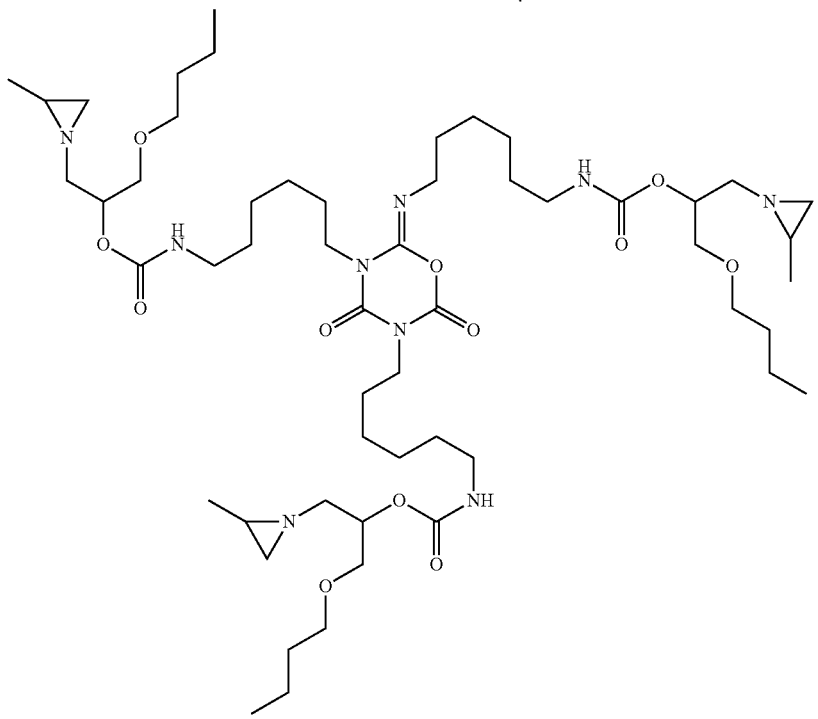

A further aspect of the current invention is a crosslinker composition comprising at least one multi-aziridine compound as defined above and further comprising at least one additional component, such as for example remaining starting materials, side-products and/or solvent used for preparing the multi-aziridine compound according to the invention. The crosslinker composition may contain only one multi-aziridine compound according to the invention but may also contain more than one multi-aziridine compound according to the invention. Mixtures of multi-aziridine compounds are for example obtained when a mixture of polyisocyanates as starting material to prepare the multi-aziridine are used. After having obtained the multi-aziridine compound(s) according to the invention, the multi-aziridine compound(s) according to the invention may be separated, the reaction product may be used without further purification or solvent used for preparing the multi-aziridine compound(s) may be removed from the composition obtained in the preparation of the multi-aziridine compound(s) of the invention. The amount of multi-aziridine compounds according to the invention in the crosslinker composition is usually at least 10 wt. %, usually often at least 15 wt. % and most often at least 25 wt. % relative to total amount of the composition. The amount of multi-aziridine compounds according to the invention in the crosslinker composition is preferably at least 60 wt. %, more preferably at least 80 wt. % and most preferably at least 99 wt. %, relative to total amount of the crosslinker composition. The molecular weight of the multi-aziridine compounds in the crosslinker composition is in the range of from 600 Daltons to 5000 Daltons. Preferred molecular weights are as described above and molecular weights of the multi-aziridine compounds are determined using MALDI-TOF-MS as described in the experimental part herein below. MALDI-TOF-MS means matrix-assisted laser desorption ionization time of flight mass spectroscopy.

The amount of aziridine functional molecules, present in the crosslinker composition according to the invention, having a molecular weight lower than 250 Daltons, more preferably lower than 350 Daltons, even more preferably lower than 450 Daltons, even more preferably lower than 550 Daltons and even more preferably lower than 580 Daltons is preferably lower than 5 wt. %, more preferably lower than 2 wt. %, more preferably lower than 1 wt. %, more preferably lower than 0.5 wt. % and most preferably lower than 0.1 wt. %, relative to the total weight of the crosslinker composition, whereby the molecular weight is determined using LC-MS as described in the experimental part below.

The average number of aziridinyl groups per aziridinyl-containing molecule in the composition is preferably at least 1.8, more preferably at least 2, more preferably at least 2.2 and preferably less than 10, more preferably less than 6 and most preferably less than 4. Most preferably, the average number of aziridinyl groups per aziridinyl-containing molecule in the composition is from 2.2 to 3. The calculated average amount of urethane bonds is at least 5 wt. %, more preferably at least 5.5. wt. %, more preferably at least 6 wt. %, more preferably at least 9 wt. %, more preferably at least 12 wt. % and preferably and less than 25 wt. %, preferably less than 20 wt. % of urethane bonds, relative to the total weight of the multi-aziridine compounds according to the invention present in the crosslinker composition.

In view of the potential water sensitivity of the multi-aziridine compounds according to the invention, the crosslinker composition is preferably free of substantial amount of water and more preferably is free of water. Free of substantial amount of water means less than 15 wt. %, preferably less than 5 wt. %, more preferably less than 1 wt. % and most preferably less than 0.1 wt. %. In view of the potential water sensitivity of the multi-aziridine compounds according to the invention, water is preferably not deliberately (i.e. small amounts of water may be present in the compounds used to prepare the multi-aziridine compound(s) according to the invention) be added to the composition.

The multi-aziridine compounds according to the invention preferably have a Brookfield viscosity of at least 500 mPa·s at 25° C., more preferably at least 1200, more preferably at least 3000 and preferably at most 1000000, more preferably at most 100000, more preferably at most 30000, more preferably at most 10000 and most preferably at most 5000 mPa·s at 25° C. As used herein, the Brookfield viscosity is determined according to ISO 2555-89. In an alternative embodiment the viscosity of the multi-aziridine was measured with a Brookfield with spindle S63, @25° C. at 80% solids, 20% in dimethyl formamide (DMF). The viscosity as measured according to this method is preferably in the range of 300 to 20000 mPas, more preferably in the range of from 500 to 12000 and most preferably in the range of from 700 to 3000 mPas, The multi-aziridine compounds according to the invention or the crosslinker composition comprising at least one multi-aziridine compound as defined above can be advantageously used as crosslinking agent for crosslinking a carboxylic acid functional polymer preferably dissolved and/or dispersed in an aqueous medium.

A further aspect of the present invention is a two-component system comprising a first component and a second component which is separate and distinct from each other, wherein the first component comprising a carboxylic acid functional polymer dissolved and/or dispersed in an aqueous medium and wherein the second composition comprising the multi-aziridine compound as defined above or the crosslinker composition comprising at least one multi-aziridine compound as defined above, whereby the first and second component are separately stored, since the crosslinking reaction between the crosslinking agent and the polymer to be crosslinked may start immediately after mixing the crosslinking agent with the aqueous composition of polymer to be crosslinked. Non-limited examples of crosslinkable carboxylic acid functional polymers are vinyl polymers like styrene-acrylics, (meth)acrylic copolymers, vinyl acetate (co)polymers such as for example vinyl acetate vinyl chloride ethylene polymers, polyurethanes, polycondensates like polyesters, polyamides, polycarbonates and hybrids of any of these polymers where at least one of the two polymers have a carboxylic acid functionality. The present invention further also relates to a coating composition obtained by mixing the first and second component of the two-component system just prior to application of the coating composition, whereby the coating composition comprises aziridinyl groups Q and carboxylic acid groups in an amount such that the stoichiometric amount (SA) of aziridinyl groups Q on carboxylic acid groups is preferably from 0.1 to 2.0, more preferably from 0.2 to 1.5, even more preferably from 0.25 to 0.95, most preferably from 0.3 to 0.8.

The present invention further relates to a substrate having a coating obtained by (i) applying a coating composition as described above to a substrate and (ii) drying the coating composition by evaporation of volatiles. The drying of the coating composition is preferably effected at a temperature lower than 160° C., preferably at a temperature lower than 90° C., more preferably at a temperature lower than 50° C. and most preferably at ambient temperature. The coating composition according to the invention can be applied to any kind of substrate, such as for example wood, leather, concrete, textile, plastic, vinyl floors, glass, metal, ceramics, paper, wood plastic composite, glass fiber reinforced materials. The thickness of the dry coating on the substrate is preferably from 1 to 200 micron, more preferably from 5 to 150 micron and most preferably from 15 to 90 microns. In case the coating composition is an ink composition, the thickness of the dry ink is preferably from 0.005 to 35 micron, more preferably from 0.05 to 25 micron and most preferably from 4 to 15 microns.

EXEMPLARY EMBODIMENTS

The invention is further defined by the set of exemplary embodiments as listed hereafter. Any one of the embodiments, aspects and preferred features or ranges as disclosed in this application may be combined in any combination, unless otherwise stated herein or if technically clearly not feasible to a skilled person.

[1] A multi-aziridine compound, wherein the multi-aziridine has from 2 to 6 of the following structural units (A):

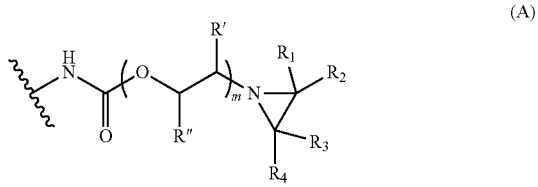

whereby $R_1$ is H;

$R_2$ and $R_4$ are independently chosen from H, a linear group containing from 1 to 8 carbon atoms and optionally containing one or more heteroatoms (preferably selected from N, S, O), a branched or cyclic group containing from 3 to 8 carbon atoms and optionally containing one or more heteroatoms (preferably selected from N, S, O), phenyl, benzyl, or pyridinyl;

$R_3$ is linear group containing from 1 to 8 carbon atoms and optionally containing one or more heteroatoms (preferably selected from N, S, O), a cycloaliphatic hydrocarbon group containing from 3 to 8 carbon atoms, phenyl, benzyl, or pyridinyl;

whereby $R_2$ and $R_3$ (in case $R_2$ is different than H) may be part of the same cyclic group containing from 3 to 8 carbon atoms;

$R'$=H or an aliphatic hydrocarbon group containing from 1 to 12 carbon atoms;

$R''$=H, an aliphatic hydrocarbon group containing from 1 to 12 carbon atoms, a cycloaliphatic hydrocarbon group containing from 5 to 12 carbon atoms, an aromatic hydrocarbon group containing from 6 to 12 carbon atoms, $CH_2$—O—(C=O)—$R'''$, $CH_2$—O—$R''''$, or $CH_2$—(OCR''''HCR''''H)$_n$—OR''''', whereby $R'''$ is an aliphatic hydrocarbon group containing from 1 to 12 carbon atoms and $R''''$ is an aliphatic hydrocarbon group containing from 1 to 12 carbon atoms or an aromatic hydrocarbon group containing from 6 to 12 carbon atoms, n being from 1 to 35, $R''''$ independently being H or an aliphatic hydrocarbon group containing from 1 to 12 carbon atoms and $R'''''$ being an aliphatic hydrocarbon group containing from 1 to 4 carbon atoms;

whereby $R'$ and $R''$ may be part of the same saturated cycloaliphatic hydrocarbon group containing from 5 to 8 carbon atoms;

m is an integer from 1 to 6;

the multi-aziridine compound further comprises one or more linking chains, wherein each one of these linking chains links two of the structural units A present in the multi-aziridine compound, whereby the linking chains preferably consist of from 2 to 300 atoms, more preferably from 5 to 250 and most preferably from 6 to 100 atoms; and wherein the molecular weight of the multi-aziridine compound is in the range from 600 Daltons to 5000 Daltons, whereby the molecular weight of the multi-aziridine compound is the calculated molecular weight or is measured using MALDI-TOF mass spectrometry as described in the experimental part below.

[2] The multi-aziridine compound of embodiment [1], wherein the multi-aziridine compound contains from 2 to 4 of the structural units (A), preferably 2 or 3 structural units (A), whereby the structural units (A) present in the multi-aziridine compound are preferably identical to each other.

[3] The multi-aziridine compound of embodiment [1] or [2], wherein $R_2$ and $R_4$ are independently chosen from H or an aliphatic hydrocarbon group containing from 1 to 8 carbon atoms, preferably $R_2$ and $R_4$ are independently chosen from H or an aliphatic hydrocarbon group containing from 1 to 4 carbon atoms, preferably $R_2$ and $R_4$ are independently chosen from H or an aliphatic hydrocarbon group containing from 1 to 2 carbon atoms.

[4] The multi-aziridine compound of any embodiments of [1] to [3], wherein $R_3$ is an aliphatic hydrocarbon group containing from 1 to 8 carbon atoms, preferably $R_3$ is an aliphatic hydrocarbon group containing from 1 to 4 carbon atoms.

[5] The multi-aziridine compound of any embodiments of [1] to [4], wherein $R_2$ is H, $R_3$ is $C_2H_5$ and $R_4$ is H.

[6] The multi-aziridine compound of any embodiments of [1] to [4], wherein $R_2$ is H, $R_3$ is $CH_3$ and $R_4$ is H.

[7] The multi-aziridine compound of any embodiments of [1] to [4], wherein $R_2$ is H, $R_3$ is $CH_3$ and $R_4$ is $CH_3$.

[8] The multi-aziridine compound of any embodiments of [1] to [7], wherein m is 1.

[9] The multi-aziridine compound of any embodiments of [1] to [8], wherein $R'$ is H or an alkyl group containing from 1 to 12 carbon atoms, preferably $R'$ is H or an alkyl group containing from 1 to 4 carbon atoms, more preferably $R'$ is H or an alkyl group containing from 1 to 2 carbon atoms.

[10] The multi-aziridine compound of any embodiments of [1] to [9], wherein $R''$ is H, an aliphatic hydrocarbon group containing from 1 to 8 carbon atoms (more preferably from 1 to 4 carbon atoms), a cycloaliphatic hydrocarbon group containing from 5 to 12 carbon atoms, an aromatic hydrocarbon group containing from 6 to 12 carbon atoms, $CH_2$—O—(C=O)—$R'''$, $CH_2$—O—$R''''$, or $CH_2$—(OCR''''HCR''''H)$_n$—OR'''''', whereby $R'''$ is an aliphatic hydrocarbon group containing from 1 to 12 carbon atoms and $R''''$ is an aliphatic hydrocarbon group containing from 1 to 12 carbon atoms or an aromatic hydrocarbon group containing from 6 to 12 carbon atoms, n being from 1 to 35, preferably from 6 to 20, $R''''$ independently being H or a methyl group and $R'''''$ being an aliphatic hydrocarbon group containing from 1 to 4 carbon atoms and preferably an alkyl group with 1 to 4 carbon atoms, or $R'$ and $R''$ may be part of the same saturated cycloaliphatic hydrocarbon group containing from 5 to 8 carbon atoms. More preferably, $R'$ is H and $R''$=an alkyl group containing from 1 to 4 carbon atoms, $CH_2$—O—(C=O)—$R'''$, $CH_2$—O—$R''''$, or $CH_2$—(OCH$_2$CH$_2$)$_n$—OCH$_3$ whereby $R'''$ is preferably an alkyl group containing from 3 to 12 carbon atoms, more preferably a branched alkyl group with from 3 to 12 carbon atoms, most preferably R''' is a branched C9 alkyl; R'''' is preferably an alkyl group containing from 1 to 12 carbon atoms.

[11] The multi-aziridine compound of any embodiments of [1] to [10], wherein the atoms of the linking chains are C, N, O, S and/or P, preferably C, N and/or O.

[12] The multi-aziridine compound of any embodiments of [1] to [11], wherein the number of consecutive C atoms and optionally O atoms between the N atom of the urethane in a structural unit A and the next N atom which is either present in the linking chain or which is the N atom of the urethane of another structural unit A is at most 9.

[13] The multi-aziridine compound of any embodiments of [1] to [12], wherein the multi-aziridine compound comprises one or more connecting groups wherein each one of these connecting groups connects two of the structural units A present in the multi-aziridine compound, in which the connecting groups consist of at least one functionality selected from:
aliphatic hydrocarbon functionality (preferably containing from 4 to 10 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, ether functionality, ester functionality, amide functionality, carbonate functionality, urethane functionality, urea functionality, biuret functionality, allophanate functionality, uretdione functionality and any combination thereof.

[14] The multi-aziridine compound of any embodiments of [1] to [13], wherein the connecting groups consist of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, urethane functionality, urea functionality, biuret functionality and any combination thereof.

[15] The multi-aziridine compound of any embodiments of [1] to [14], wherein the connecting groups preferably contain an isocyanurate functionality, an iminooxadiazindione functionality or a biuret functionality.

[16] The multi-aziridine compound of any embodiments of [1] to [15], wherein the multi-aziridine compound has a molecular weight of at least 700 Daltons, more preferably at least 800 Daltons, even more preferably at least 840 Daltons, even more preferably at least 1000 Daltons and preferably at most 3800 Daltons, more preferably at most 3600 Daltons, more preferably at most 3000 Daltons, more preferably at most 1600 Daltons, even more preferably at most 1200 Daltons.

[17] The multi-aziridine compound of any embodiments of [1] to [16], wherein the connecting groups of the multi-aziridine compound consist of the following functionalities: at least one aliphatic hydrocarbon functionality and/or at least one cycloaliphatic hydrocarbon functionality and optionally at least one aromatic hydrocarbon functionality and optionally an isocyanurate functionality or iminooxadiazindione functionality.

[18] The multi-aziridine compound of any embodiments [1] to [17], wherein the multi-aziridine compound is obtained by reacting compound B with the following structural formula:

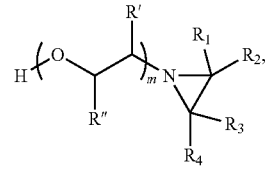

with a polyisocyanate with aliphatic reactivity.

[19] The multi-aziridine compound of embodiment [18], wherein the polyisocyanate with aliphatic reactivity is selected from 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, tetramethylxylene diisocyanateTMXDI (all isomers) and higher molecular weight variants like for example their isocyanurates or iminooxadiazindiones.

[20] The multi-aziridine compound of any embodiment of [13] to [18], wherein the connecting groups of the multi-aziridine compound consist of the array of the following consecutive functionalities: aliphatic hydrocarbon functionality, aromatic hydrocarbon functionality and aliphatic hydrocarbon functionality (for example when using TMXDI for preparing the multi-aziridine compound) or the connecting groups consist of the array of the following consecutive functionalities: cycloaliphatic hydrocarbon functionality, aliphatic hydrocarbon functionality and cycloaliphatic hydrocarbon functionality (for example when using H12MDI for preparing the multi-aziridine compound) or the connecting group consist of the array of the following consecutive functionalities: aliphatic hydrocarbon functionality, isocyanurate functionality or iminooxadiazindione functionality, and aliphatic hydrocarbon functionality or the connecting group consist of the array of the following consecutive functionalities: aliphatic hydrocarbon functionality, isocyanurate functionality, and aliphatic hydrocarbon functionality (for example when using an isocyanurate of 1,6-hexamethylene diisocyanate and/or an isocyanurate of 1,5-pentamethylene diisocyanate for preparing the multi-aziridine compound).

[21] The multi-aziridine compound of any embodiments of [1] to [12], wherein the multi-aziridine compound according to the invention is according to the following structural formula:

in which Z is a molecular residue obtained by removing isocyanate reactive groups XH of a molecule;

q is an integer from 2 to 6;

i is the index for the different groups $D_i$ and is an integer from 1 to q;

$D_i$ independently have the following structural formula

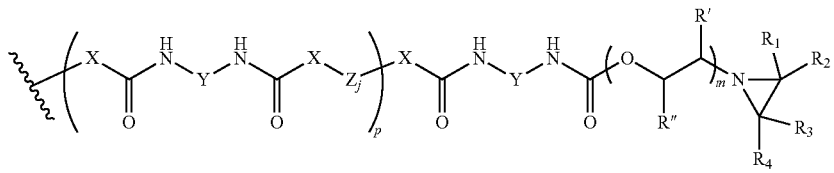

in which X is $NR_{11}$, S or O, whereby $R_{11}$ is H or an alkyl group with 1 to 4 carbon atoms; Y is an aromatic hydrocarbon group, an aliphatic hydrocarbon group, a cycloaliphatic hydrocarbon group or a combination thereof; j is an integer from 1 to p; Z is a molecular residue obtained by removing isocyanate reactive groups XH of a molecule; p is an integer from 0 to 10, m, R', R", $R_1$, $R_2$, $R_3$ and $R_4$ are as defined above, whereby isocyanate reactive groups XH are herein defined as hydroxy groups (X is O), primary (X is NH) or secondary amines (X is $NR_{11}$ in which $R_{11}$ is an alkyl group with 1 to 4 carbon atoms) or mercaptans (X is S), preferred isocyanate reactive groups XH are hydroxy groups (X is O), primary amines (X is NH) or secondary amines (X is $NR_{11}$ in which $R_{11}$ is an alkyl group with 1 to 4 carbon atoms), more preferred isocyanate reactive groups XH are hydroxy groups (X is O) and primary amines (X is NH). Preferably the molecule from which isocyanate reactive group are removed to obtain Z is preferably a diol, a triol, a polyether with terminal isocyanate reactive groups, a polyamide with terminal isocyanate reactive groups, a polycarbonate with terminal isocyanate reactive groups, or a polysiloxane with terminal isocyanate reactive groups which groups are linked to the siloxane via at least one carbon atom, in case Z is a molecular residue obtained by removing isocyanate reactive groups XH of a diol or a triol, the isocyanate reactive groups XH are hydroxy groups and thus X is O, in case Z is a molecular residue obtained by removing isocyanate reactive groups XH of a polyether with terminal isocyanate reactive groups or of a polyamide with terminal isocyanate reactive groups, the isocyanate reactive groups XH are preferably NH2 (thus X is NH) or OH (thus X is O) and more preferably the isocyanate reactive groups XH are OH (thus X is O), in case Z is a molecular residue obtained by removing isocyanate reactive groups XH of a polycarbonate with terminal isocyanate reactive groups, the isocyanate reactive groups are preferably OH and thus X is O, in case j is larger than 1, Z can be the same or different, preferably, q is 2 or 3 and more preferably, q is 1, preferably p is an integer from 0 to 10, more preferably from 0 to 5, even more preferably from 0 to 3 and most preferably p is 0 and m is 0.

[22] A multi-aziridine compound having from 2 to 6, preferably from 2 to 4, more preferably from 2 to 3 of the structural units (A) as defined in embodiment [1], whereby $R_1$, $R_2$, $R_3$, $R_4$, R', R" and m are as defined in any of embodiment [1] to [10], wherein the multi-aziridine compound having a molecular weight from 600 Daltons to 5000 Daltons, preferably at least 700 Daltons, more preferably at least 800 Daltons, even more preferably at least 840 Daltons and preferably at most 3800 Daltons, more preferably at most 3600 Daltons, more preferably at most 3000 Daltons, more preferably at most 1600 Daltons, even more preferably at most 1200 Daltons and wherein the multi-aziridine compound further comprises one or more connecting groups wherein each one of these connecting groups connects two of the structural units A, in which the connecting groups consist of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, ether functionality, ester functionality, amide functionality, carbonate functionality, urethane functionality, urea functionality, biuret functionality, allophanate functionality, uretdione functionality and any combination thereof.

[23] The multi-aziridine compound of embodiment [22], wherein the connecting groups of the multi-aziridine compound consist of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, urethane functionality, urea functionality, biuret functionality and any combination thereof.

[24] The multi-aziridine compound of embodiments [22] or [23], wherein the connecting group preferably contains an isocyanurate functionality, an iminooxadiazindione functionality or a biuret functionality.

[25] The multi-aziridine compound of any embodiments of [22] to [23], wherein the connecting groups of the multi-aziridine compound consist of the following functionalities: at least one aliphatic hydrocarbon functionality and/or at least one cycloaliphatic hydrocarbon functionality and optionally at least one aromatic hydrocarbon functionality and optionally an isocyanurate functionality or iminooxadiazindione functionality.

[26] The multi-aziridine compound of any embodiments of [22] to [25], wherein the multi-aziridine compound further comprises one or more linking chains, wherein each one of these linking chains links two of the structural units A present in the multi-aziridine compound, whereby the linking chains preferably consist of from 2 to 300 atoms, more preferably from 5 to 250 and most preferably from 6 to 100 atoms.

[27] The multi-aziridine compound of embodiment [26], wherein the number of consecutive C atoms and optionally 0 atoms between the N atom of the urethane in a structural unit A and the next N atom which is either present in the linking chain or which is the N atom of the urethane of another structural unit A is at most 9

[28] The multi-aziridine compound of embodiment [22] to [27], wherein the multi-aziridine compound is obtained by reacting compound B with the following structural formula:

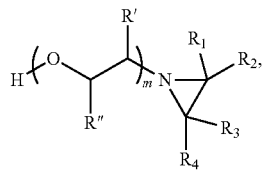

with a polyisocyanate with aliphatic reactivity.

[29] The multi-aziridine compound of embodiment [28], wherein the polyisocyanate with aliphatic reactivity is selected from 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, tetramethylxylene diisocyanate TMXDI (all isomers) and higher molecular weight variants like for example their isocyanurates or iminooxadiazindiones.

[30] The multi-aziridine compound of embodiment [28], wherein the connecting groups of the multi-aziridine compound consist of the array of the following consecutive functionalities: aliphatic hydrocarbon functionality, aromatic hydrocarbon functionality and aliphatic hydrocarbon functionality (for example when using TMXDI for preparing the multi-aziridine compound) or the connecting groups consist of the array of the following consecutive functionalities: cycloaliphatic hydrocarbon functionality, aliphatic hydrocarbon functionality and cycloaliphatic hydrocarbon functionality (for example when using H12MDI for preparing the multi-aziridine compound) or the connecting groups consist of the array of the following consecutive functionalities: aliphatic hydrocarbon functionality, isocyanurate functionality or iminooxadiazindione functionality, and aliphatic hydrocarbon functionality or the connecting groups consist of the array of the following consecutive functionalities: aliphatic hydrocarbon functionality, isocyanurate functionality, and aliphatic hydrocarbon functionality (for example when using an isocyanurate of 1,6-hexamethylene diisocyanate and/or an isocyanurate of 1,5-pentamethylene diisocyanate for preparing the multi-aziridine compound).

[31] A multi-aziridine compound having from 2 to 6, preferably from 2 to 4, more preferably from 2 to 3 of the structural units (A) as defined in embodiment [1], whereby $R_1$, $R_2$, $R_3$, $R_4$, R', R" and m are as defined in any of embodiment [1] to [10], wherein the multi-aziridine compound having a molecular weight from 600 Daltons to 5000 Daltons, preferably at least 700 Daltons, more preferably at least 800 Daltons, even more preferably at least 840 Daltons and preferably at most 3800 Daltons, more preferably at most 3600 Daltons, more preferably at most 3000 Daltons, more preferably at most 1600 Daltons, even more preferably at most 1200 Daltons, and wherein the multi-aziridine compound is obtained by reacting at least a polyisocyanate and a compound B with the following structural formula:

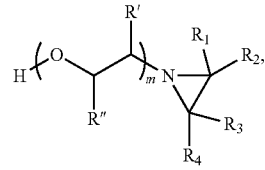

whereby the molar ratio of compound B to polyisocyanate is from 2 to 6, more preferably from 2 to 4 and most preferably from 2 to 3, and whereby m, R', R", $R_1$, $R_2$, $R_3$ and $R_4$ are defined as in any of embodiment [1] to [10].

[32] The multi-aziridine compound of embodiment [31], wherein the polyisocyanate is a polyisocyanate with aliphatic reactivity preferably selected from 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, tetramethylxylene diisocyanate TMXDI (all isomers) and higher molecular weight variants like for example their isocyanuratesor iminooxadiazindiones.

[33] The multi-aziridine compound of embodiment [31] or [32], wherein compound B is obtained by reacting at least a non-OH functional monoepoxide compound with an aziridine with the following structural formula:

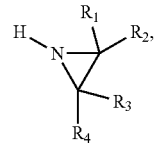

whereby $R_1$, $R_2$, $R_3$ and $R_4$ are defined as in any of embodiment [1] or [2] to [7], preferably the non-OH functional monoepoxide compound is selected from the group consisting of ethylene oxide, propylene oxide, 2-ethyl oxirane, n-butylglycidylether, 2-ethylhexylglycidylether, glycidyl neodecanoate and any mixture thereof.

[34] The multi-aziridine compound of any embodiment of [1] to [33], wherein the multi-aziridine compound contains polyoxypropylene (—O—CHCH3-CH2-)$_x$ groups or polytetrahydrofurane (—O—CH2-CH2-CH2-CH2)$_x$ groups or preferably polyoxyethylene (—O—CH2-CH2-)$_x$ groups or in an amount of at least 0.1 wt. %, more preferably at least 6 wt. %, more preferably at least 10 wt. % and preferably in an amount of less than 45 wt. %, more preferably less than 25 wt. % and most preferably less than 16 wt. %, relative to the multi-aziridine compound.

[35] The multi-aziridine compound of any embodiment of [1] to [34], wherein the amount of alkoxy poly(ethyleneglycol) (preferably methoxy poly(ethyleneglycol) (MPEG)) and/or poly(ethyleneglycol) (PEG) chains with a $M_n$ higher than 2200 Daltons, preferably with a $M_n$ higher than 1600 Daltons in the multi-aziridine compound as defined above is preferably less than 35 wt. %, more preferably less than 15 wt. %, more preferably less than 5 wt. % and most preferably 0 wt. % and the methoxy poly(ethyleneglycol) (MPEG) and/or poly(ethyleneglycol) (PEG) chains present in the multi-aziridine compound preferably have a $M_n$ lower than 1100 Daltons, more preferably lower than 770 Daltons and most preferably lower than 570 Daltons.

[36] The multi-aziridine compound of any embodiment of [1] to [35], wherein the amount of urethane bonds in the multi-aziridine compound is at least 5 wt. %, more preferably at least 5.5. wt. %, more preferably at least 6 wt. %, more preferably at least 9 wt. %, more preferably at least 12 wt. % and preferably less than 25 wt. %, preferably less than 20 wt. % and preferably the multi-aziridine compound has an aziridine equivalent weight (molecular weight of the multi-aziridine divided by number of aziridinyl groups) of at least 200, more preferably at least 230 and even more preferably at least 260 Daltons and preferably at most 2500, more preferably at most 1000 and even more preferably at most 500 Daltons.

[37] A crosslinker composition comprising at least one multi-aziridine compound according to any of embodiment [1] to [36], wherein the molecular weight of the multi-aziridine compounds according to any embodiment of [1] to [36] present in the crosslinker composition is in the range from 600 Daltons to 5000 Daltons, preferably at most 3800 Daltons, preferably the molecular weight is at most 3800 Daltons, more preferably at most 3600 Daltons, more preferably at most 3000 Daltons, more preferably at most 1600 Daltons, even more preferably at most 1200 Daltons and the molecular weight is preferably at least 700 Daltons, more preferably at least 800 Daltons, even more preferably at least 840 Daltons and most preferably at least 1000 Daltons; preferably the average number of aziridinyl groups per aziridinyl-containing molecule in the composition is at least 1.8, preferably at least 2, more preferably at least 2.2 and preferably less than 10, more preferably less than 6 and most preferably less than 4, most preferably, the average number of aziridinyl groups per aziridinyl-containing molecule in the composition is from 2.2 to 3.

[38] The crosslinker composition comprising at least one multi-aziridine compound according to any of embodiment [1] to [37], wherein the calculated average amount of urethane bonds present in the multi-aziridine compounds is at least 5 wt. %, more preferably at least 5.5. wt. %, more preferably at least 6 wt. %, more preferably at least 9 wt. %, more preferably at least 12 wt. % and preferably and less than 25 wt. %, preferably less than 20 wt. % of urethane bonds, relative to the total weight of the multi-aziridine compounds present in the composition.

[39] The crosslinker composition comprising at least one multi-aziridine compound according to any of embodiment [1] to [38], wherein the amount of aziridine functional molecules having a molecular weight lower than 250 Daltons, more preferably lower than 350 Daltons, even more preferably lower than 450 Daltons, even more preferably lower than 550 Daltons and even more preferably lower than 580 Daltons is lower than 5 wt. %, more preferably lower than 2 wt. %, more preferably lower than 1 wt. %, more preferably lower than 0.5 wt. % and most preferably lower than 0.1 wt. %, relative to the total weight of the crosslinker composition, whereby the molecular weight is determined using LC-MS as described in the experimental part below.

[40] A composition comprising a multi-aziridine(s), wherein the multi-aziridine(s) has at least two of the following structural units (A):

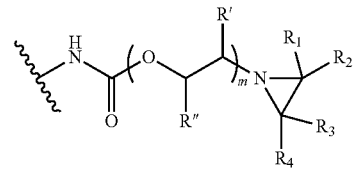

whereby
$R_1$ is H;
$R_2$ and $R_4$ are chosen from H, a (cyclo)aliphatic group containing from 1 to 8 carbon atoms and optionally containing heteroatom(s) in the chain, phenyl, benzyl, and pyridinyl;
$R_3$ is a (cyclo)aliphatic group containing from 1 to 8 carbon atoms and optionally containing heteroatom(s) in the chain, phenyl, benzyl, and pyridinyl;
or $R_2$ and $R_3$ (in case $R_2$ is different than H) may be part of the same saturated cycloaliphatic group;
R'=H or an alkyl group with from 1 to 12 carbon atoms;
R"=H, an aliphatic group with from 1 to 12 carbon atoms, a cycloaliphatic group with from 5 to 12 carbon atoms, an aromatic group with from 6 to 12 carbon atoms, $CH_2$—O—(C=O)—R''', $CH_2$—O—R'''', or $CH_2$—(OCR''''HCR''''H)$_n$—OCH$_3$, whereby R''' and R'''' independently are an alkyl group with from 1 to 12 carbon atoms, n being from 1 to 35 and R'''''' independently being H or an alkyl group with from 1 to 12 carbon atoms;
or R' and R" may be part of the same saturated cycloaliphatic group containing from 5 to 8 carbon atoms;
m is an integer from 1 to 35,
whereby the aziridinyl groups present in the multi-aziridine(s) are connected by at least one chain of atoms not containing (thio)ester functionalities and not containing dithioester functionalities and not containing disulphide functionalities, meaning that the aziridinyl groups which are connected via that chain of atoms are connected by bonds not being part of an ester group, a thioester group, a dithioester groups and a disulphide group and preferably also not of a (thio)amide group, preferably also not of an acetal group, and preferably also not of a phosph(on)ate group; and
wherein the number average molecular weight of the composition is in the range from 550 Daltons to 5000 Daltons.

[41] The composition according to embodiment [40], wherein pendant groups containing (thio)ester functionality are not present on the chain of atoms connecting the aziridine groups, in particular pendant groups containing (thio)ester functionality made from acids in which the carbon atom next to the carbonyl group is a secondary carbon atom, are preferably not present on the chain of atoms connecting the aziridine groups.

[42] The composition according to embodiment [40] or [41], wherein the multi-aziridine(s) present in the multi-aziridine composition according to the present invention are defined molecules, whereby the multi-aziridine(s) preferably contains at least 3 of the structural units (A) and preferably less than 10 of the structural units (A), more preferably less than 6 of the structural units (A) and more preferably less than 4 of the structural units (A), most preferably the multi-aziridine(s) contains 3 of the structural units (A).

[43] The composition according to any of embodiment [40] to [42], wherein the multi-aziridine composition according to the present invention is a mixture of defined molecules and the average amount of structural units (A) present in the multi-aziridines is preferably at least 2.2 and preferably less than 10, more preferably less than 6 and most preferably less than 4, preferably the structural units (A) present in the multi-aziridine(s) are preferably identical to each other.

[44] The composition according to any of embodiment [40] to [43], wherein the average amount of urethane bonds present in the multi-aziridine(s) is at least 5 wt. %, more preferably at least 5.5. wt. %, more preferably at least 6 wt. %, more preferably at least 9 wt. %, more preferably at least 12 wt. % and preferably less than 25 wt. %, preferably less than 20 wt. % of urethane bonds (relative to the total amount of the multi-aziridines present in the composition), whereby preferably polyisocyanates with at least 2 isocyanate groups are used to prepare the multi-aziridine composition according to the invention in an amount of preferably >50 wt. %, more preferably >80 wt. % and most preferably >100 wt. %, relative to the total amount of isocyanate containing compounds used to prepare the multi-aziridine composition.

[45] The composition according to any embodiment of [40] to [44], wherein the aziridinyl groups present in the multi-aziridine(s) are connected by at least one chain of atoms not containing (thio)amide functionalities, not containing acetal functionalities and not containing phosph(on)ate functionalities, and preferably the chain of atoms that connect two aziridinyl groups Q of the multi-aziridine(s) preferably has from 4 to 50 atoms (not including the atoms of the aziridinyl groups) and more preferably from 16 to 34 atoms.

[46] The composition according to any embodiment of [40] to [45], wherein $R_4$ is H and $R_2$ and $R_3$ are part of the same saturated cycloaliphatic group, or $R_2$ is H, $R_3$ is $CH_3$ and $R_4$ is H or $CH_3$, more preferably $R_4$ is H.

[47] The composition according to any embodiment of [40] to [45], wherein m is an integer from 1 to 35, preferably m is an integer from 1 to 6, more preferably m is an integer from 1 to 4, most preferably m=1.

[48] The composition according to any embodiment of [40] to [47], wherein n is an integer from 6 to 20 and preferably R' is H and R"=an alkyl group with from 1 to 8 carbon atoms (preferably $CH_3$ or $CH_2CH_3$), $CH_2$—O—(C=O)—R''' or $CH_2$—O—R'''', or $CH_2$—$(OCH_2CH_2)_n$—$OCH_3$ and R''' is an alkyl group with from 3 to 12 carbon atoms, more preferably a branched alkyl group with from 3 to 12 carbon atoms and R'''' is an alkyl group with from 1 to 12 carbon atoms, more preferably R" is $CH_2$—O—(C=O)—R''', $CH_2$—O—R'''', or $CH_2$—$(OCH_2CH_2)_n$—$OCH_3$.

[49] The composition according to any embodiment of [40] to [48], wherein the number average molecular weight of the composition comprising the multi-aziridine(s) (and/or the number average molecular weight of the multi-aziridine(s) present in the multi-aziridine composition) is in the range from 550 Daltons to 5000 Daltons, preferably at most 3000 Daltons, more preferably at most 1600 Daltons, even more preferably at most 1200 Daltons and preferably at least 840 Daltons and most preferably at least 1000 Daltons, whereby, the number average molecular weight of the composition comprising the multi-aziridine(s) is the number average molecular weight of the aziridine functional molecules and of the optional side-products obtained during preparation of the multi-aziridine(s) which are present in the multi-aziridine composition and the number average molecular weight is determined using MALDI-TOF mass spectrometry.

[50] The composition according to any embodiment of [40] to [49], wherein the amount of aziridine functional molecules having a molecular weight lower than 550 Daltons, more preferably lower than 700 Daltons and even more preferably lower than 840 Daltons is preferably lower than 5 wt. %, more preferably lower than 2 wt. %, more preferably lower than 1 wt. %, more preferably lower than 0.5 wt. % and most preferably lower than 0.1 wt. %, relative to the total weight of the composition comprising the multi-aziridine(s).

[51] The composition according to any embodiment of [40] to [50], wherein the total amount of cyclic structures (apart from the aziridine groups) present in the multi-aziridine(s) is preferably from 0 to 3, more preferably from 0 to 2, even more preferably is 1 or 2, and most preferably is 1 which is preferably an isocyanurate ring.

[52] The composition according to any embodiment of [40] to [51], wherein the multi-aziridine(s) is obtained by reacting a polyisocyanate and at least one β-hydroxyalkylene aziridine according to the following structure Q-CHR'—CHR"—OH, in which Q is according to the following structural formula

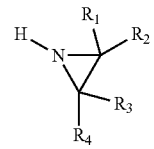

whereby R', R", $R_1$, $R_2$, $R_3$ and $R_4$ are as in any of the embodiments [50], [54] or [56].

[53] The composition according to any embodiment of [40] to [52], wherein the polyisocyanate contains at least 2 isocyanate groups, preferably 2.5 isocyanate groups on average and more preferably at least 2.8 isocyanate groups on average; preferably the polyisocyanate is selected from the group consisting of isocyanurates of an aliphatic diisocyanate not containing cyclic groups, iminooxadiazindione trimers of an aliphatic diisocyanate not containing cyclic groups, biuret trimers and any mixture thereof; more preferably, the polyisocyanate is an isocyanurate or iminooxadiazindione trimers of a linear (non-branched aliphatic) diisocyanate; even more preferably, the polyisocyanate is selected from the group consisting of an isocyanurate or iminooxadiazindione of 1,6-hexamethylene diisocyanate, an isocyanurate of 1,5-pentamethylene diisocyanate and any mixture thereof.

[54] The composition according to any embodiment of [52] to [53], wherein the β-hydroxyalkylene aziridine is obtained by reacting at least a non-OH functional monoepoxide compound with an aziridine compound with structural formula

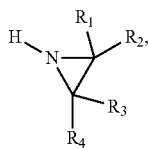

whereby $R_1$, $R_2$, $R_3$ and $R_4$ are as defined above.

[5] The composition according to any embodiment of [40] to [54], wherein the average amount of aziridinyl groups Q present in the multi-aziridine composition is at least 1.9, preferably at least 2.5, more preferably at least 2.7, more preferably at least 2.8, more preferably at least 2.9, and preferably less than 6.1, more preferably less than 5 and most preferably less than 3.5.

[56] The composition according to any embodiment of [40] to [55], wherein the multi-aziridine(s) is obtained by reacting at least the following reactants:
(i) An adduct of an aziridine with at least a non-OH functional monoepoxide compound, and
(ii) A polyisocyanate, preferably in an amount from 20 to 67 wt. % (relative to the total weight of the reactants), whereby the number average molecular weight of the multi-aziridine composition is at most 5000 Daltons, preferably at most 3000 Daltons, more preferably at most 1600 Daltons, more preferably at most 1200 Daltons and at least 550 Daltons, more preferably at least 840 Daltons and most preferably at least 1000 Daltons and the polydispersity is preferably less than 10, more preferably less than 5 and even more preferably less than 2 and whereby the polyisocyanate is preferably a tri-isocyanate, more preferably, the polyisocyanate is selected from the group consisting of an isocyanurate of 1,6-hexamethylene diisocyanate, an isocyanurate of 1,5-pentamethylene diisocyanate and any mixture thereof; the aziridine is preferably propylene imine (CAS number 75-55-8) or 2,2-dimethylaziridine (CAS number 2658-24-4), more preferably the aziridine is propylene imine.

[57] The composition according to embodiment [56], wherein the non-OH functional monoepoxide is selected from the group consisting of ethylene oxide, propylene oxide, 2-ethyl oxirane, n-butylglycidylether, 2-ethylhexylglycidylether, glycidyl neodecanoate and any mixture thereof.

[58] The composition according to any embodiment of [40] to [57], wherein the multi-aziridine(s) present in the composition contains oxyethylene (—O—CH2-CH2-) group(s) and/or oxypropylene (—O—CHCH3-CH2-) group(s), preferably in an amount of at least 0.1 wt. %, more preferably at least 6 wt. %, more preferably at least 10 wt. % and preferably in an amount of less than 45 wt. %, more preferably less than 25 wt. % and most preferably less than 16 wt. % (relative to the total amount of multi-aziridines present in the composition), preferably the multi-aziridine(s) present in the composition contains oxyethylene (—O—CH2-CH2-) group(s), preferably in an amount of at least 0.1 wt. %, more preferably at least 6 wt. %, more preferably at least 10 wt. % and preferably in an amount of less than 75 wt. %, more preferably less than 35 wt. % and most preferably less than 20 wt. % (relative to the total amount of multi-azirdine present in the composition).

[59] The composition according to any embodiment of [40] to [58], wherein amount of alkoxy poly(ethyleneglycol) (preferably methoxy poly(ethyleneglycol) (MPEG)) and/or poly(ethyleneglycol) (PEG) chains with a $M_n$ higher than 2200 Daltons, preferably with a $M_n$ higher than 1600 Daltons in the multi-aziridine(s) is preferably less than 35 wt. %, more preferably less than 15 wt. %, more preferably less than 5 wt. % and most preferably 0 wt. % and preferably the methoxy poly(ethyleneglycol) (MPEG) and/or poly(ethyleneglycol) (PEG) chains present in the crosslinking agent preferably have a M, lower than 1100 Daltons, more preferably lower than 570 Daltons.

[60] The composition according to any embodiment of [40] to [59], wherein the composition comprises less than 15 wt. %, preferably less than 5 wt. %, more preferably less than 1 wt. % and most preferably less than 0.1 wt. % of water.

[61] The composition according to any embodiment of [40] to [60], wherein the multi-aziridine(s) in its 100% form (without any diluents such as for example solvents and plasticizers) preferably has a Brookfield viscosity of at least 500 mPa·s at 25° C., more preferably at least 1200, more preferably at least 3000 and preferably at most 1000000, more preferably at most 100000, more preferably at most 30000, more preferably at most 10000 and most preferably at most 5000 mPa·s at 25° C., whereby the Brookfield viscosity is determined according to ISO 2555-89. In an alternative embodiment the viscosity of the multi-aziridine was measured with a Brookfield with spindle S63, @25° C. at 80% solids, 20% in dimethyl formamide (DMF); the viscosity as measured according to this method is preferably in the range of 300 to 20000 mPas, more preferably in the range of from 500 to 12000 and most preferably in the range of from 700 to 3000 mPas.

[62] The composition according to any embodiment of [40] to [61], wherein the multi-aziridine(s) present in the composition is a crosslinking agent suitable for crosslinking a carboxylic acid functional polymer

[63] Use of the composition as defined in any embodiment [1] to [62] for crosslinking a carboxylic acid functional polymer dissolved and/or dispersed in an aqueous medium.

[64] A multi-pack system comprising a first pack comprising a carboxylic acid functional polymer dissolved and/or dispersed in an aqueous medium and a second pack comprising the composition as defined in any embodiment [1] to [66], whereby the first and second pack are separately stored.

[68] A coating composition obtained by mixing the first and second pack of the multi-pack system of embodiment [64] just prior to application of the coating composition, whereby the coating composition comprises aziridinyl groups Q and carboxylic acid groups in an amount such that the stoichiometric amount (SA) of aziridinyl groups Q on carboxylic acid groups is from 0.1 to 2.0, more preferably from 0.2 to 1.5, even more preferably from 0.25 to 0.95, most preferably from 0.3 to 0.8.

[69] A substrate having a coating obtained by (i) applying a coating composition according to embodiment [68] to a substrate and (ii) drying the coating composition by evaporation of volatiles.

EXAMPLES

The present invention is now illustrated by reference to the following examples. Unless otherwise specified, all parts, percentages and ratios are on a weight basis.

Components and Abbreviations Used

Desmodur® N3600, Desmodur® N3900, Desmodur® N3400 and Desmodur® XP2860 were obtained from Covestro.
(±)-Allyl-2,3-epoxypropyl ether (allyl glycidyl ether, CAS No. 106-92-3) was obtained from Acros Organics (a division of Themo Fisher Scientific).
n-butylglycidyl ether (CAS No. 2426-08-6) was obtained from Alfa Aesar (a division of Themo Fisher Scientific).
dimethylformamide (68-12-2) was obtained from Acros Organics (a division of Themo Fisher Scientific).
$D_i$(propylene glycol) dimethyl ether (Proglyde DMM, CAS No. 111109-77-4) was obtained from Dow Inc
o-cresyl glycidyl ether (CAS No. 2210-79-9) was obtained from Sigma-Aldrich (a division of Merck KGaA).
mPEG-Epoxide (methoxyPEG-Epoxide), MW 550 Da and mPEG-Epoxide, MW 1 kDa were obtained from Creative PEGWorks (Chapel Hill, North Carolina, USA). trans-2,3-epoxybutane (CAS No. 21490-63-1) was obtained from abcr GmbH (Karlsruhe, Germany)
2-ethyloxirane (1,2-epoxybutane, CAS No. 106-88-7) was obtained from Sigma-Aldrich (a division of Merck KGaA).
Cyclohexene oxide (CAS No. 286-20-4) was obtained from Sigma-Aldrich (a division of Merck KGaA).
Polyethylene Glycol Monomethyl Ether (CAS No. 9004-74-4), with a number average molecular weight of 350 was obtained from Alfa Aesar (a division of Themo Fisher Scientific), with a number average molecular weight of 500 Da was obtained from Acros Organics (a division of Themo Fisher Scientific), with a number average molecular weight of 750 Da was obtained from Acros Organics (a division of Themo Fisher Scientific), with a number average molecular weight of 1000 Da was obtained from Tokyo Chemical Industry Co., Ltd. and with a number average molecular weight of 2000 Da was obtained from Tokyo Chemical Industry Co., Ltd.
2-ethyl hexyl glycidyl ether (CAS No. 2461-15-6) was obtained Sigma-Aldrich (a division of Merck KGaA).
2-Methyltetrahydrofuran (CAS No. 96-47-9) was obtained from Merck KgaA. Potassium carbonate (CAS No. 584-08-7) was obtained from Alfa Aesar (a division of Themo Fisher Scientific).
Cardura E10P (CAS No. 26761-45-5) was obtained from Hexion Inc.
NeoRez® R-1005, a polypropylene glycol based waterborne polyurethane dispersion with an acid-number of 6.26 mg KOH/g was obtained from DSM
Agisyn 2844 (ethoxylated (5) pentaerythritol tetraacrylate, CAS No. 51728-26-8) was obtained from DSM
DBTDL (dibutyltin dilaurate, CAS No. 77-58-7) was obtained from Reaxis
H12MDI (4,4'-Methylenebis(phenyl isocyanate, Desmodur® W, CAS No. 101-66-8) from Covestro.
Trimethylolpropane tris(2-methyl-1-aziridinepropionate), CAS No. 64265-57-2, CX-100 was obtained from DSM.
2,2-Dimethylaziridine (CAS No. 2658-24-4) was obtained from Enamine LLC (Monmouth Jct., NJ, United States of America).
2-Methylaziridine (propyleneimine, CAS No. 75-55-8) was obtained from Menadiona S. L. (Palafolls, Spain).
1,3-bis(2-isocyanatopropan-2-yl)benzene (m-tetramethylxylene diisocyanate, TMXDI, CAS No. 2778-42-9) was obtained Allnex
HDI (1,6-hexanediisocyanate, CAS No. 822-06-0) was obtained from Acros Organics (a division of Themo Fisher Scientific).
IPDI (5-Isocyanato-1-(isocyanatomethyl)-1,3,3-trimethylcyclohexane, Desmodur® I, isophorone diisocyanate, CAS No. 4098-71-9) was obtained from Covestro.
TMP (1,1,1-Tris(hydroxymethyl)propane, CAS Nol. 77-99-6) was obtained from Sigma-Aldrich (a division of Merck KGaA).
HDI (toluene diisocyanate, CAS No. 26471-62-5, Desmodur® T80, a 80/20 mixture of 2,4-toluene diisocyanate and 2,6-toluene diisocyanate) obtained from Covestro.
Durez-ter S105-110 (a polyester polyol with an OH-number of 110 mg KOH/g, based on adipic acid and hexane diol) obtained from Sumitomo Bakelite.
pTHF650 (polytetramethylene ether glycol with an OH-number of 172 mg KOH/g) obtained from BASF.
Bismuth neodecanoate (CAS No. 34364-26-6) obtained from TIB chemicals AG (Mannheim, Germany).
Phenothiazine (CAS No. 92-84-2) was obtained from Sigma-Aldrich (a division of Merck KGaA).
1-Butanol (CAS No. 71-36-3) was obtained from Sigma-Aldrich (a division of Merck KGaA).
1-methoxy-2-propanol acetate (propylene glycol methyl ether acetate, CAS No. 108-65-6) was obtained from Shell Chemicals.
Hydrazine (16% solution in water, CAS No. 302-01-2) was obtained from Honeywell.
Dimethylol propionic acid (DMPA, CAS No. 4767-03-7) was obtained from Perstop Polyols.
Triethylamine (TEA, CAS No. 121-44-8) was obtained from Arkema
Sodium lauryl sulphate (30% solution in water, CAS No. 73296-89-6) was obtained from BASF.
Methyl methacrylate (CAS No. 80-62-6) was obtained from Lucite Int.
n-Butyl acrylate (CAS No. 141-32-2) was obtained from Dow Chemical.
Methacrylic acid (CAS No. 79-41-4) was obtained from Lucite Int.
Ammonium persulphate (CAS No. 7727-54-0) was obtained from United Initiators.
Ammonia (25% solution in water, CAS No. 1336-21-6) was obtained from Merck.
Dipropylene glycol dimethyl ether (CAS No. 34590-94-8) was obtained from Dow Chemical.
2-Methyl-1,3-propane diol (CAS No. 2163-42-0) was obtained from Lyondell.
1,4-Butane diol (CAS No. 110-63-4) was obtained from BASF.
Adipic acid (CAS No. 124-04-9) was obtained from BASF.

LC-MS

LC-MS analysis for low molecular weight fraction was performed using the following procedure:
A solution of ~100 mg/kg of material was prepared gravimetrically in methanol and stirred. 0.5 μl of this solution was injected into a UPLC equipped with ESI-ToF-MS detection. The column used was a 100×2.1 mm, 1.8 um, Waters HSS T3 C18 operated at 40° C. Flow rate was 0.5 ml·min-1. Solvents used were 10 mM $NH_4CH_3COO$ (set to pH 9.0 with $NH_3$. Eluent A), Acetonitrile (B) and THF (C). 2 binary gradients were applied from 80/20 A/B to 1/99 A/B in 10 minutes and from 1/99 A/B to 1/49/50 A/B/C in 5 minutes, after which starting conditions are applied (80/20 A/B). Assuming linear MS response of all components over all response ranges and an equal ionization efficiency for all components, Total Ion Current signals were integrated. In case of coelution extracted ion chromatograms of that particular species were integrated.

MALDI-ToF-MS

All MALDI-ToF-MS spectra were acquired using a Bruker Ultraflextreme MALDI-ToF mass spectrometer. The instrument is equipped with a Nd:YAG laser emitting at 1064 nm and a collision cell (not used for these samples). Spectra were acquired in the positive-ion mode using the reflectron, using the highest resolution mode providing accurate masses (range 60-7000 m/z). Cesium Tri-iodide (range 0.3-3.5 kDa) was used for mass calibration (calibration method: IAV Molecular Characterisation, code MC-MS-05). The laser energy was 20%. The samples were dissolved in THF at approx. 50 mg/mL. The matrix used was: DCTB (trans-2-[3-(4-tert-Butylphenyl)-2-methyl-2-propenylidene]malononitrile), CAS Number 300364-84-5. The matrix solution was prepared by dissolving 20 mg in 1 mL of THF. Except for Comparative Examples 4, 6 and 8, for which potassium trifluoroacetate (KTFA, CAS Number: 2923-16-2) was used as salt, sodium iodide was used as salt (NaI, CAS Number 7681-82-5); 10 mg was dissolved in 1 ml THF with a drop of MeOH added. Ratio sample:matrix:salt=10:200:10 (µl), after mixing, 0.5 µL was spot on MALDI plate and allowed to air-dry. Reported signals are the major peaks within 0.5 Da of the calculated mass of the multi-aziridine compounds which are theoretically present in the composition in the largest amounts. In all cases the reported peaks are the sodium or potassium adducts of the measured ions.

Genotoxicity Testing

Genotoxicity of examples and comparatives was evaluated by the ToxTracker® assay (Toxys, Leiden, the Netherlands). The ToxTracker assay is a panel of several validated Green Fluorescent Protein (GFP)-based mouse embryonic stem (mES) reporter cell lines that can be used to identify the biological reactivity and potential carcinogenic properties of newly developed compounds in a single test. This methodology uses a two step-approach.

In the first step a dose range finding was performed using wild-type mES cells (strain B4418). 20 different concentrations for each compound was tested, starting at 10 mM in DMSO as highest concentration and nineteen consecutive 2-fold dilutions.

Next, genotoxicity of examples and comparatives was evaluated using specific genes linked to reporter genes for the detection of DNA damage; i.e. Bscl2 (as elucidated by U.S. Pat. No. 9,695,481B2 and EP2616484B1) and Rtkn (Hendriks et. al. Toxicol. Sci. 2015, 150, 190-203) biomarkers. Genotoxicity was evaluated at 10, 25 and 50% cytotoxicity in absence and presence of rat S9 liver extract-based metabolizing systems (aroclor1254-induced rats, Moltox, Boone, NC, USA). The independent cell lines were seeded in 96-well cell culture plates, 24 h after seeding the cells in the 96-well plates, fresh ES cell medium containing the diluted test substance was added to the cells. For each tested compound, five concentrations are tested in 2-fold dilutions. The highest sample concentration will induce significant cytotoxicity (50-70%). In case of no or low cytotoxicity, 10 mM or the maximum soluble mixture concentration is used as maximum test concentration. Cytotoxicity is determined by cell count after 24 h exposure using a Guava easyCyte 10HT flow cytometer (Millipore).

GFP reporter induction is always compared to a vehicle control treatment. DMSO concentration is similar in all wells for a particular compound and never exceeds 1%. All compounds were tested in at least three completely independent repeat experiments. Positive reference treatment with cisplatin (DNA damage) were included in all experiments. Metabolic was evaluated by addition of S9 liver extract. Cells are exposed to five concentrations of the test compound in the presence of S9 and required co-factors (RegenSysA+B, Moltox, Boone, NC, USA) for 3 h. After washing, cells are incubated for 24 h in fresh ES cell medium. Induction of the GFP reporters is determined after 24 h exposure using a Guava easyCyte 10HT flow cytometer (Millipore). Only GFP expression in intact single cells is determined. Mean GFP fluorescence and cell concentrations in each well is measured, which is used for cytotoxicity assessment. Data was analyzed using ToxPlot software (Toxys, Leiden, the Netherlands). The induction levels reported are at compound concentrations that induce 10%, 25% and 50% cytotoxicity after 3 h exposure in the presence of S9 rat liver extract and 24 h recovery or alternatively after 24 h exposure when not in the presence of S9 rat liver extract.

A positive induction level of the biomarkers is defined as equal to or higher than a 2-fold induction at at least one of 10, 25 and 50% cytotoxicity in the absence or presence of the metabolizing system rat S9 liver extract; a weakly positive induction as higher than 1.5-fold and lower than 2-fold induction at at least one of 10, 25 and 50% cytotoxicity (but lower than 2-fold at 10, 25 and 50% cytotoxicity) in the absence or presence of the metabolizing system rat S9 liver extract and a negative as lower than or equal to a 1.5-fold induction at 10, 25 and 50% cytotoxicity in the absence and presence of rat S9 liver extract-based metabolizing systems.

Comparative Example 1

Comparative Example 1 is CX-100, trimethylolpropane tris(2-methyl-1-aziridinepropionate). Chemical structure is shown below.

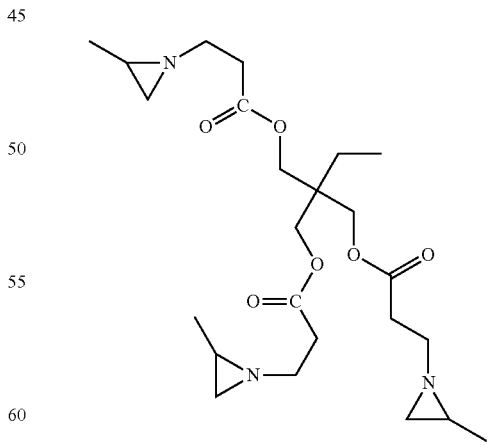

For reference, the performance of trimethylolpropane tris(2-methyl-1-aziridinepropionate) as a crosslinker was assessed using spot tests on coating surfaces, based on procedures from the DIN 68861-1 standard. For these tests, 0.23 parts of the compound were mixed with 0.60 parts of Proglyde™ DMM (dipropylene glycol dimethyl ether, mixture of isomers) and incubated at 80° C. for 10 minutes under regular agitation. Subsequently, 0.56 parts of the resulting solution were added to 20 parts of NeoRez® R-1005 under continuous stirring, and the resulting mixture was further stirred for 30 minutes. Afterwards, this coating composition was filtered and applied to Leneta test cards using 100 μm wire rod applicators (Test C1-1). The films were dried for 16 hours at 25° C., then annealed at 50° C. for 1 hour and further dried for 24 hours at 25° C. Subsequently, a piece of cotton wool was soaked in 1:1 EtOH demineralized water and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test C1-1 | 8 | 7 | 7 | 6 |

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Comp. Ex. 1 | 1.2 | 1.5 | 2.0 | 1.4 | 2.0 | 3.2 | 1.7 | 2.3 | 2.1 | 3.0 | 4.3 | 3.4 |

Comparative Example 2

508.7 grams of Agisyn 2844 and 0.26 grams of phenothiazine were charged to a stainless steel reactor equipped with a thermostat. The mixture was stirred with a mechanical upper stirrer under a nitrogen atmosphere. The mixture was than heated to 35° C., and subsequently 25.3 grams of propylene imine was added over 30 minutes. The mixture was then further heated to 45° C. and kept at that temperature for 36 hours. The resulting mixture, with a calculated molecular weight of the main component of 800.48 Da, was discharged and tested for genotoxicity. Chemical structure is shown below.

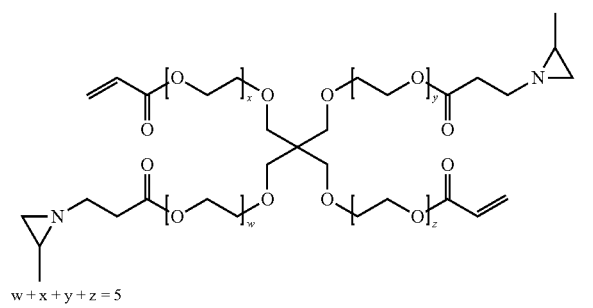

w + x + y + z = 5

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Comp. Ex. 2 | 1.1 | 1.3 | 1.3 | 1.3 | 1.6 | 1.8 | 1.1 | 1.4 | 1.4 | 1.1 | 1.7 | 2.4 |

Comparative Example 3

10.0 grams of 1,3-bis(1-isocyanato-1-methylethyl)benzene, 0.02 grams of bismuth neodecanoate, 3.56 grams of 1-(2-hydroxyethyl)ethyleneimine, 1.83 grams of a trimethylolpropane and 87 grams of dimethylformamide were charged to a reaction flask equipped with a thermometer. The mixture was stirred with a mechanical upper stirrer under a nitrogen atmosphere. The mixture was than heated to 50° C., kept at that temperature for 15 minutes and then heated further to 75° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a yellowish wax. The calculated molecular weights of the theoretical main components were 1127.66 Da (three aziridines) and 418.26 Da (two aziridines), chemical structures are shown below.

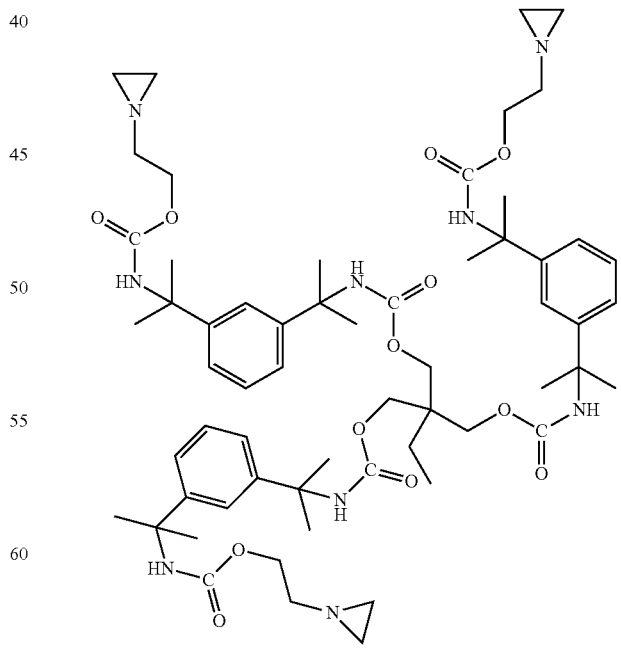

Molecular weight was confirmed by Maldi-TOF-MS: Calcd. [M+Na+]=1150.66 Da; Obs. [M+Na+]=1150.56 Da.

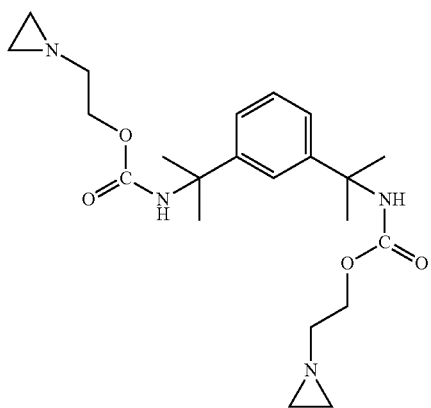 [SMILES: CC(C)(NC(=O)OCCN1CC1)c1cccc(C(C)(C)NC(=O)OCCN2CC2)c1]

Molecular weight was confirmed by Maldi-TOF-MS: Calcd. [M+Na+]=441.26; Obs. [M+Na+]=441.20 Da.

| | Genotoxicity test | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Comp. Ex. 3 | 1.2 | 1.6 | 2.1 | 1.5 | 2.5 | 2.6 | 1.5 | 2.2 | 2.4 | 1.6 | 2.9 | 4.8 |

Comparative Example 4

15.0 grams of Desmodur N 3600 and 75 grams of dimethylformamide were charged to a reaction flask equipped with a thermometer. The mixture was stirred with a mechanical upper stirrer under a nitrogen atmosphere. The mixture was than heated to 50° C., whereafter 6.80 grams of 1-(2-hydroxyethyl)ethyleneimine was added. 15 minutes later 0.03 grams of bismuth neodecanoate was charged to the reaction flask, which was then heated further to 60° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a clear, slightly yellowish highly viscous liquid. The calculated molecular weight of the theoretical main component was 765.47 Da, chemical structure is shown below.

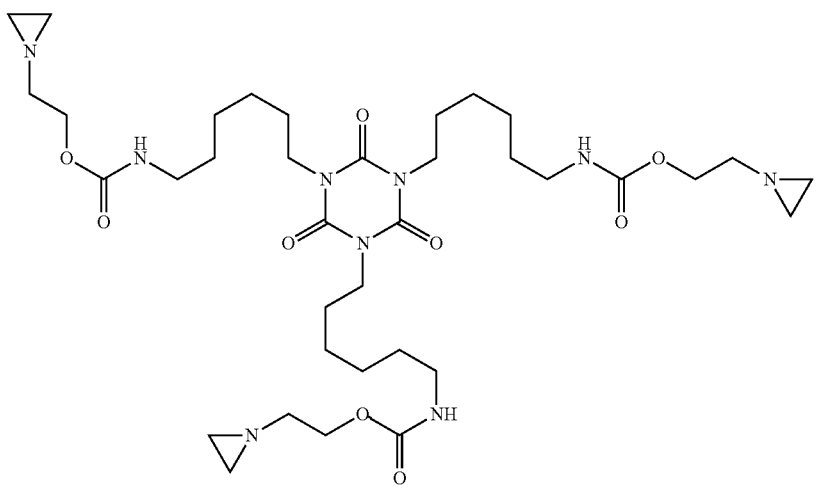

Molecular weight was confirmed by Maldi-TOF-MS: Calcd. [M+K+]=804.43 Da; Obs. [M+K+]=804.27 Da.

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Comp. Ex. 4 1.1 | 1.3 | 1.4 | 1.7 | 2.4 | 2.8 | 1.4 | 1.9 | 1.9 | 2.0 | 3.4 | 3.0 |

Molecular weight was confirmed by Maldi-TOF-MS: Calcd. [M+Na+]=830.52 Da; Obs. [M+Na+]=830.47 Da.

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Comp. Ex. 5 1.1 | 1.3 | 1.3 | 1.3 | 1.8 | 1.9 | 1.3 | 1.8 | 1.8 | 1.3 | 2.1 | 2.2 |

Comparative Example 5

2.60 grams of 1-(aziridin-1-yl)propan-2-ol, 0.02 grams of bismuth neodecanoate and 32 grams of dimethylformamide were charged to a reaction flask equipped with a thermometer. The mixture was stirred with a mechanical upper stirrer under a nitrogen atmosphere and heated to 50° C. A solution of 5.00 grams of Desmodur N 3600 in 32 grams of dimethylformamide was then added dropwise in 15 minutes to the reaction flask, where after the mixture was heated further to 70° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain an opaque highly viscous liquid. The calculated molecular weight of the theoretical main component was 807.52 Da, chemical structure is shown below.

Comparative Example 6

9.00 grams of 1,6-hexanediisocyanate and 74 grams of 2-methyltetrahydrofuran were charged to a reaction flask equipped with a thermometer. The mixture was stirred with a mechanical upper stirrer under a nitrogen atmosphere. The mixture was than heated to 40° C., upon reaching this temperature 12.20 grams of 1-(2-methylaziridin-1-yl)propan-2-ol was gradually charged. After a steep exotherm the reaction temperature was levelled out to 60° C. and kept at this temperature. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain an opaque viscous liquid. The calculated molecular weight of the theoretical main component was 398.29 Da, chemical structure is shown below.

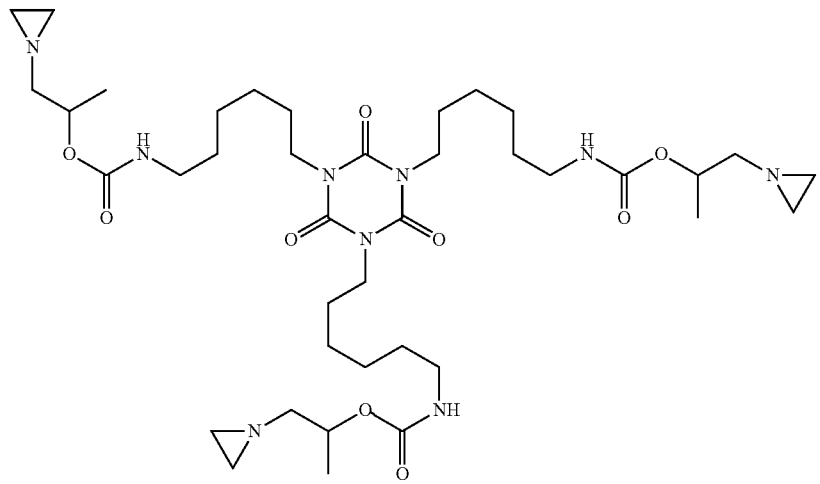

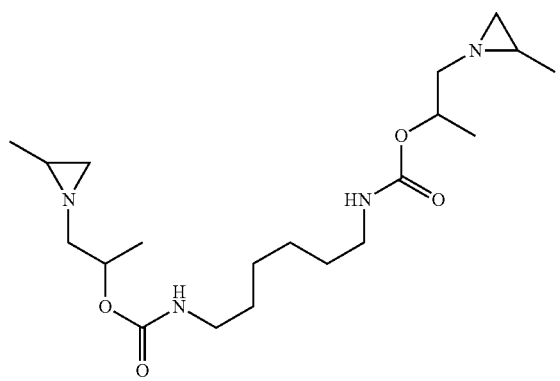

Molecular weight was confirmed by Maldi-TOF-MS: Calcd. [M+K+]=437.25 Da; Obs. [M+K+]=437.20 Da.

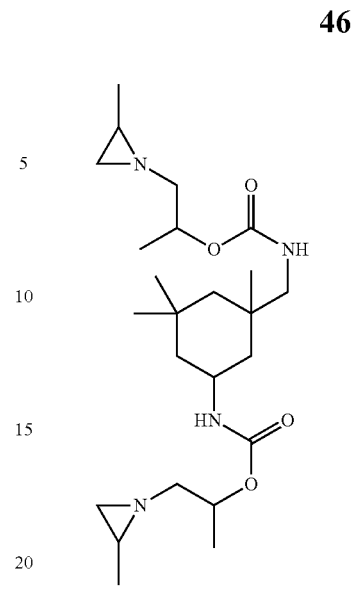

Molecular weight was confirmed by Maldi-TOF-MS: Calcd. [M+Na+]=475.34 Da; Obs. [M+Na+]=475.32 Da.

| | Genotoxicity test | | | |
|---|---|---|---|---|
| | Without S9 rat liver extract | | With S9 rat liver extract | |
| | Bscl 2 | Rtkn | Bscl 2 | Rtkn |
| | concentration | | | |
| | 10  25  50 | 10  25  50 | 10  25  50 | 10  25  50 |
| Comp. Ex. 6 | 1.4  2.0  2.0 | 2.1  3.1  3.1 | 1.4  2.1  2.3 | 2.2  3.4  2.1 |

| | Genotoxicity test | | | |
|---|---|---|---|---|
| | Without S9 rat liver extract | | With S9 rat liver extract | |
| | Bscl 2 | Rtkn | Bscl 2 | Rtkn |
| | concentration | | | |
| | 10  25  50 | 10  25  50 | 10  25  50 | 10  25  50 |
| Comp. Ex. 7 | 1.2  1.6  2.4 | 1.6  2.5  3.8 | 1.2  1.6  1.7 | 1.6  2.7  3.5 |

Comparative Example 7

3.00 grams of IPDI, 28 grams of DMF and 3.08 grams of 1-(2-methylaziridin-1-yl)propan-2-ol were charged to a reaction flask equipped with a thermometer. The mixture was stirred with a mechanical upper stirrer under a nitrogen atmosphere. The mixture was than heated to 50° C., upon reaching this temperature 0.02 grams of Bismuth neodecanoate. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a clear highly viscous liquid. The calculated molecular weight of the theoretical main component was 452.34 Da, chemical structure is shown below.

Comparative Example 8

8.95 grams of 1-(2-methylaziridin-1-yl)propan-2-ol, 0.02 grams of bismuth neodecanoate and 54 grams of dimethylformamide were charged to a reaction flask equipped with a thermometer. The mixture was stirred with a mechanical upper stirrer under a nitrogen atmosphere and heated to 50° C. A solution of 10.0 grams of 1,3-bis(1-isocyanato-1-methylethyl)benzene in 54 grams of dimethylformamide was then added dropwise in 45 minutes to the reaction flask, where after the mixture was heated further to 80° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a clear viscous liquid. The calculated molecular weight of the theoretical main component was 474.32 Da, chemical structure is shown below.

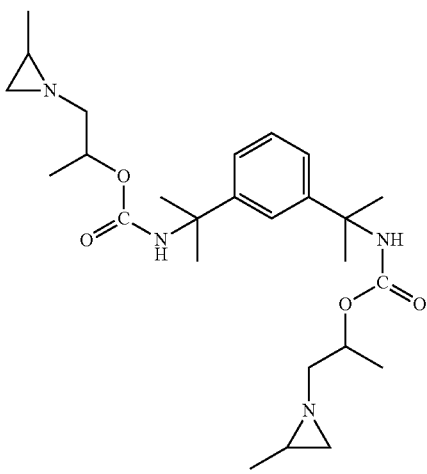 [SMILES: CC(CN1CC1C)OC(=O)NC(C)(C)c1cccc(C(C)(C)NC(=O)OC(C)CN2CC2C)c1]

Molecular weight was confirmed by Maldi-TOF-MS: Calcd. [M+K+]=513.28 Da; Obs. [M+K+]=513.19 Da.

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Comp. Ex. 8 | | | | | | | | | | | |
| 1.2 | 1.7 | 2.3 | 1.4 | 2.3 | 4.8 | 1.1 | 2.1 | 2.1 | 1.3 | 4.2 | 4.9 |

Comparative Example 9

3.00 grams of H12MDI, 27 grams of DMF and 2.61 grams of 1-(2-methylaziridin-1-yl)propan-2-ol were charged to a reaction flask equipped with a thermometer. The mixture was stirred with a mechanical upper stirrer under a nitrogen atmosphere. The mixture was than heated to 50° C., upon reaching this temperature 0.02 grams of Bismuth neodecanoate. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a clear highly viscous liquid. The calculated molecular weight of the theoretical main component was 492.37 Da, chemical structure is shown below.

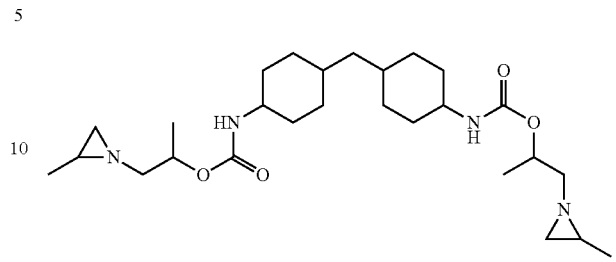

Molecular weight was confirmed by Maldi-TOF-MS: Calcd. [M+Na+]=515.37 Da; Obs. [M+Na+]=515.35 Da.

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Comp. Ex. 9 | | | | | | | | | | | |
| 1.2 | 1.6 | 2.2 | 1.5 | 2.2 | 3.3 | 1.2 | 1.6 | 2.0 | 1.6 | 2.6 | 3.7 |

Example 1

20.0 grams of Desmodur N 3600, 11.98 grams of 1-(2-methylaziridin-1-yl)propan-2-ol and 106 grams of 2-methyltetrahydrofuran were charged to a reaction flask equipped with a thermometer. The mixture was stirred with a mechanical upper stirrer under a nitrogen atmosphere. The mixture was than heated to 50° C., kept at that temperature for 15 minutes and then heated further to 60° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a clear highly viscous liquid. The calculated molecular weight of the theoretical main component was 849.57 Da, chemical structure is shown below.

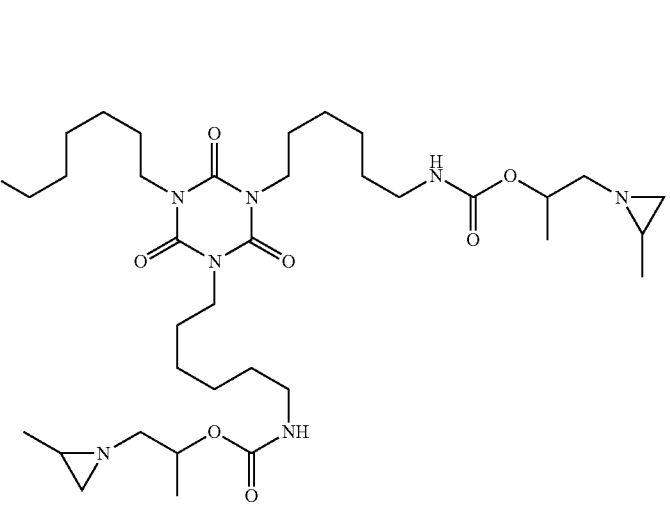

Molecular weight was confirmed by Maldi-TOF-MS: Calcd. [M+Na+]=872.57 Da; Obs. [M+Na+]=872.53 Da. The following components with a mass below 580 Da were determined by LC-MS and quantified:

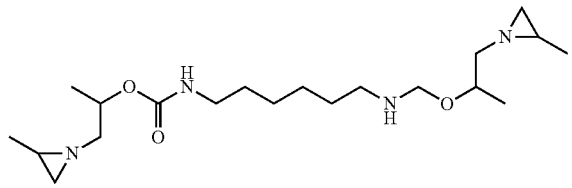

was present in the composition at 0.06 wt. %.

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 1 | 1.2 | 1.3 | 1.3 | 1.2 | 1.2 | 1.4 | 1.2 | 1.3 | 1.2 | 1.2 | 1.1 | 0.9 |

Performance of the synthesized compound as a crosslinker was assessed using spot tests on coating surfaces, based on procedures from the DIN 68861-1 standard. For these tests, 0.41 parts of the composition were mixed with 0.60 parts of Proglyde™ DMM (dipropylene glycol dimethyl ether, mixture of isomers) and incubated at 80° C. for 10 minutes under regular agitation. Subsequently, 0.67 parts of the resulting solution were added to 20 parts of NeoRez® R-1005 under continuous stirring, and the resulting mixture was further stirred for 30 minutes. Afterwards, this coating composition was filtered and applied to Leneta test cards using 100 µm wire rod applicators (Test 1-1). For reference, films were also cast from the same composition lacking a crosslinker (Test 1-2). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 1-1 | 8 | 7 | 7 | 7 |
| Test 1-2 | 1 | 1 | 1 | 1 |

Performance of the synthesized compound as a crosslinker was further assessed using spot tests on coating surfaces with different binder systems.

A waterborne polyurethane binder was synthesized as follows.

A 1 L flask equipped with a thermometer and overhead stirrer was charged with DMPA (13.4 grams), pTHF650 (166.1 grams) and IPDI (156.5 grams). The reaction mixture was placed under $N_2$ atmosphere, heated to 50° C. and 0.03 g of bismuth neodecanoate was added. The mixture was allowed to exotherm and kept at 90° C. for 2.5 hours. The NCO content of the resultant urethane prepolymer was 8.00% on solids (theoretically 8.80%). The prepolymer was cooled down to 75° C. and TEA (9.12 grams) was added and the resulting mixture was stirred for 15 minutes. A dispersion of the resultant prepolymer was made by feeding 320.2 gram of this prepolymer to demineralized water (700 grams) at room temperature in 30 minutes. After the feed was completed, the mixture was stirred for 5 minutes and hydrazine (16% solution in water, 61.6 grams) was added. The dispersion was stirred for a further 1 h.

For further spot tests, 0.35 parts of the crosslinker composition were mixed with 0.07 parts of dipropylene glycol methyl ether and incubated at 80° C. for 10 minutes under regular agitation. Subsequently, the resulting solution was added to 15 parts of the waterborne polyurethane binder described above under continuous stirring, and the resulting mixture was further stirred for 30 minutes. Afterwards, this coating composition was filtered and applied to Leneta test cards using 100 µm wire rod applicators (Test 1-3). For reference, films were also cast from the same composition lacking a crosslinker (Test 1-4). The films were dried for 1 hour at 25° C., then annealed at 50° C. for 16 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 1-3 | — | 10 | — | 10 |
| Test 1-4 | — | 6 | — | 6 |

A waterborne acrylic binder was synthesized as follows.

A 2 L four-necked flask equipped with a thermometer and overhead stirrer was charged with sodium lauryl sulphate (30% solids in water, 18.6 grams of solution) and demineralized water (711 grams). The reactor phase was placed under $N_2$ atmosphere and heated to 82° C. A mixture of demineralized water (112 grams), sodium lauryl sulphate (30% solids in water, 37.2 grams of solution), methyl methacrylate (174.41 grams), n-butyl acrylate (488.44 grams) and methacrylic acid (34.88 grams) was placed in a large feeding funnel and emulsified with an overhead stirrer (monomer feed). Ammonium persulphate (1.75 grams) was dissolved in demineralized water (89.61 grams) and placed in a small feeding funnel (initiator feed). Ammonium persulphate (1.75 grams) was dissolved in demineralized water (10.5 grams), and this solution was added to the reactor phase. Immediately afterwards, 5% by volume of the monomer feed was added to the reactor phase. The reaction mixture then exothermed to 85° C. and was kept at 85° C. for 5 minutes. Then, the residual monomer feed and the initiator feed were fed to the reaction mixture over 90 minutes, maintaining a temperature of 85° C. After completion of the feeds, the monomer feed funnel was rinsed with demineralized water (18.9 grams) and reaction temperature maintained at 85° C. for 45 minutes. Subsequently, the mixture was cooled to room temperature and brought to pH=7.2 with ammonia solution (6.25 wt. % in demineralized water), and brought to 40% solids with further demineralized water.

For further spot tests, 0.89 parts of the crosslinker composition were mixed with 0.18 parts of dipropylene glycol methyl ether and incubated at 80° C. for 10 minutes under regular agitation. Subsequently, the resulting solution was added to 15 parts of the waterborne polyacrylate binder described above under continuous stirring, and the resulting mixture was further stirred for 30 minutes. Afterwards, this coating composition was filtered and applied to Leneta test cards using 100 μm wire rod applicators (Test 1-5). For reference, films were also cast from the same composition lacking a crosslinker (Test 1-6). The films were dried for 1 hour at 25° C., then annealed at 50° C. for 16 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 1-5 | — | 9 | — | 9 |
| Test 1-6 | — | 1 | — | 1 |

A polyester binder was synthesized as follows.

A 2 L reactor equipped with a distillation setup, thermometer and overhead stirrer was charged with 2-methyl-1,3-propane diol (151.9 grams), 1,4-butane diol (152.1 grams), adipic acid (446.3 grams) and dimer fatty acids (371.2 grams). The reaction mixture was heated to 220° C. and water produced from the reaction was removed by distillation. Remaining water was removed under reduced pressure until the acid number of the mixture was less than 40 mg KOH/g. For further spot tests, 42 parts of the polyester binder were mixed with 8.4 parts of methyl ethyl ketone (polyester mixture).

For further spot tests, 1.93 parts of the crosslinker composition were mixed with 0.39 parts of dipropylene glycol methyl ether and incubated at 80° C. for 10 minutes under regular agitation. Subsequently, the resulting solution was added to 25.4 parts of the polyester mixture described above under continuous stirring, and the resulting mixture was further stirred for 30 minutes. Afterwards, this coating composition was filtered and applied to Leneta test cards using 100 μm wire rod applicators (Test 1-7). For reference, films were also cast from the same composition lacking a crosslinker (Test 1-8).

| Ethanol spot test | | | | |
|---|---|---|---|---|
| Sample | 30 min | 60 min | 120 min | 300 min |
| Test 1-7 | — | 8 | — | 8 |
| Test 1-8 | — | 1 | — | 1 |

Example 2

5.93 grams of 1-(2-methylaziridin-1-yl)propan-2-ol, 0.02 grams of bismuth neodecanoate and 40.18 grams of 2-methyltetrahydrofuran were charged to a reaction flask equipped with a thermometer. The mixture was stirred with a mechanical upper stirrer under a nitrogen atmosphere and heated to 50° C. A solution of 10.0 grams of Desmodur N 3900 in 40.18 grams of 2-methyltetrahydrofuran was then added dropwise in 45 minutes to the reaction flask, where after the mixture was heated further to 75° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a yellowish highly viscous liquid. The calculated molecular weight of the theoretical main component was 849.57 Da, chemical structure is shown below.

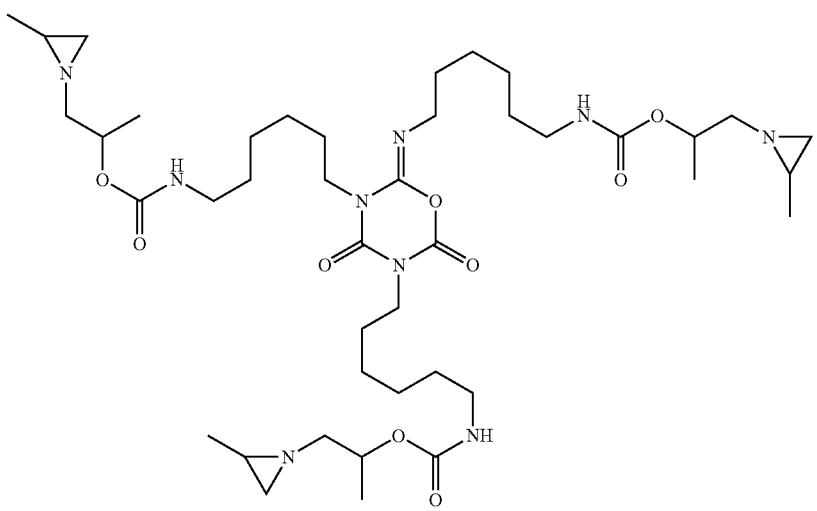 [SMILES: CC(CN1CC1C)OC(=O)NCCCCCC/N=c1\oc(=O)n(CCCCCCNC(=O)OC(C)CN2CC2C)c(=O)n1CCCCCCNC(=O)OC(C)CN1CC1C]

Molecular weight was confirmed by Maldi-TOF-MS: Calcd. [M+Na+]=872.57 Da; Obs. [M+Na+]=872.62 Da. The following components with a mass below 580 Da were determined by LC-MS and quantified:

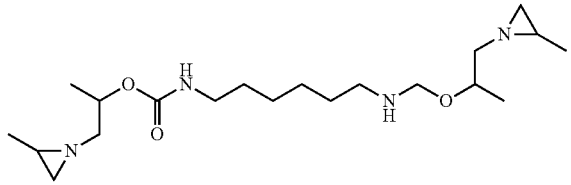

was present in the composition at 1.4 wt. %.

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 2 | 1.1 | 1.1 | 0.9 | 1.1 | 1.0 | 0.9 | 1.0 | — | — | 1.1 | — | — |

Example 3

2.14 grams of 1-(2-methylaziridin-1-yl)propan-2-ol, 2.72 grams of a poly(ethylene glycol) monomethyl ether with an average Mn of 350 Da, 0.02 grams of bismuth neodecanoate and 28 grams of 2-methyltetrahydrofuran were charged to a reaction flask equipped with a thermometer. The mixture was stirred with a mechanical upper stirrer under a nitrogen atmosphere and heated to 50° C. A solution of 5.13 grams of Desmodur N 3600 in 28 grams of 2-methyltetrahydrofuran was then added dropwise in 45 minutes to the reaction flask, where after the mixture was heated further to 70° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a clear highly viscous liquid. The calculated molecular weights of the theoretical main components were 849.57 Da (three aziridines), 1074.68 Da (two aziridines, 7 EG repeating units), 1118.70 Da (two aziridines, 8 EG repeating units) and 1162.73 Da (two aziridines, 9 EG repeating units), chemical structures are shown below.

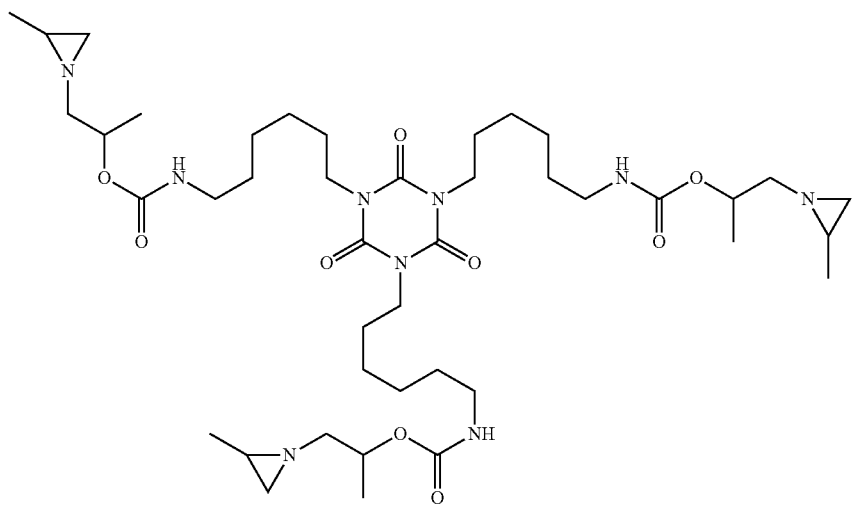

Molecular weight was confirmed by Maldi-TOF-MS:
Calcd. [M+Na+]=872.57 Da; Obs. [M+Na+]=872.53 Da.
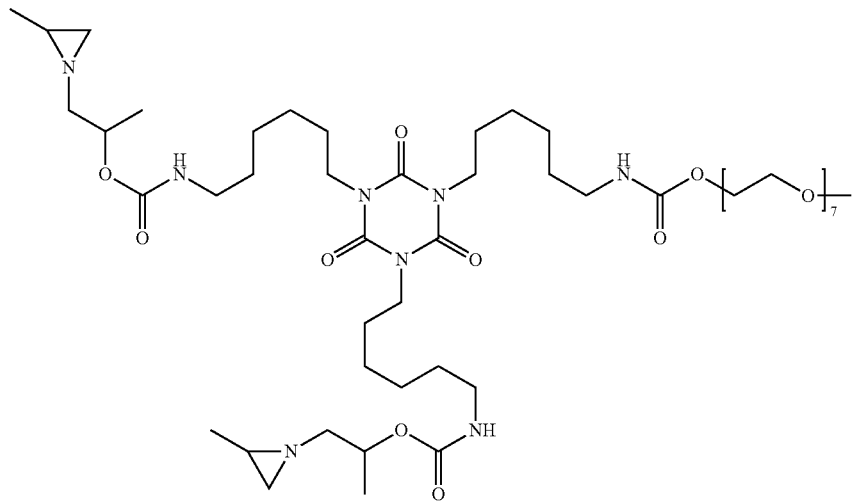
35
Molecular weight was confirmed by Maldi-TOF-MS:
Calcd. [M+Na+]=1097.68 Da; Obs. [M+Na+]=1097.63 Da.
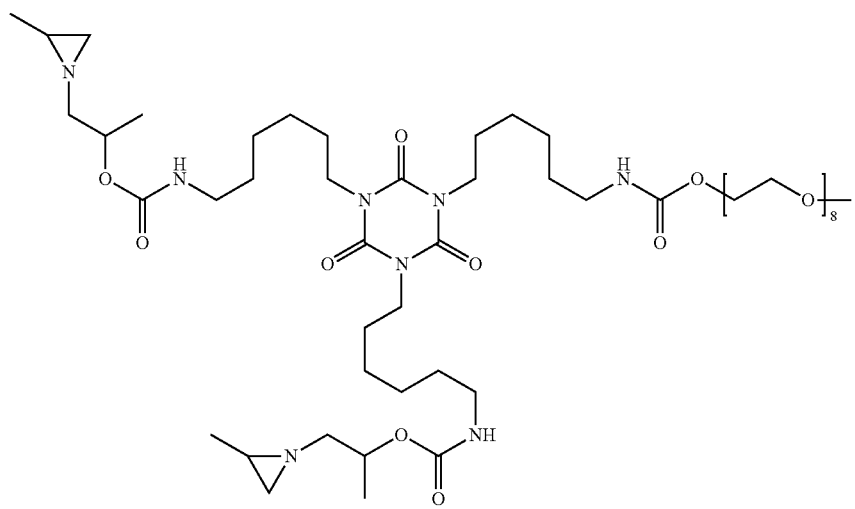

Molecular weight was confirmed by Maldi-TOF-MS: Calcd. [M+Na+]=1141.70 Da; Obs. [M+Na+]=1141.66 Da.

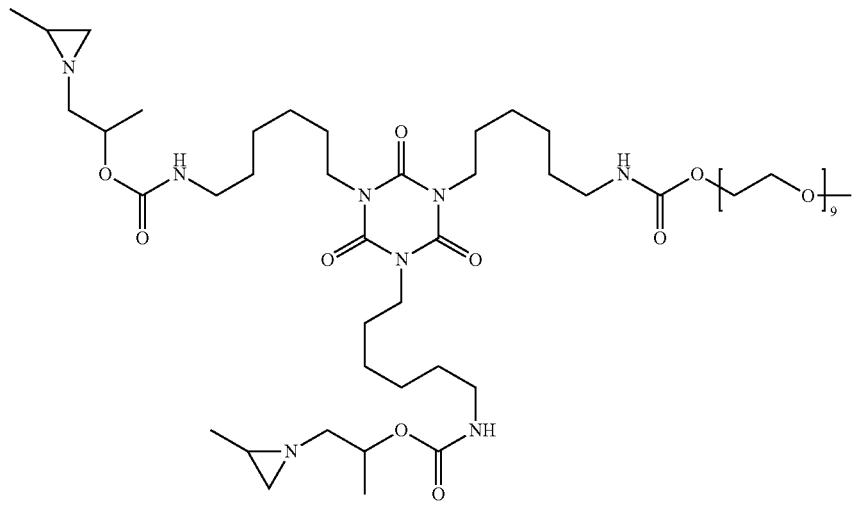

Molecular weight was confirmed by Maldi-TOF-MS: Calcd. [M+Na+]=1185.73 Da; Obs. [M+Na+]=1185.68 Da.

Performance of the synthesized compound as a crosslinker was assessed using spot tests on coating surfaces, based on procedures from the DIN 68861-1 standard. For these tests, 0.71 parts of the composition were mixed with 0.60 parts of Proglyde™ DMM (dipropylene glycol dimethyl ether, mixture of isomers) and incubated at 80° C. for 10 minutes under regular agitation. Subsequently, 0.87 parts of the resulting solution were added to 20 parts of NeoRez® R-1005 under continuous stirring, and the resulting mixture was further stirred for 30 minutes. Afterwards, this coating composition was filtered and applied to Leneta test cards using 100 μm wire rod applicators (Test 3-1). For reference, films were also cast from the same composition lacking a crosslinker (Test 3-2). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 3-1 | 8 | 7 | 6 | 6 |
| Test 3-2 | 1 | 1 | 1 | 1 |

| | Genotoxicity test | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 3 | 1.1 | 1.2 | 1.2 | 1.2 | 1.2 | 1.2 | 1.2 | 1.2 | 1.2 | 1.3 | 1.4 | 1.4 |

Example 4

15.0 grams of Desmodur N 3600, 7.09 grams of 1-(2-methylaziridin-1-yl)propan-2-ol, 8.21 grams of a poly(ethylene glycol) monomethyl ether with an average Mn of 500 Da and 110 grams of 2-methyltetrahydrofuran were charged to a reaction flask equipped with a thermometer. The mixture was stirred with a mechanical upper stirrer under a nitrogen atmosphere. The mixture was then heated to 50° C., kept at that temperature for 15 minutes and then heated further to 60° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a clear highly viscous liquid. The calculated molecular weights of the theoretical main components were 849.57 Da (three aziridines), 1250.78 Da (two aziridines, 11 EG repeating units), 1294.81 Da (two aziridines, 12 EG repeating units) and 1338.84 Da (two aziridines, 13 EG repeating units), chemical structures are shown below.

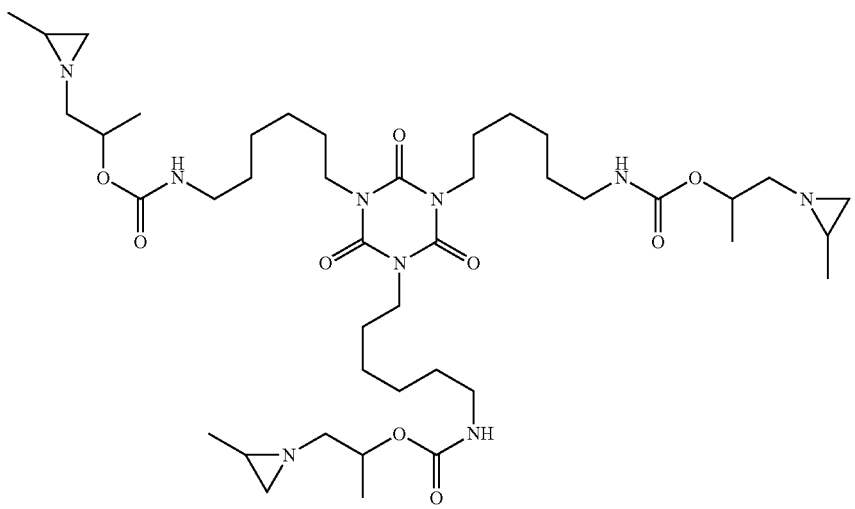
Molecular weight was confirmed by Maldi-TOF-MS:
Calcd. [M+Na+]=872.57 Da; Obs. [M+Na+]=872.54 Da.
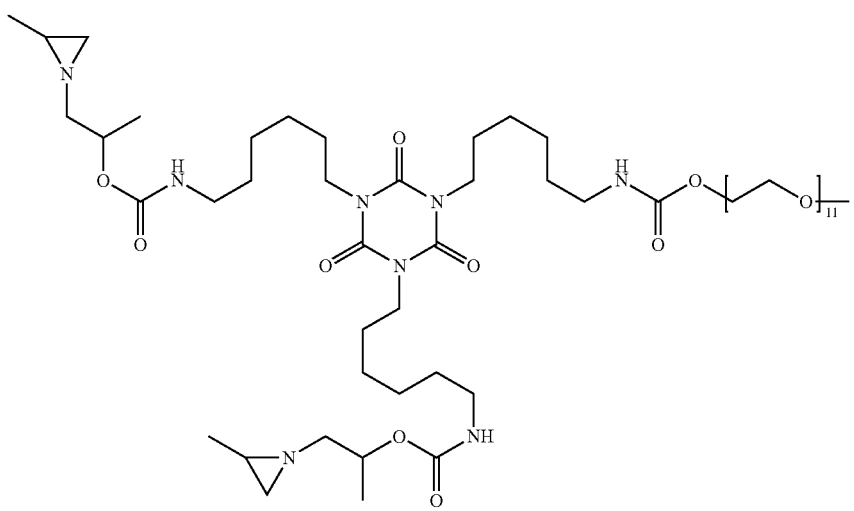

Molecular weight was confirmed by Maldi-TOF-MS:
Calcd. [M+Na+]=1273.78 Da; Obs. [M+Na+]=1273.76 Da.
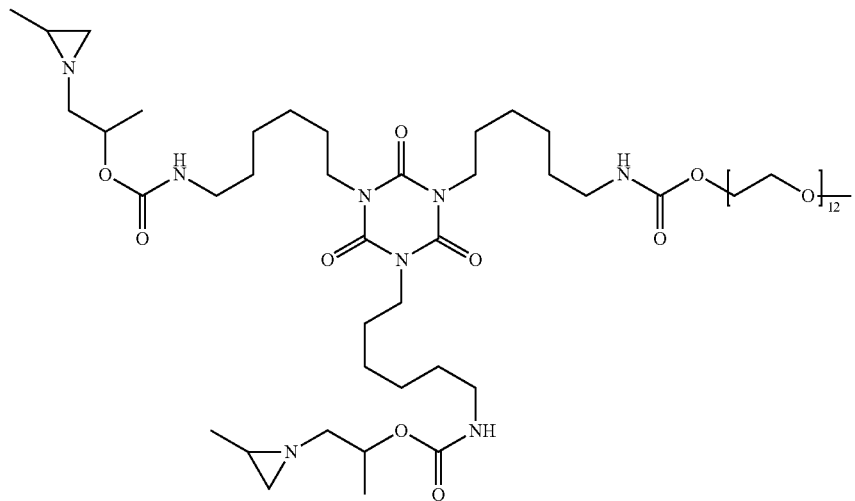
Molecular weight was confirmed by Maldi-TOF-MS:
Calcd. [M+Na+]=1317.81 Da; Obs. [M+Na+]=1317.78 Da.
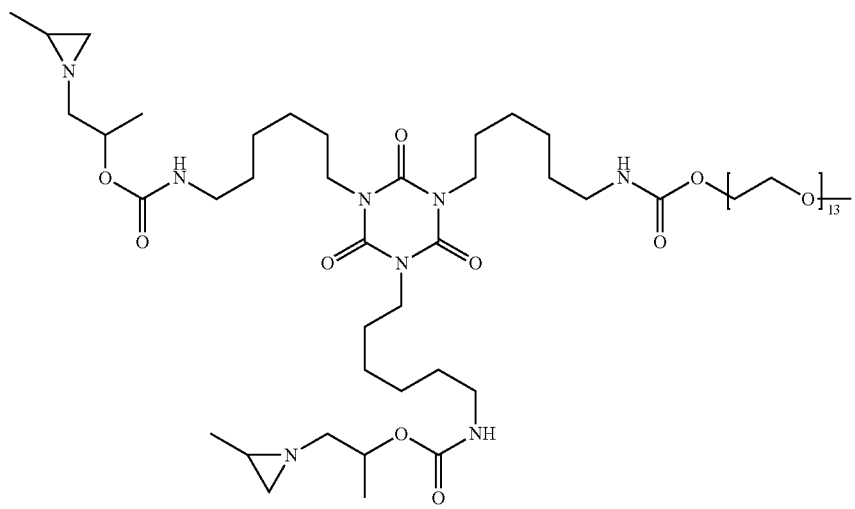

Molecular weight was confirmed by Maldi-TOF-MS: Calcd. [M+Na+]=1361.84 Da; Obs. [M+Na+]=1361.81 Da. The following components with a mass below 580 Da were determined by LC-MS and quantified:

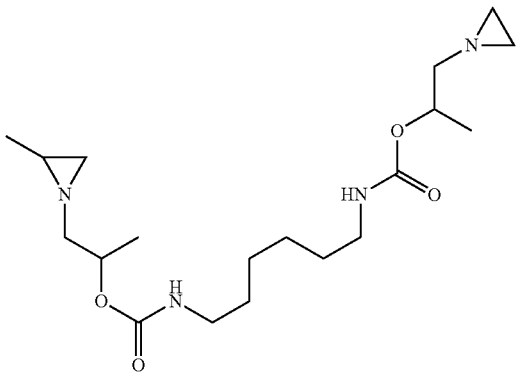 [SMILES: CC(CN1CC1)OC(=O)NCCCCCCNC(=O)OC(C)CN1CC1C]

was present in the composition at 0.26 wt. %.

| | Genotoxicity test | | | |
|---|---|---|---|---|
| | Without S9 rat liver extract | | With S9 rat liver extract | |
| | Bscl 2 | Rtkn | Bscl 2 | Rtkn |
| | concentration | | | |
| | 10  25  50 | 10  25  50 | 10  25  50 | 10  25  50 |
| Ex. 4 | 1.1  1.3  1.5 | 1.1  1.2  1.3 | 1.3  1.3  1.4 | 1.0  1.1  1.1 |

Performance of the synthesized compound as a crosslinker was assessed using spot tests on coating surfaces, based on procedures from the DIN 68861-1 standard. For these tests, 0.66 parts of the composition were mixed with 0.60 parts of Proglyde™ DMM (dipropylene glycol dimethyl ether, mixture of isomers) and incubated at 80° C. for 10 minutes under regular agitation. Subsequently, 0.84 parts of the resulting solution were added to 21 parts of NeoRez® R-1005 under continuous stirring, and the resulting mixture was further stirred for 30 minutes. Afterwards, this coating composition was filtered and applied to Leneta test cards using 100 μm wire rod applicators (Test 4-1). For reference, films were also cast from the same composition lacking a crosslinker (Test 4-2). The films were dried for 16 hours at 25'C, then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 4-1 | 8 | 7 | 7 | 6 |
| Test 4-2 | 1 | 1 | 1 | 1 |

Performance of the synthesized compound as a crosslinker was further assessed using spot tests on coating surfaces with different binder systems.

For further spot tests, 0.55 parts of the crosslinker composition were mixed with 0.11 parts of dipropylene glycol methyl ether and incubated at 80° C. for 10 minutes under regular agitation. Subsequently, the resulting solution was added to 15 parts of the waterborne polyurethane binder prepared as described in Example 1 under continuous stirring, and the resulting mixture was further stirred for 30 minutes. Afterwards, this coating composition was filtered and applied to Leneta test cards using 100 μm wire rod applicators (Test 4-3). For reference, films were also cast from the same composition lacking a crosslinker (Test 4-4). The films were dried for 1 hour at 25° C., then annealed at 50° C. for 16 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 4-3 | — | 10 | — | 10 |
| Test 4-4 | — | 6 | — | 6 |

For further spot tests, 1.41 parts of the crosslinker composition were mixed with 0.28 parts of dipropylene glycol methyl ether and incubated at 80° C. for 10 minutes under regular agitation. Subsequently, the resulting solution was added to 15 parts of the waterborne polyacrylate binder prepared as described in Example 1 under continuous stirring, and the resulting mixture was further stirred for 30 minutes. Afterwards, this coating composition was filtered and applied to Leneta test cards using 100 μm wire rod applicators (Test 4-5). For reference, films were also cast from the same composition lacking a crosslinker (Test 4-6). The films were dried for 1 hour at 25° C., then annealed at 50° C. for 16 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 4-5 | — | 9 | — | 8 |
| Test 4-6 | — | 1 | — | 1 |

In another test, 3.07 parts of the crosslinker composition were mixed with 0.61 parts of dipropylene glycol methyl ether and incubated at 80° C. for 10 minutes under regular agitation. Subsequently, the resulting solution was added to 25.4 parts of the polyester mixture prepared as described in Example 1 above under continuous stirring, and the resulting mixture was further stirred for 30 minutes. Afterwards, this coating composition was filtered and applied to Leneta test cards using 100 μm wire rod applicators (Test 4-7). For reference, films were also cast from the same composition lacking a crosslinker (Test 4-8).

All films were dried for 1 hour at 25° C., then annealed at 50° C. for 16 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 4-7 | — | 4 | — | 4 |
| Test 4-8 | — | 1 | — | 1 |

Example 5

15.0 grams of Desmodur N 3600, 7.09 grams of 1-(2-methylaziridin-1-yl)propan-2-ol, 8.21 grams of a poly(ethylene glycol) monomethyl ether with an average Mn of 1000 Da, 112 grams of dimethylformamide were charged to a reaction flask equipped with a thermometer. The mixture was stirred with a mechanical upper stirrer under a nitrogen atmosphere. The mixture was than heated to 50° C., 0.03 grams of dibutyltin dilaureate was added and after 15 minutes the mixture was heated further to 70° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain an opaque highly viscous liquid. The calculated molecular weights of the theoretical main components were 849.57 Da (three aziridines) and 1735.07 Da (two aziridines, 22 EG repeating units), chemical structures are shown below.

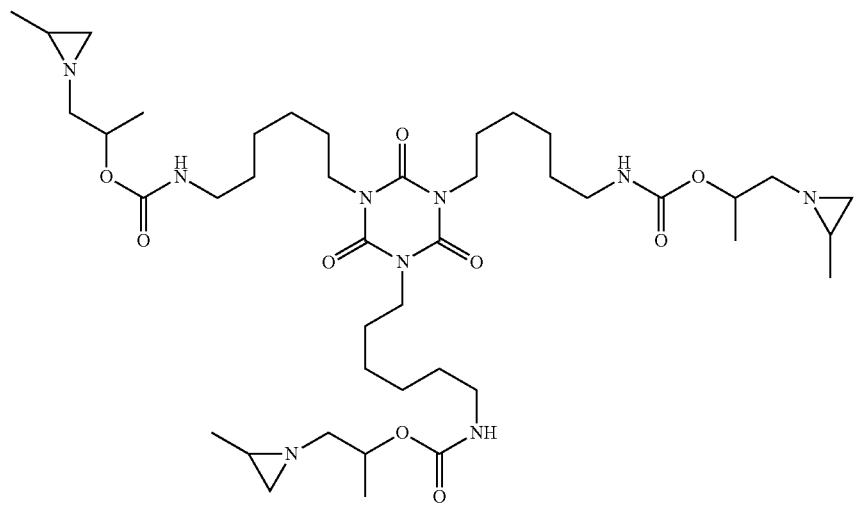

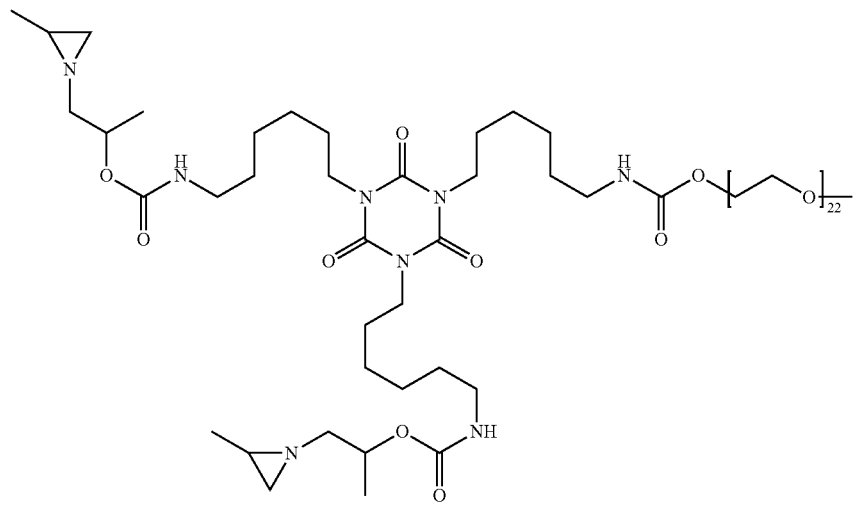

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Ex. 5 1.1 | 1.1 | 1.2 | 1.1 | 1.3 | 1.3 | 1.1 | 1.2 | 1.1 | 1.2 | 1.1 | 0.9 |

Example 6

6.00 grams of Desmodur N 3600 and 89 grams of 2-methyltetrahydrofuran were charged to a reaction flask equipped with a thermometer. The mixture was stirred with a mechanical upper stirrer under a nitrogen atmosphere. The mixture was then heated to 50° C., upon reaching this temperature 2.84 grams of 1-(2-methylaziridin-1-yl)propan-2-ol, 13.14 grams of a poly(ethylene glycol) monomethyl ether with an average Mn of 2000 Da and 0.02 grams of bismuth neodecanoate were charged to the reaction flask, and then heated further to 60° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a white solid wax. The calculated molecular weights of the theoretical main components were 849.57 Da (three aziridines) and 2747.67 Da (two aziridines, 45 EG repeating units), chemical structures are shown below.

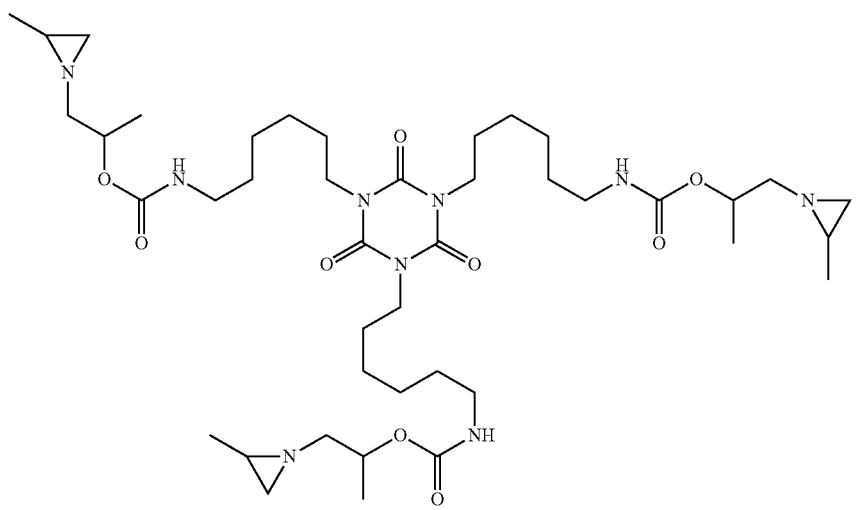

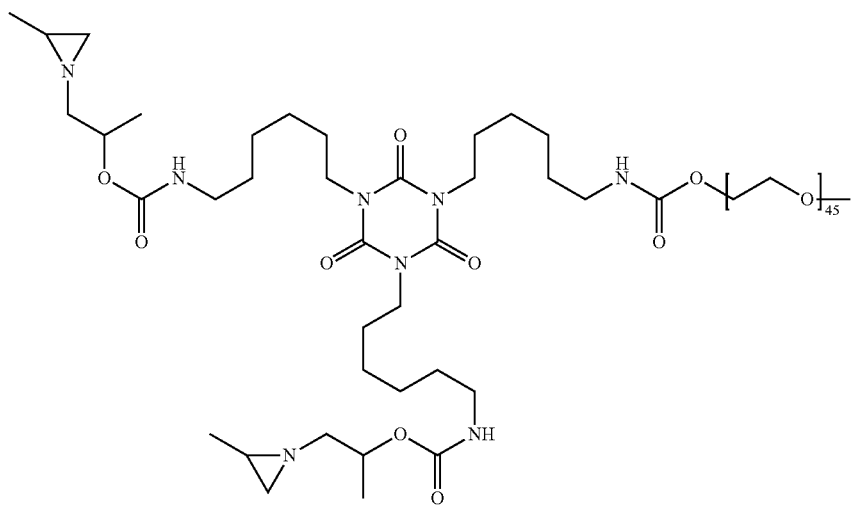

Performance of the synthesized compound as a crosslinker was assessed using spot tests on coating surfaces, based on procedures from the DIN 68861-1 standard. For these tests, 1.22 parts of the composition were mixed with 0.60 parts of Proglyde™ DMM (dipropylene glycol dimethyl ether, mixture of isomers) and incubated at 80° C. for 10 minutes under regular agitation. Subsequently, 1.21 parts of the resulting solution were added to 21 parts of NeoRez® R-1005 under continuous stirring, and the resulting mixture was further stirred for 30 minutes. Afterwards, this coating composition was filtered and applied to Leneta test cards using 100 μm wire rod applicators (Test 6-1). For reference, films were also cast from the same composition lacking a crosslinker (Test 6-2). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 6-1 | 7 | 6 | 6 | 6 |
| Test 6-2 | 1 | 1 | 1 | 1 |

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 6 | 1.3 | 1.4 | 1.4 | 1.3 | 1.7 | 1.6 | 1.1 | 1.3 | 1.2 | 1.5 | 1.3 | 1.1 |

Example 7

A 10 mL reaction vial was placed under a $N_2$ atmosphere, charged with propylene imine (2.28 gram), 1,2-epoxybutane (3.40 gram), capped, heated to 55° C., after which the mixture was stirred for 4 days at T=55° C. The excess of PI was removed in vacuo, followed by further purification via vacuum distillation, resulting in a colorless low viscous liquid.

1.62 grams of Desmodur N 3600, 0.02 grams of bismuth neodecanoate and 8.20 grams of dimethylformamide were charged to a reaction flask equipped with a thermometer. The mixture was stirred with a mechanical upper stirrer under a nitrogen atmosphere and heated to 50° C. A solution of 1.04 grams of the product from the first step in 8.20 grams of dimethylformamide was then added dropwise in 15 minutes to the reaction flask, a further 8.20 grams of dimethylformamide was flushed through the feeding funnel into the reaction mixture, whereafter the mixture was heated further to 80° C. Samples were taken at regular intervals and the reaction progress was monitored using a Bruker Alpha FT-IR spectrometer until no change in NCO-stretch at 2200-2300 $cm^{-1}$ was observed. Subsequently, 0.05 grams of 1-butanol were added to the mixture, followed by further reaction to complete disappearance of aforementioned NCO-stretch peak. Evaporation of the solvent in vacuo to 30% solids yielded a clear liquid. The calculated molecular weight of the theoretical main component was 891.62 Da, chemical structure is shown below.

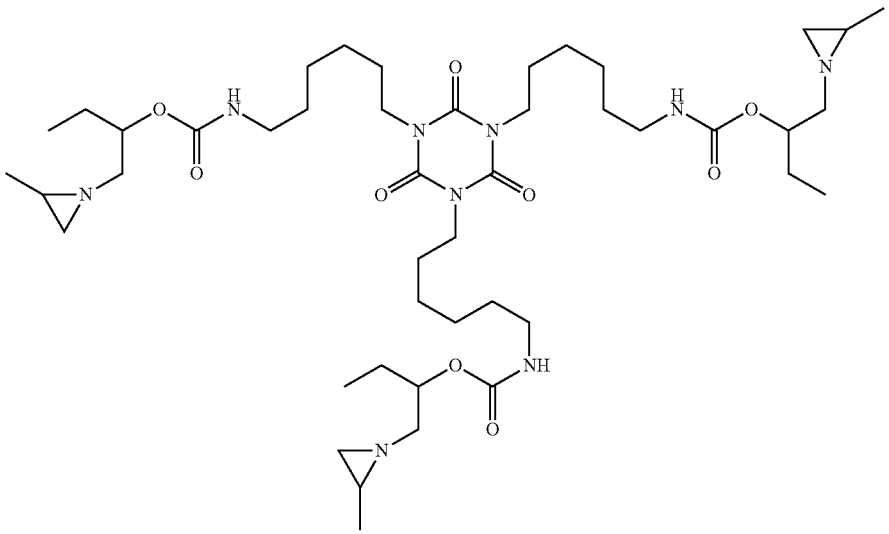

Molecular weight was confirmed by Maldi-TOF-MS: Calcd. [M+Na+]=914.62 Da; Obs. [M+Na+]=914.66 Da. The following components with a mass below 580 Da were determined by LC-MS and quantified:

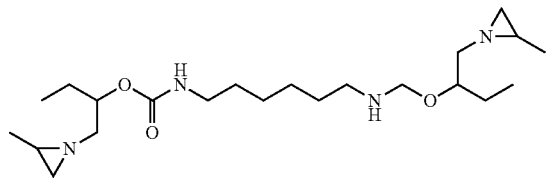

was present in the composition at 0.09 wt. %.

Performance of the synthesized compound as a crosslinker was assessed using spot tests on coating surfaces, based on procedures from the DIN 68861-1 standard. For these tests, 1.56 parts of the composition (i.e. at 30% solids in dimethylformamide) was added to 15 parts of NeoRez® R-1005 under continuous stirring, and the resulting mixture was further stirred for 30 minutes. Afterwards, this coating composition was filtered and applied to Leneta test cards using 100 μm wire rod applicators (Test 7-1). For reference, films were also cast from the same composition lacking a crosslinker (Test 7-2). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 7-1 | — | 8 | — | 6 |
| Test 7-2 | — | 1 | — | 1 |

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Ex. 7 1.1 | 1.1 | — | 1.1 | 1.3 | — | 1.1 | 1.3 | 1.5 | 1.1 | 1.3 | 1.5 |

Example 8

A 20 mL reaction vial was charged with propylene imine (2.95 gram), trans-2,3-epoxybutane (3.75 gram) and $K_2CO_3$ (1.0 g), capped, heated to 55° C., after which the mixture was stirred for 11 days at T=55° C. After filtration the excess of PI was removed in vacuo, followed by further purification via vacuum distillation, resulting in a colorless low viscous liquid.

0.96 grams of Desmodur N 3600, 0.02 grams of bismuth neodecanoate and 4.90 grams of dimethylformamide were charged to a reaction flask equipped with a thermometer. The mixture was stirred with a mechanical upper stirrer under a nitrogen atmosphere and heated to 50° C. A solution of 0.62 grams of the product from the first step in 4.90 grams of dimethylformamide was then added dropwise in 15 minutes to the reaction flask, a further 4.90 grams of dimethylformamide was flushed through the feeding funnel into the reaction mixture, whereafter the mixture was heated further to 80° C. Samples were taken at regular intervals and the reaction progress was monitored using a Bruker Alpha FT-IR spectrometer until no change in NCO-stretch at 2200-2300 $cm^{-1}$ was observed. Subsequently, 0.03 grams of 1-butanol were added to the mixture, followed by further reaction to complete disappearance of aforementioned NCO-stretch peak. Evaporation of the solvent in vacuo to 45% solids yielded a low viscosity pinkish liquid. The calculated molecular weight of the theoretical main component was 891.62 Da, chemical structure is shown below.

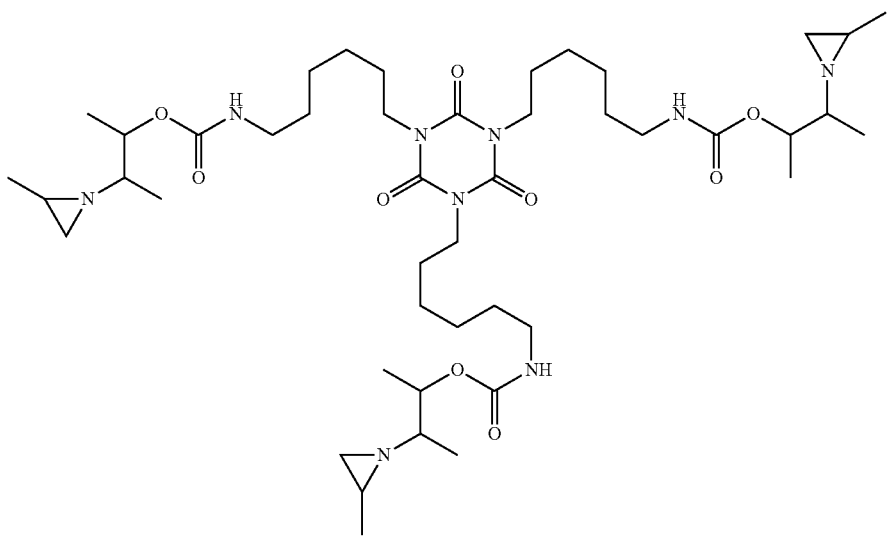

Performance of the synthesized compound as a crosslinker was assessed using spot tests on coating surfaces, based on procedures from the DIN 68861-1 standard. For these tests, 1.01 parts of the composition (i.e. at 45% solids in dimethylformamide) was added to 15 parts of NeoRez® R-1005 under continuous stirring, and the resulting mixture was further stirred for 30 minutes. Afterwards, this coating composition was filtered and applied to Leneta test cards using 100 μm wire rod applicators (Test 8-1). For reference, films were also cast from the same composition lacking a crosslinker (Test 8-2). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 8-1 | — | 7 | — | 6 |
| Test 8-2 | — | 1 | — | 1 |

| | Genotoxicity test | | | | | | | | | | |
|---|---|---|---|---|---|---|---|---|---|---|---|
| | Without S9 rat liver extract | | | | | | With S9 rat liver extract | | | | |
| | Bscl 2 | | | Rtkn | | | Bscl 2 | | | Rtkn | |
| | concentration | | | | | | | | | | |
| | 10 | 25 | 50 | 10 | 25 | 50 | 10 | 25 | 50 | 10 | 25 | 50 |
| Ex. 8 | 1.1 | 1.3 | 1.6 | 1.2 | 1.4 | 1.4 | 1.1 | 1.4 | 1.4 | 1.3 | 1.5 | 1.3 |

Example 9

A reaction vial was charged with propylene imine (3.53 gram), allyl glycidyl ether (5.07 gram) and K$_2$CO$_3$ (0.5 g), capped and heated to 80° C., after which the mixture was stirred for 20 h at T=80° C. After filtration the excess of PI was removed in vacuo, followed by further purification via vacuum distillation, resulting in a colorless low viscous liquid.

4.0 grams of Desmodur N 3600, 0.02 grams of bismuth neodecanoate and 7.50 grams of dimethylformamide were charged to a reaction flask equipped with a thermometer. The mixture was stirred with a mechanical upper stirrer under a nitrogen atmosphere and heated to 50° C. A solution of 3.41 grams of the product from the first step in 7.50 grams of dimethylformamide was then added dropwise in 10 minutes to the reaction flask, a further 7.50 grams of dimethylformamide was flushed through the feeding funnel into the reaction mixture, whereafter the mixture was heated further to 80° C. Samples were taken at regular intervals and the reaction progress was monitored using a Bruker Alpha FT-IR spectrometer until no change in NCO-stretch at 2200-2300 cm$^{-1}$ was observed. Subsequently, 0.13 grams of 1-butanol were added to the mixture, followed by further reaction to complete disappearance of aforementioned NCO-stretch peak. The resulting solution was a clear liquid. The calculated molecular weight of the theoretical main component was 1017.65 Da chemical structure is shown below.

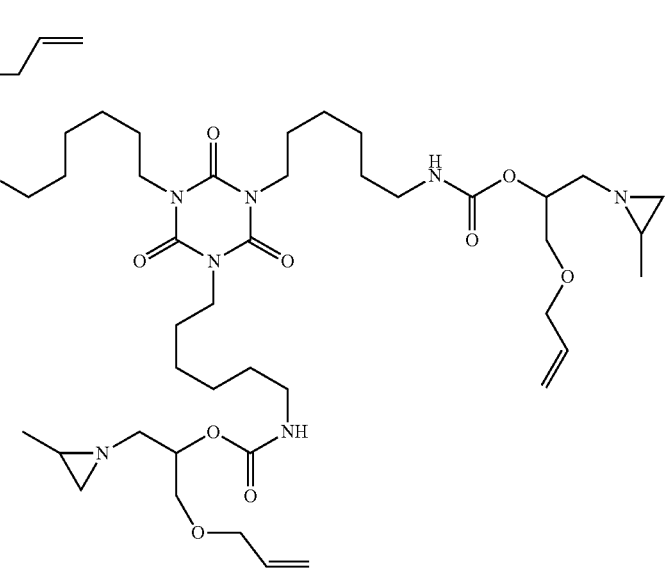

Molecular weight was confirmed by Maldi-TOF-MS: Calcd. [M+Na+]=1040.64 Da; Obs. [M+Na+]=1040.75 Da. The following components with a mass below 580 Da were determined by LC-MS and quantified:

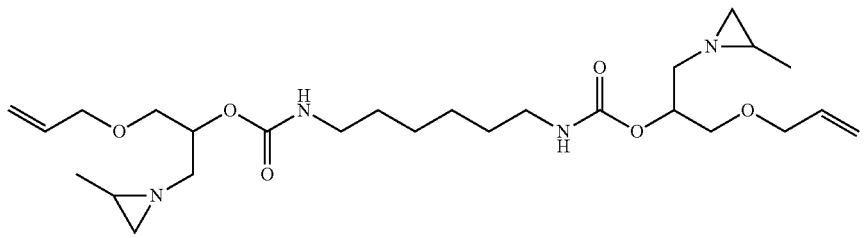 [SMILES: C=CCOCC(CN1CC1C)OC(=O)NCCCCCCNC(=O)OC(COCC=C)CN1CC1C]

was present in the composition at 0.098 wt. % and

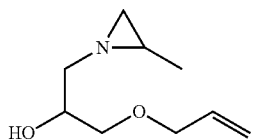

was present in the composition at less than 0.01 wt. %.

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 9 | 1.1 | 1.2 | 1.2 | 1.0 | 1.1 | 1.1 | 1.2 | 1.2 | 1.2 | 1.1 | 1.1 | 1.2 |

Example 10

A 1 L round bottom flask equipped with a condensor was placed under a N₂ atmosphere and charged with propylene imine (80.0 gram), n-butyl glycidyl ether (126.0 gram) and K₂CO₃ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

46.54 grams of the resulting material (1-butoxy-3-(2-methylaziridin-1-yl)propan-2-ol) and 28.63 grams of 1-(2-methylaziridin-1-yl)propan-2-ol were charged to a reaction flask equipped with a thermometer, together with 0.02 grams of bismuth neodecanoate and 32.54 grams of 2-methyltetrahydrofuran. The mixture was stirred with a mechanical upper stirrer under a nitrogen atmosphere and heated to 50° C. A solution of 100 grams of Desmodur N 3600 in 32.54 grams of 2-methyltetrahydrofuran was then added dropwise in 45 minutes to the reaction flask, a further 10 grams of 2-methyltetrahydrofuran was flushed through the feeding funnel into the reaction mixture, whereafter the mixture was heated further to 70° C. Samples were taken at regular intervals and the reaction progress was monitored using a Bruker Alpha FT-IR spectrometer until no NCO-stretch at 2200-2300 cm⁻¹ was observed. The solvent was removed in vacuo to obtain a yellowish highly viscous liquid. The calculated molecular weights of the theoretical main components were 849.57 Da (three methyl side groups), 921.63 Da (two methyl side groups, one butoxymethyl side group), 993.68 Da (one methyl side group, two butoxymethyl side groups) and 1065.74 Da (three butoxymethyl side groups), chemical structures are shown below.

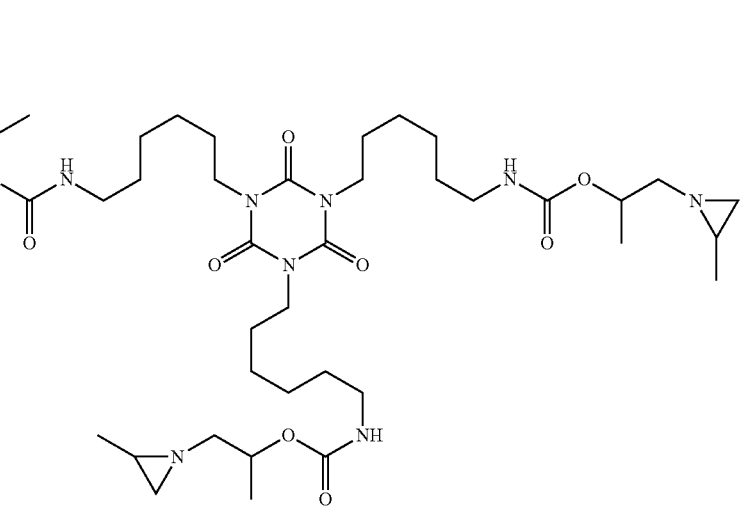

Molecular weight was confirmed by Maldi-TOF-MS:
Calcd. [M+Na+]=872.57 Da; Obs. [M+Na+]=872.59 Da.
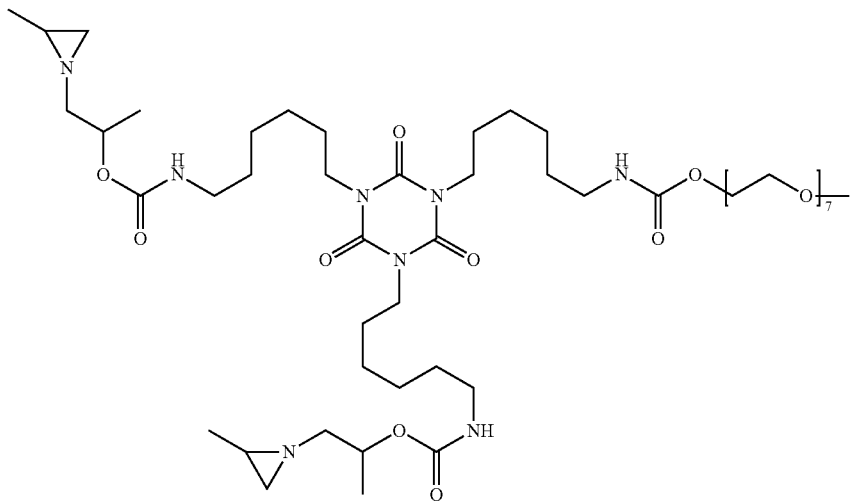
Molecular weight was confirmed by Maldi-TOF-MS:
Calcd. [M+Na+]=944.63 Da; Obs. [M+Na+]=944.66 Da.
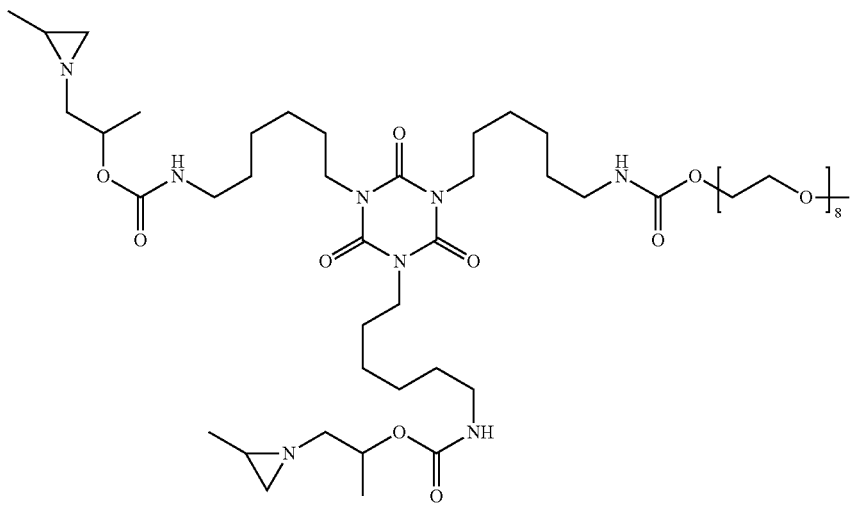

Molecular weight was confirmed by Maldi-TOF-MS: Calcd. [M+Na+]=1016.68 Da; Obs. [M+Na+]=1016.72 Da.

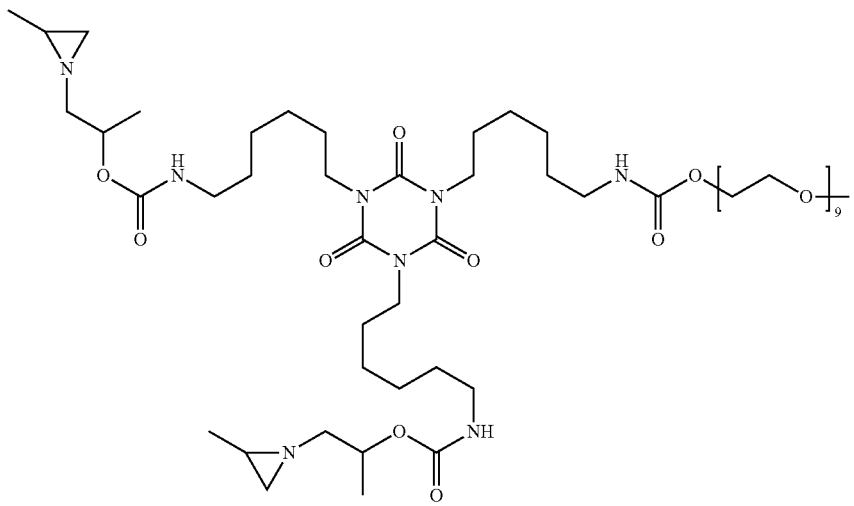

Molecular weight was confirmed by Maldi-TOF-MS: Calcd. [M+Na+]=1088.74 Da; Obs. [M+Na+]=1088.79 Da.

Performance of the synthesized compound as a crosslinker was assessed using spot tests on coating surfaces, based on procedures from the DIN 68861-1 standard. For these tests, 0.74 parts of the composition were mixed with 0.74 parts of 1-methoxy-2-propyl acetate and incubated at 80° C. for 10 minutes under regular agitation. Subsequently, the resulting solution was added to 15 parts of NeoRez® R-1005 under continuous stirring, and the resulting mixture was further stirred for 30 minutes. Afterwards, this coating composition was filtered and applied to Leneta test cards using 100 μm wire rod applicators (Test 10-1). For reference, films were also cast from the same composition lacking a crosslinker (Test 10-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 10-1 | — | 9 | — | 8 |
| Test 10-2 | — | 1 | — | 1 |

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Ex. 10 | | | | | | | | | | | |
| 1.1 | 1.3 | 1.1 | 0.9 | 0.9 | 0.8 | 1.1 | 1.2 | 1.3 | 1.0 | 1.0 | 1.0 |

Comparative Example 10

A 1 L round bottom flask equipped with a condensor was placed under a $N_2$ atmosphere and charged with propylene imine (80.0 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

20.9 grams of the resulting material (1-butoxy-3-(2-methylaziridin-1-yl)propan-2-ol) was charged to a reaction flask equipped with a thermometer, together with 0.02 grams of bismuth neodecanoate. The mixture was stirred with a mechanical upper stirrer under a nitrogen atmosphere and heated to 50° C. 10.0 grams of HDI was then added dropwise in 30 minutes to the reaction flask, whereafter the mixture was heated further to 80° C. Samples were taken at regular intervals and the reaction progress was monitored using a Bruker Alpha FT-IR spectrometer. After 3 hours, 0.25 g 1-butanol was added to the reaction mixture and the mixture was stirred at 80° C. for 1 hour. After cooling down to room temperature a yellowish highly viscous liquid was obtained. The calculated molecular weight of the theoretical main component was 542.40 Da, chemical structure is shown below.

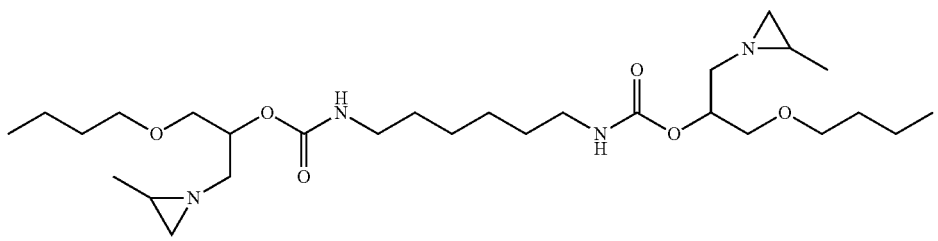 [SMILES: CCCCOCC(CN1CC1C)OC(=O)NCCCCCCNC(=O)OC(COCCCC)CN1CC1C]

Molecular weight was confirmed by Maldi-TOF-MS: Calcd. [M+Na+]=565.40 Da; Obs. [M+Na+]=565.49 Da.

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Comp. Ex. 10 1.3 | 1.5 | 1.6 | 1.2 | 1.9 | 1.9 | 1.3 | 1.5 | 1.5 | 1.5 | 2.3 | 2.2 |

Comparative Example 11

A 1 L round bottom flask equipped with a condenser was placed under a N₂ atmosphere and charged with propylene imine (80.0 gram), n-butyl glycidyl ether (126.0 gram) and K₂CO₃ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

20.2 grams of the resulting material (1-butoxy-3-(2-methylaziridin-1-yl)propan-2-ol) was charged to a reaction flask equipped with a thermometer, together with 0.02 grams of bismuth neodecanoate. The mixture was stirred with a mechanical upper stirrer under a nitrogen atmosphere and heated to 50° C. 10.0 grams of HDI was then added dropwise in 30 minutes to the reaction flask, whereafter the mixture was heated further to 80° C. Samples were taken at regular intervals and the reaction progress was monitored using a Bruker Alpha FT-IR spectrometer until no NCO-stretch at 2200-2300 cm⁻¹ was observed. After cooling down to room temperature an opaque solid was obtained. The calculated molecular weight of the theoretical main component was 548.36 Da, chemical structure is shown below.

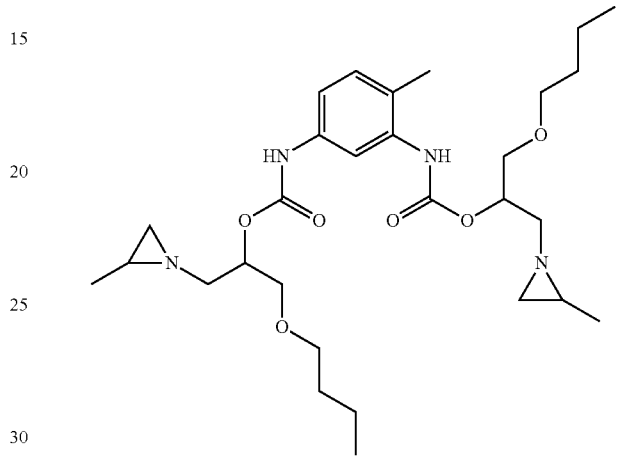

Molecular weight was confirmed by Maldi-TOF-MS: Calcd. [M+Na+]=571.36 Da; Obs. [M+Na+]=571.42 Da.

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Comp. Ex. 11 1.2 | 1.6 | 1.9 | 1.3 | 2.1 | 2.3 | 1.3 | 1.7 | 1.6 | 1.2 | 2.1 | 2.5 |

Example 11

A 1 L round bottom flask equipped with a condenser was placed under a N₂ atmosphere and charged with propylene imine (80.0 gram), n-butyl glycidyl ether (126.0 gram) and K₂CO₃ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

8.72 grams of the resulting material (1-butoxy-3-(2-methylaziridin-1-yl)propan-2-ol) was charged to a reaction flask equipped with a thermometer, together with 0.02 grams of bismuth neodecanoate and 24.85 grams of 2-methyltetrahydrofuran. The mixture was stirred with a mechanical upper stirrer under a nitrogen atmosphere and heated to 50° C. A solution of 6.0 grams of 1,3-bis(1-isocyanato-1-methylethyl)benzene in 24.85 grams of 2-methyltetrahydrofuran was then added dropwise in 45 minutes to the reaction flask, whereafter the mixture was heated further to 80° C. Samples were taken at regular intervals and the reaction progress was monitored using a Bruker Alpha FT-IR spectrometer until no change in NCO-stretch at 2200-2300 cm$^{-1}$ was observed. Subsequently, 0.18 grams of 1-butanol were added to the mixture, followed by further reaction to complete disappearance of aforementioned NCO-stretch peak. The solvent was removed in vacuo to obtain a dark yellowish highly viscous translucent liquid. The calculated molecular weight of the theoretical main component was 618.44 Da, chemical structure is shown below.

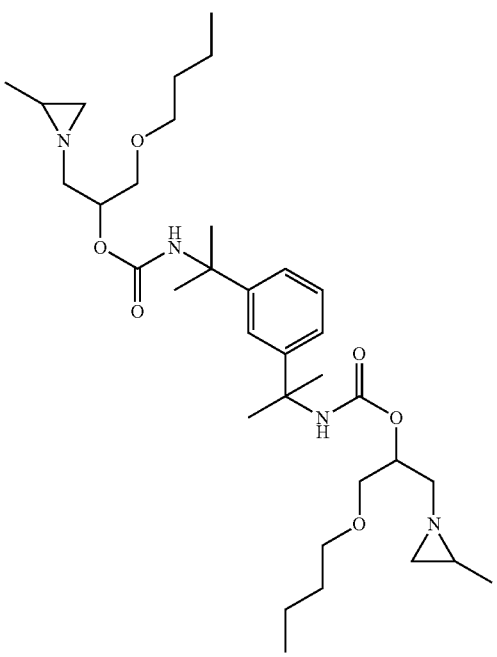

Molecular weight was confirmed by Maldi-TOF-MS: Calcd. [M+Na+]=641.44 Da; Obs. [M+Na+]=641.44 Da. The following components with a mass below 580 Da were determined by LC-MS and quantified:

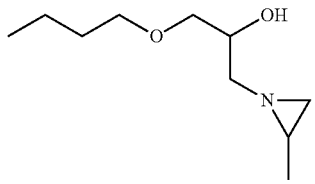

was present in the composition at 0.2 wt. %.

Performance of the synthesized compound as a crosslinker was assessed using spot tests on coating surfaces, based on procedures from the DIN 68861-1 standard. For these tests, 0.16 parts of the composition were mixed with 0.16 parts of 1-methoxy-2-propyl acetate and incubated at 80° C. for 10 minutes under regular agitation. Subsequently, the resulting solution was added to 5 parts of NeoRez® R-1005 under continuous stirring, and the resulting mixture was further stirred for 30 minutes. Afterwards, this coating composition was filtered and applied to Leneta test cards using 100 μm wire rod applicators (Test 11-1). For reference, films were also cast from the same composition lacking a crosslinker (Test 11-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 11-1 | — | 6 | — | 5 |
| Test 11-2 | — | 1 | — | 1 |

| | Genotoxicity test | | | |
|---|---|---|---|---|
| | Without S9 rat liver extract | | With S9 rat liver extract | |
| | Bscl 2 | Rtkn | Bscl 2 | Rtkn |
| | concentration | | | |
| | 10  25  50 | 10  25  50 | 10  25  50 | 10  25  50 |
| Ex. 11 | 1.1  1.3  1.3 | 1.1  1.3  1.3 | 1.2  1.3  1.3 | 1.3  1.3  1.1 |

Example 12

A 1 L round bottom flask equipped with a condensor was placed under a N$_2$ atmosphere and charged with propylene imine (80.0 gram), n-butyl glycidyl ether (126.0 gram) and K$_2$CO$_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

8.12 grams of the resulting material (1-butoxy-3-(2-methylaziridin-1-yl)propan-2-ol) was charged to a reaction flask equipped with a thermometer, together with 0.02 grams of bismuth neodecanoate and 23.62 grams of 2-methyltetrahydrofuran. The mixture was stirred with a mechanical upper stirrer under a nitrogen atmosphere and heated to 50° C. A solution of 6.0 grams of 4,4'-methylenebis(cyclohexyl isocyanate) in 23.62 grams of 2-methyltetrahydrofuran was then added dropwise in 45 minutes to the reaction flask, whereafter the mixture was heated further to 80° C. Samples were taken at regular intervals and the reaction progress was monitored using a Bruker Alpha FT-IR spectrometer until no change in NCO-stretch at 2200-2300 cm$^{-1}$ was observed. Subsequently, 0.17 grams of 1-butanol were added to the mixture, followed by further reaction to complete disappearance of aforementioned NCO-stretch peak. The solvent was removed in vacuo to obtain a yellowish highly viscous translucent liquid. The calculated molecular weight of the theoretical main component was 636.48 Da, chemical structure is shown below.

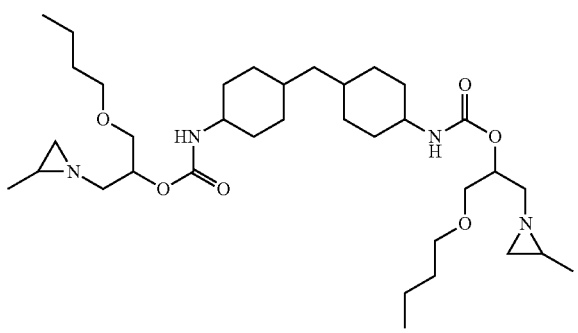

Molecular weight was confirmed by Maldi-TOF-MS: Calcd. [M+Na+]=659.48 Da; Obs. [M+Na+]=659.47 Da. The following components with a mass below 580 Da were determined by LC-MS and quantified:

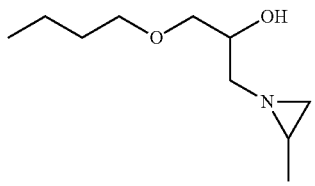

was present in the composition at 0.04 wt. %.

Performance of the synthesized compound as a crosslinker was assessed using spot tests on coating surfaces, based on procedures from the DIN 68861-1 standard. For these tests, 0.16 parts of the composition were mixed with 0.16 parts of 1-methoxy-2-propyl acetate and incubated at 80° C. for 10 minutes under regular agitation. Subsequently, the resulting solution was added to 5 parts of NeoRez® R-1005 under continuous stirring, and the resulting mixture was further stirred for 30 minutes. Afterwards, this coating composition was filtered and applied to Leneta test cards using 100 µm wire rod applicators (Test 12-1). For reference, films were also cast from the same composition lacking a crosslinker (Test 12-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 12-1 | — | 8 | — | 7 |
| Test 12-2 | — | 1 | — | 1 |

| Genotoxicity test | | | | | | | | | | | |
|---|---|---|---|---|---|---|---|---|---|---|---|
| | Without S9 rat liver extract | | | | | | With S9 rat liver extract | | | | |
| | Bscl 2 | | | Rtkn | | | Bscl 2 | | | Rtkn | |
| | concentration | | | | | | | | | | |
| | 10 | 25 | 50 | 10 | 25 | 50 | 10 | 25 | 50 | 10 | 25 | 50 |
| Ex. 12 | 1.0 | 1.0 | 1.0 | 1.0 | 1.0 | 1.0 | 1.1 | 1.0 | 1.0 | 1.0 | 1.0 | 1.1 |

Example 13

A 1 L round bottom flask equipped with a condensor was placed under a $N_2$ atmosphere and charged with propylene imine (80.0 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

20 grams of Desmodur N 3400 and 0.02 grams of bismuth neodecanoate were charged to a reaction flask equipped with a thermometer. The mixture was stirred with a mechanical upper stirrer under a nitrogen atmosphere and heated to 50° C. 17.88 grams of the product from the first step was then added dropwise in 10 minutes to the reaction flask, whereafter the mixture was heated further to 70° C. Samples were taken at regular intervals and the reaction progress was monitored using a Bruker Alpha FT-IR spectrometer until no change in NCO-stretch at 2200-2300 $cm^{-1}$ was observed. Subsequently, 0.16 grams of 1-butanol were added to the mixture, followed by further reaction to complete disappearance of aforementioned NCO-stretch peak. The product was a yellowish highly viscous liquid. The calculated molecular weight of the theoretical main component was 710.49 Da, chemical structure is shown below.

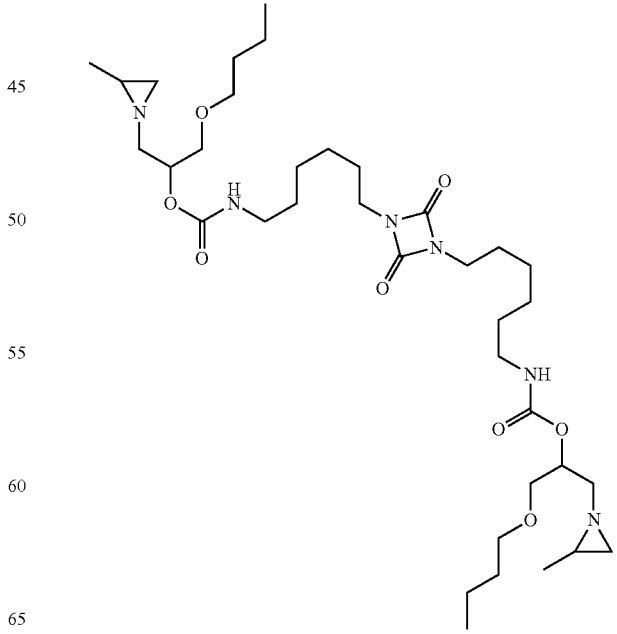

Molecular weight was confirmed by Maldi-TOF-MS: Calcd. [M+Na+]=733.49 Da; Obs. [M+Na+]=733.57 Da. The following components with a mass below 580 Da were determined by LC-MS and quantified:

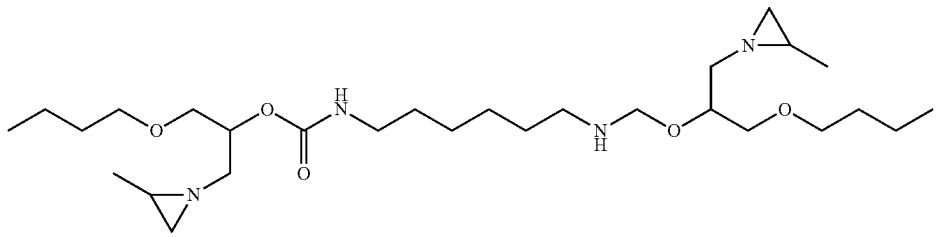 [SMILES: CCCCOCC(CN1CC1C)OCNCCCCCCNC(=O)OC(COCCCC)CN1CC1C]

was present in the composition at 0.2 wt. % and

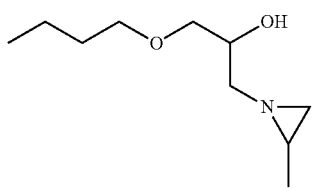

was present at less than 0.01 wt. %.

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Ex. 13 1.1 | 1.3 | — | 1.1 | 1.2 | — | 1.2 | 1.2 | — | 1.4 | 1.6 | — |

Example 14

A 1 L round bottom flask equipped with a condensor was placed under a $N_2$ atmosphere and charged with propylene imine (80.0 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

1.92 grams of the resulting material (1-butoxy-3-(2-methylaziridin-1-yl)propan-2-ol) was charged to a reaction flask equipped with a thermometer, together with 0.02 grams of bismuth neodecanoate and 19 grams of dimethylformamide. The mixture was stirred with a mechanical upper stirrer under a nitrogen atmosphere and heated to 50° C. A solution of 2.00 grams of Desmodur N 3600 in 19 grams of dimethylformamide was then added dropwise in 45 minutes to the reaction flask, whereafter the mixture was heated further to 70° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a clear, yellowish highly viscous liquid. The calculated molecular weight of the theoretical main component was 1065.74 Da, chemical structure is shown below.

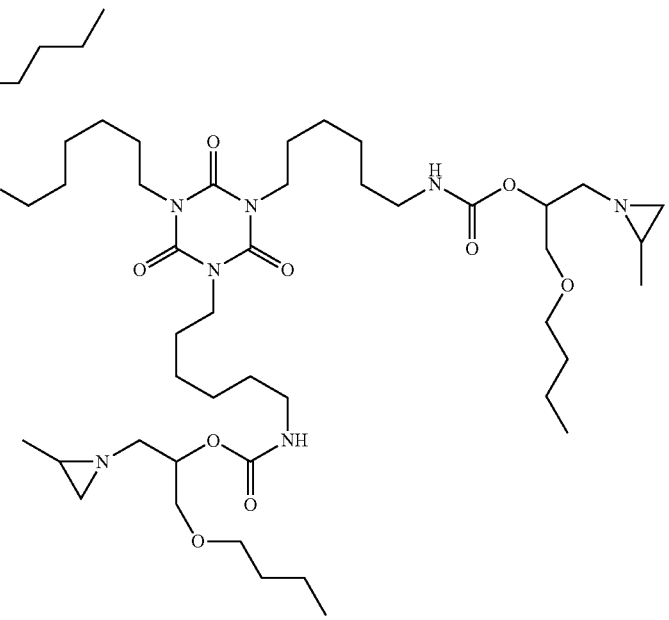

Molecular weight was confirmed by Maldi-TOF-MS: Calcd. [M+Na+]=1088.74 Da; Obs. [M+Na+]=1088.76 Da. The following components with a mass below 580 Da were determined by LC-MS and quantified:

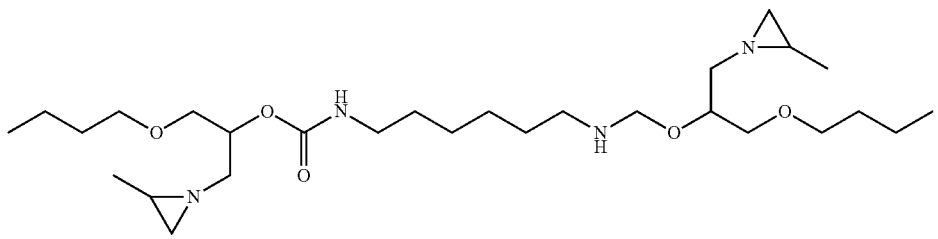 [SMILES: CCCCOCC(CN1CC1C)OCNCCCCCCNC(=O)OC(COCCCC)CN1CC1C]

was present in the composition at 0.36 wt. % and

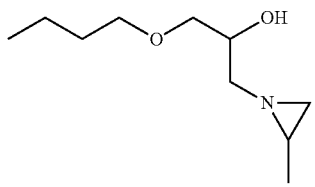

was present at less than 0.01 wt. %.

Performance of the synthesized compound as a cross-linker was assessed using spot tests on coating surfaces, based on procedures from the DIN 68861-1 standard. For these tests, 0.58 parts of the composition were mixed with 0.60 parts of Proglyde™ DMM (dipropylene glycol dimethyl ether, mixture of isomers) and incubated at 80° C. for 10 minutes under regular agitation. Subsequently, 0.79 parts of the resulting solution were added to 20 parts of NeoRez® R-1005 under continuous stirring, and the resulting mixture was further stirred for 30 minutes. Afterwards, this coating composition was filtered and applied to Leneta test cards using 100 μm wire rod applicators (Test 14-1). For reference, films were also cast from the same composition lacking a crosslinker (Test 14-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 14-1 | 8 | 8 | 8 | 7 |
| Test 14-2 | 1 | 1 | 1 | 1 |

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Ex. 14 | | | | | | | | | | | |
| 1.1 | 1.1 | 1.1 | 0.8 | 0.8 | 0.6 | 1.0 | 1.0 | 1 | 0.9 | 0.9 | 0.8 0.6 |

Example 15

A 1 L round bottom flask equipped with a condensor was placed under a $N_2$ atmosphere and charged with propylene imine (80.0 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

26.98 grams of the resulting material (1-butoxy-3-(2-methylaziridin-1-yl)propan-2-ol) was charged to a reaction flask equipped with a thermometer, together with 0.02 grams of bismuth neodecanoate and 6.79 grams of 2-methyltetrahydrofuran. The mixture was stirred with a mechanical upper stirrer under a nitrogen atmosphere and heated to 50° C. A solution of 28.00 grams of Desmodur N 3900 in 6.79 grams of 2-methyltetrahydrofuran was then added dropwise in 45 minutes to the reaction flask, a further 10 grams of 2-methyltetrahydrofuran was flushed through the feeding funnel into the reaction mixture, whereafter the mixture was heated further to 70° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a clear, yellowish highly viscous liquid. The calculated molecular weight of the theoretical main component was 1065.74 Da, chemical structure is shown below.

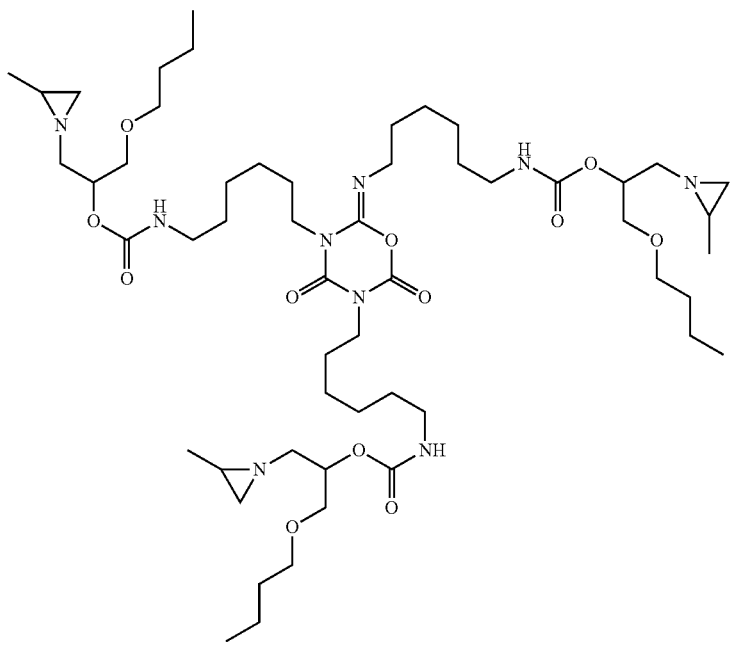 [SMILES: CCCCOCC(CN1CC1C)OC(=O)NCCCCCC/N=c1\oc(=O)n(CCCCCCNC(=O)OC(COCCCC)CN2CC2C)c(=O)n1CCCCCCNC(=O)OC(COCCCC)CN1CC1C]

Molecular weight was confirmed by Maldi-TOF-MS: Calcd. [M+Na+]=1088.74 Da; Obs. [M+Na+]=1088.81 Da. The following components with a mass below 580 Da were determined by LC-MS and quantified:

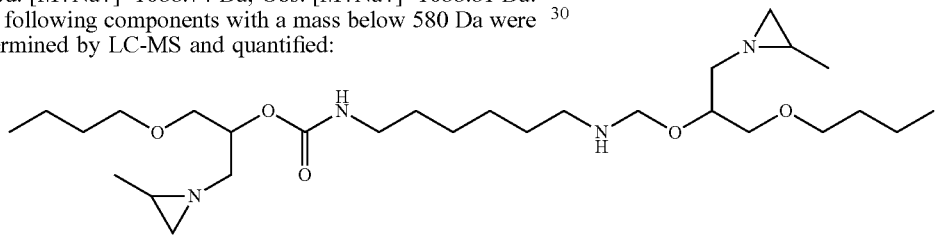

was present in the composition at 0.30 wt. % and

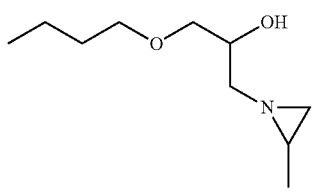

was present at 0.02 wt. %.

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 15 | 1.1 | 1.1 | 0.9 | 1.1 | 1.0 | 0.9 | 1.0 | — | — | 1.1 | — | — |

Example 16

A 1 L round bottom flask equipped with a condensor was placed under a $N_2$ atmosphere and charged with propylene imine (80.0 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

20 grams of Desmodur XP 2860 and 0.02 grams of bismuth neodecanoate were charged to a reaction flask equipped with a thermometer. The mixture was stirred with a mechanical upper stirrer under a nitrogen atmosphere and heated to 50° C. 16.40 grams of the product from the first step was then added dropwise in 10 minutes to the reaction flask, whereafter the mixture was heated further to 70° C. Samples were taken at regular intervals and the reaction progress was monitored using a Bruker Alpha FT-IR spectrometer until no change in NCO-stretch at 2200-2300 $cm^{-1}$ was observed. Subsequently, 0.16 grams of 1-butanol were added to the mixture, followed by further reaction to complete disappearance of aforementioned NCO-stretch peak. The product was a yellowish translucent highly viscous liquid. The calculated molecular weights of the theoretical main components were 770.55 Da (propyl side group), 784.57 Da (butyl side group) and 798.58 Da (pentyl side group), chemical structures are shown below.
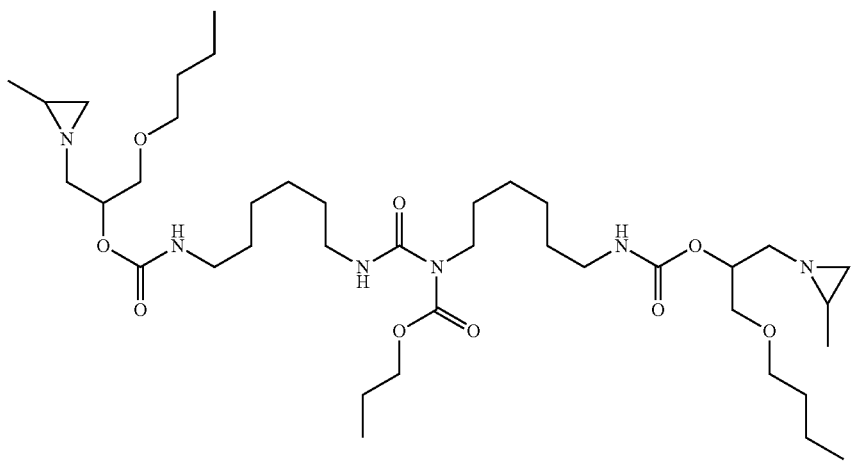 [SMILES: CCCCOCC(CN1CC1C)OC(=O)NCCCCCCNC(=O)N(CCCCCCNC(=O)OC(COCCCC)CN1CC1C)C(=O)OCCC]
Molecular weight was confirmed by Maldi-TOF-MS: Calcd. [M+Na+]=793.55 Da; Obs. [M+Na+]=793.57 Da.
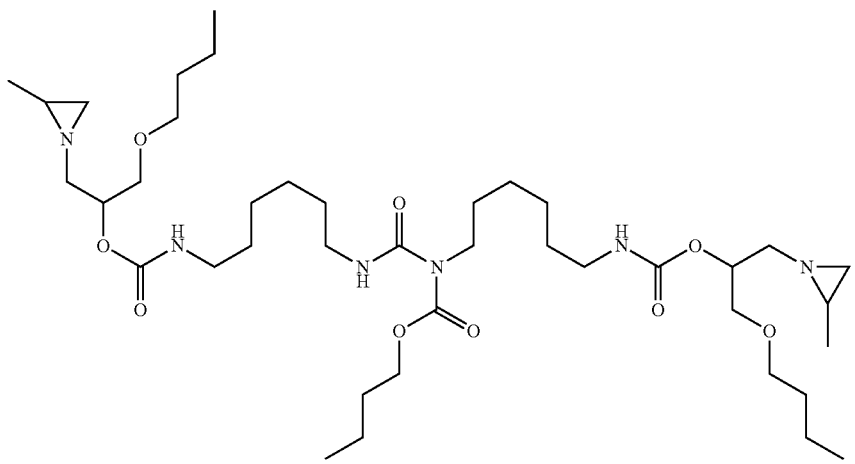 [SMILES: CCCCOCC(CN1CC1C)OC(=O)NCCCCCCNC(=O)N(CCCCCCNC(=O)OC(COCCCC)CN1CC1C)C(=O)OCCCC]
Molecular weight was confirmed by Maldi-TOF-MS: Calcd. [M+Na+]=807.57 Da; Obs. [M+Na+]=807.61 Da.

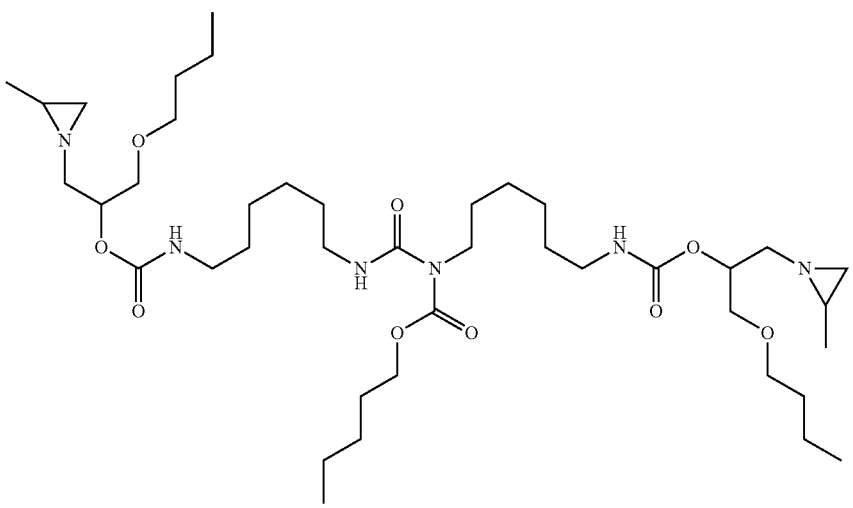 [SMILES: CCCCCOC(=O)N(CCCCCCNC(=O)OC(COCCCC)CN1CC1C)C(=O)NCCCCCCNC(=O)OC(COCCCC)CN1CC1C]

Molecular weight was confirmed by Maldi-TOF-MS: Calcd. [M+Na+]=821.58 Da; Obs. [M+Na+]=821.63 Da. The following components with a mass below 580 Da were determined by LC-MS and quantified:

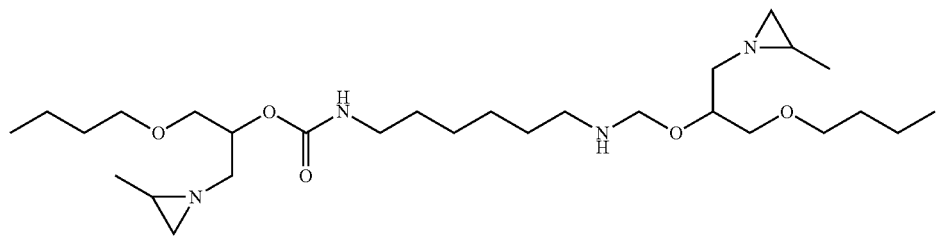 [SMILES: CCCCOCC(CN1CC1C)OCNCCCCCCNC(=O)OC(COCCCC)CN1CC1C]

was present in the composition at 0.66 wt. % and

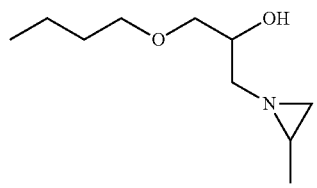

was present at 0.14 wt. %.

Performance of the synthesized compound as a crosslinker was assessed using spot tests on coating surfaces, based on procedures from the DIN 68861-1 standard. For these tests, 0.62 parts of the composition were mixed with 0.62 parts of 1-methoxy-2-propyl acetate and incubated at 80° C. for 10 minutes under regular agitation. Subsequently, the resulting solution was added to 15 parts of NeoRez® R-1005 under continuous stirring, and the resulting mixture was further stirred for 30 minutes. Afterwards, this coating composition was filtered and applied to Leneta test cards using 100 μm wire rod applicators (Test 16-1). For reference, films were also cast from the same composition lacking a crosslinker (Test 16-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 16-1 | — | 7 | — | 6 |
| Test 16-2 | — | 1 | — | 1 |

| | Genotoxicity test | | | | | | | | | | |
|---|---|---|---|---|---|---|---|---|---|---|---|
| | Without S9 rat liver extract | | | | | | With S9 rat liver extract | | | | |
| | Bscl 2 | | | Rtkn | | | Bscl 2 | | | Rtkn | |
| | concentration | | | | | | | | | | |
| | 10 | 25 | 50 | 10 | 25 | 50 | 10 | 25 | 50 | 10 | 25 | 50 |
| Ex. 16 | 1.1 | 1.2 | 1.6 | 1.1 | 1.2 | 1.3 | 1.1 | 1.2 | 1.3 | 1.1 | 1.2 | 1.3 |

Example 17

A 1 L round bottom flask equipped with a condensor was placed under a $N_2$ atmosphere and charged with propylene imine (80.0 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid. 18.21 grams of the resulting material (1-butoxy-3-(2-methylaziridin-1-yl)propan-2-ol) and 9.45 grams of a poly(ethylene glycol) monomethyl ether with an average Mn of 350 Da were charged to a reaction flask equipped with a thermometer, together with 0.02 grams of bismuth neodecanoate and 6.29 grams of 2-methyltetrahydrofuran.

The mixture was stirred with a mechanical upper stirrer under a nitrogen atmosphere and heated to 50° C. A solution of 25.0 grams of Desmodur N 3600 in 6.29 grams of 2-methyltetrahydrofuran was then added dropwise in 25 minutes to the reaction flask, a further 10 grams of 2-methyltetrahydrofuran was flushed through the feeding funnel into the reaction mixture, whereafter the mixture was heated further to 70° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a highly viscous yellowish translucent liquid. The calculated molecular weights of the theoretical main components were 1065.74 Da (three aziridines), 1218.79 Da (two aziridines, 7 EG repeating units), 1262.82 Da (two aziridines, 8 EG repeating units) and 1306.85 Da (two aziridines, 9 EG repeating units), chemical structures are shown below.

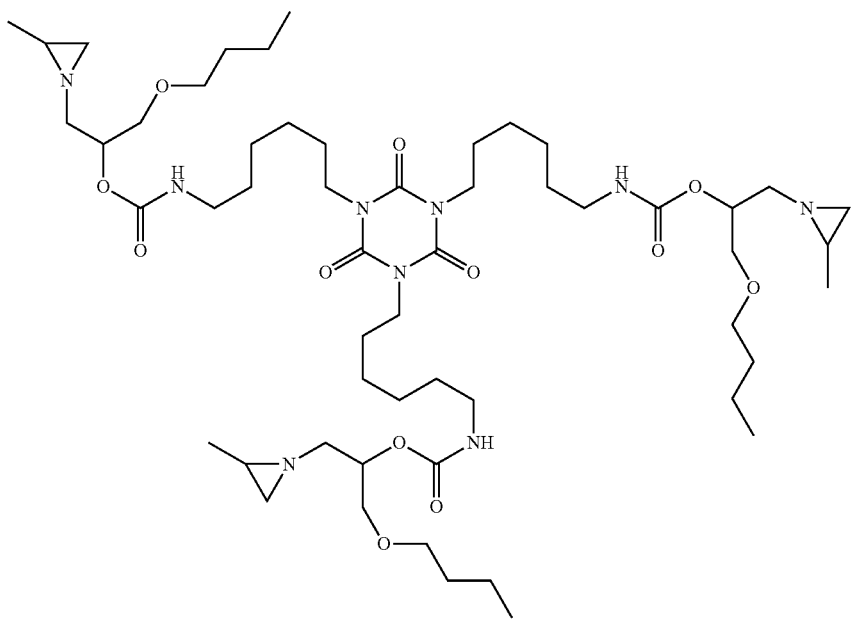

Molecular weight was confirmed by Maldi-TOF-MS:
Calcd. [M+Na+]=1088.74 Da; Obs. [M+Na+]=1088.90 Da.
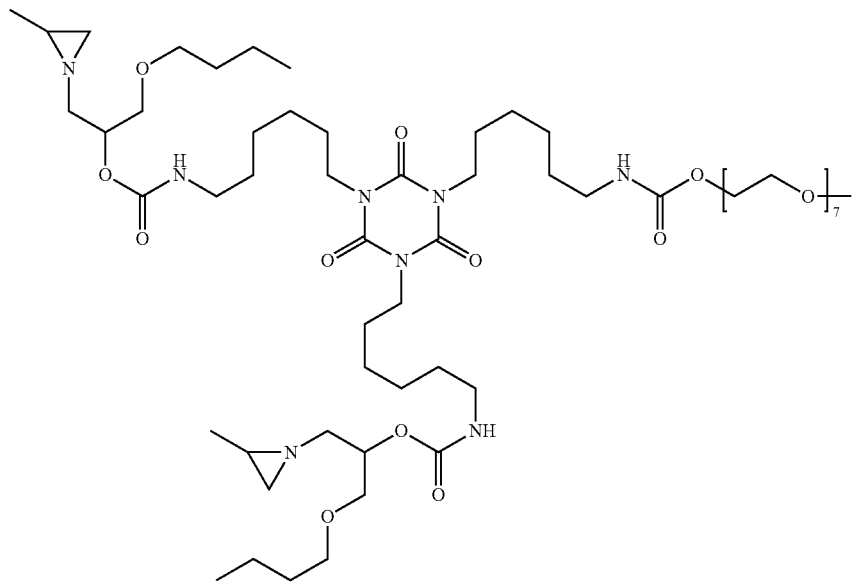
Molecular weight was confirmed by Maldi-TOF-MS:
Calcd. [M+Na+]=1241.79 Da; Obs. [M+Na+]=1241.96 Da.
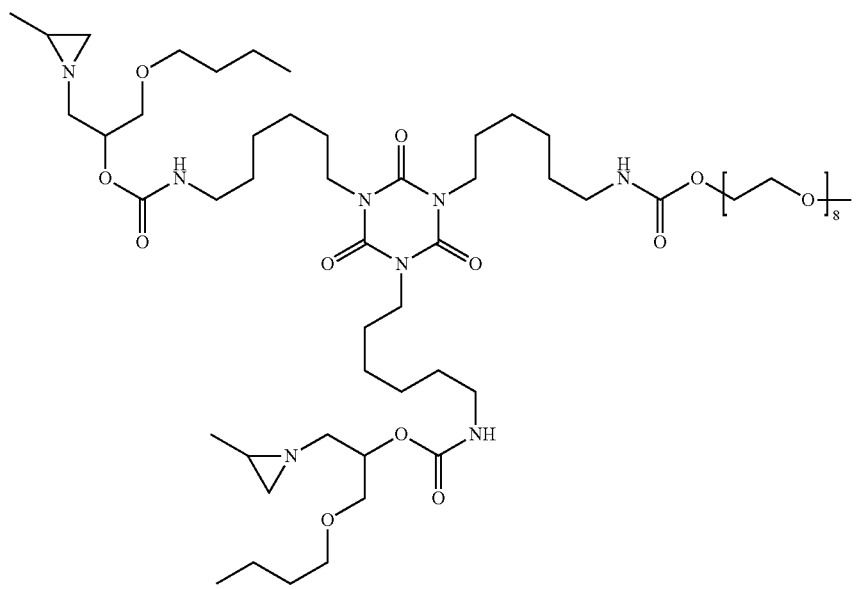

Molecular weight was confirmed by Maldi-TOF-MS: Calcd. [M+Na+]=1285.82 Da; Obs. [M+Na+]=1286.00 Da.

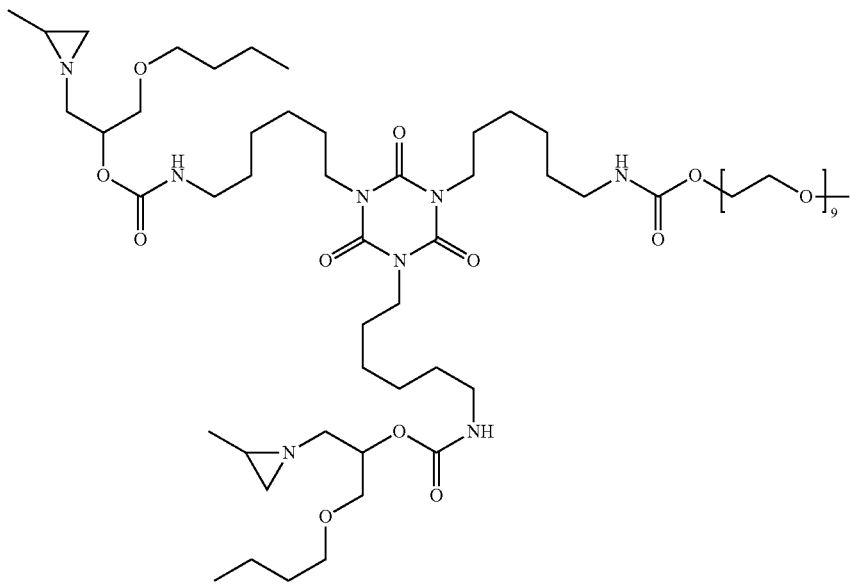

Molecular weight was confirmed by Maldi-TOF-MS: Calcd. [M+Na+]=1329.85 Da; Obs. [M+Na+]=1330.03 Da. The following components with a mass below 580 Da were determined by LC-MS and quantified:

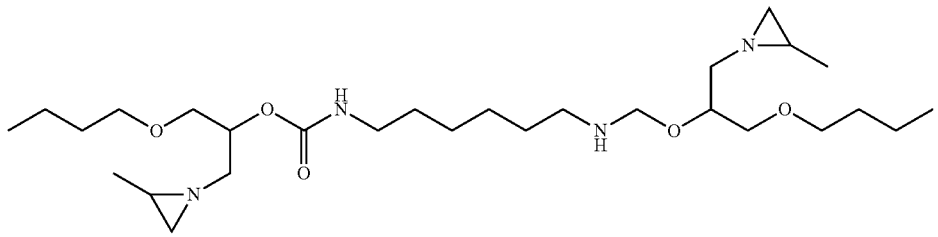 [SMILES: CCCCOCC(CN1CC1C)OCNCCCCCCNC(=O)OC(COCCCC)CN1CC1C]

was present in the composition at 0.03 wt. % and

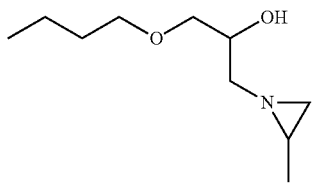

was present at less than 0.01 wt. %.

Performance of the synthesized compound as a crosslinker was assessed using spot tests on coating surfaces, based on procedures from the DIN 68861-1 standard. For these tests, 0.98 parts of the composition were mixed with 0.25 parts of 1-methoxy-2-propyl acetate and incubated at 80° C. for 10 minutes under regular agitation. Subsequently, the resulting solution was added to 15 parts of NeoRez® R-1005 under continuous stirring, and the resulting mixture was further stirred for 30 minutes.

Afterwards, this coating composition was filtered and applied to Leneta test cards using 100 μm wire rod applicators (Test 17-1). For reference, films were also cast from the same composition lacking a crosslinker (Test 17-2). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 17-1 | — | 9 | — | 8 |
| Test 17-2 | — | 1 | — | 1 |

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Ex. 17 | 1.2 | 1.3 | — | 1.1 | 1.0 | — | 1.1 | 1.2 | 1.3 | 1.2 | 1.2 | 1.2 |

Example 18

A 1 L round bottom flask equipped with a condensor was placed under a $N_2$ atmosphere and charged with propylene imine (80.0 gram), n-butyl glycidyl ether (126.0 gram) and $K_2CO_3$ (10.00 gram) and heated to 80° C. in 30 min, after which the mixture was stirred for 21 h at T=80° C. After filtration the excess of PI was removed in vacuo, followed by further purification via vacuum distillation, resulting in a colorless low viscous liquid.

49.5 grams of the resulting material (1-butoxy-3-(2-methylaziridin-1-yl)propan-2-ol) was charged to a reaction flask equipped with a thermometer, together with 35.2 grams of a poly(ethylene glycol) monomethyl ether with an average Mn of 500 Da, 0.2 grams of bismuth neodecanoate and 425 grams of dimethylformamide. The mixture was stirred with a mechanical upper stirrer under a nitrogen atmosphere and heated to 50° C. A solution of 65.2 grams of Desmodur N 3600 in 425 grams of dimethylformamide was then added dropwise in 45 minutes to the reaction flask, whereafter the mixture was heated further to 75'C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a clear, dark yellowish highly viscous liquid. The calculated molecular weights of the theoretical main components were 1065.74 Da (three aziridines), 1394.90 Da (two aziridines, 11 EG repeating units), 1438.92 Da (two aziridines, 12 EG repeating units) and 1482.95 Da (two aziridines, 13 EG repeating units), chemical structures are shown below.

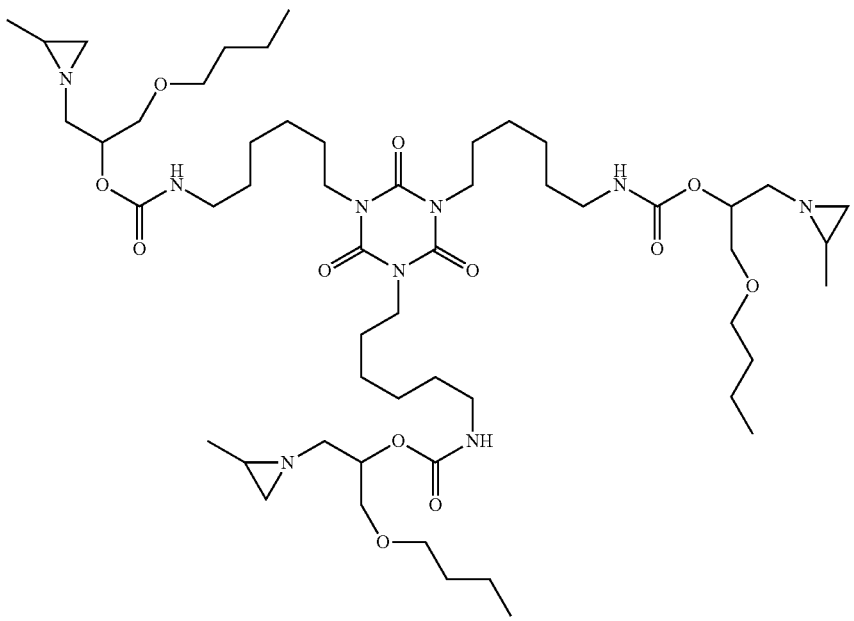

Molecular weight was confirmed by Maldi-TOF-MS:
Calcd. [M+Na+]=1088.74 Da; Obs. [M+Na+]=1088.67 Da.
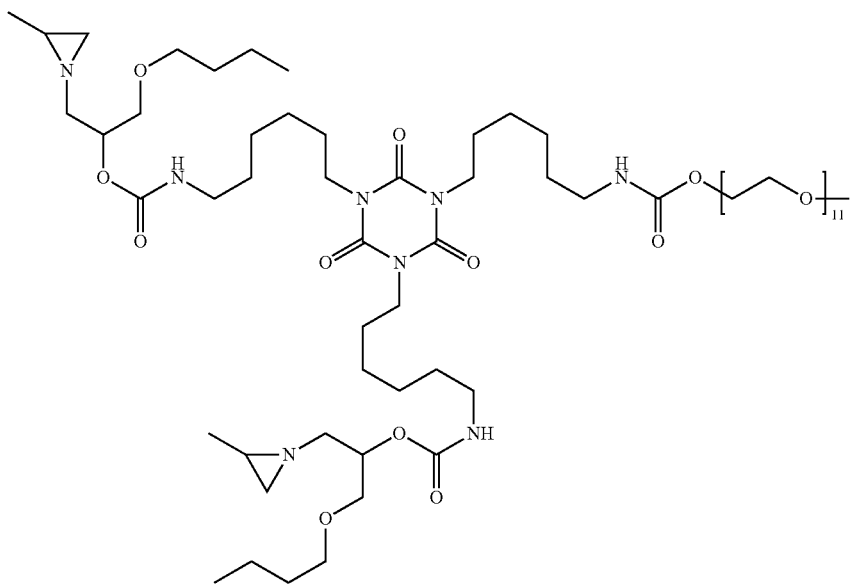
Molecular weight was confirmed by Maldi-TOF-MS:
Calcd. [M+Na+]=1417.90 Da; Obs. [M+Na+1=1417.81 Da.
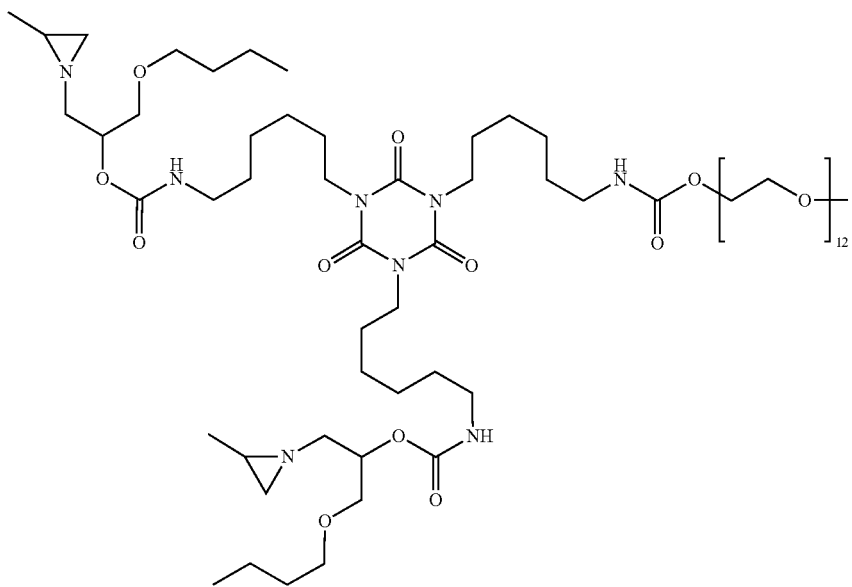

Molecular weight was confirmed by Maldi-TOF-MS: Calcd. [M+Na+]=1461.92 Da; Obs. [M+Na+]=1461.84 Da.

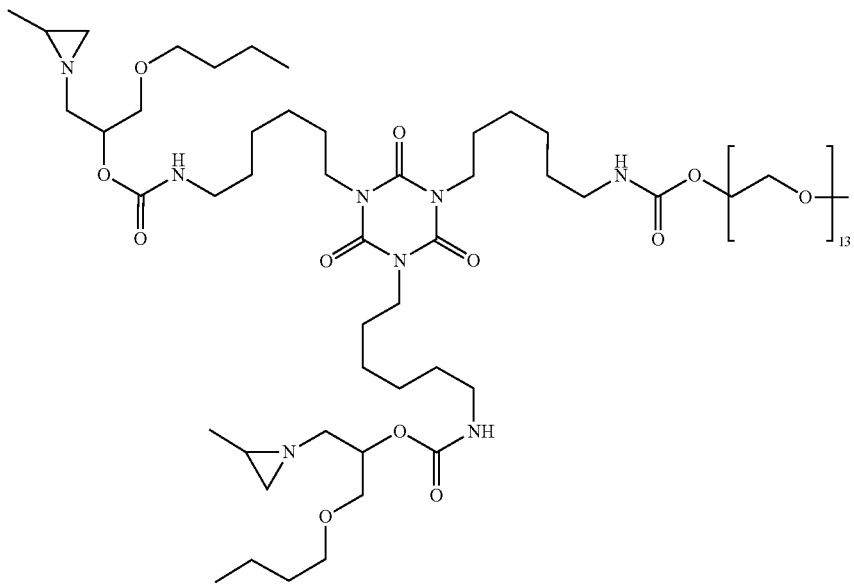

Molecular weight was confirmed by Maldi-TOF-MS: Calcd. [M+Na+]=1505.95 Da; Obs. [M+Na+]=1505.86 Da. The following components with a mass below 580 Da were determined by LC-MS and quantified:

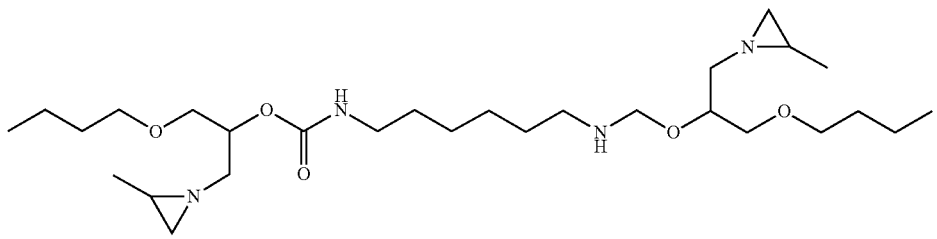 [SMILES: CCCCOCC(CN1CC1C)OCNCCCCCCNC(=O)OC(COCCCC)CN1CC1C]

was present in the composition at 0.04 wt. % and

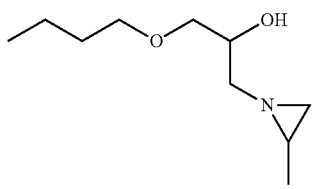

was present at 0.05 wt. %.

Performance of the synthesized compound as a crosslinker was assessed using spot tests on coating surfaces, based on procedures from the DIN 68861-1 standard. For these tests, 0.83 parts of the composition were mixed with 0.60 parts of Proglyde™ DMM (dipropylene glycol dimethyl ether, mixture of isomers) and incubated at 80° C. for 10 minutes under regular agitation. Subsequently, 0.95 parts of the resulting solution were added to 20 parts of NeoRez® R-1005 under continuous stirring, and the resulting mixture was further stirred for 30 minutes. Afterwards, this coating composition was filtered and applied to Leneta test cards using 100 μm wire rod applicators (Test 18-1). For reference, films were also cast from the same composition lacking a crosslinker (Test 18-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 18-1 | 7 | 7 | 7 | 6 |
| Test 18-2 | 1 | 1 | 1 | 1 |

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 18 | 1.0 | 1.1 | 1.2 | 0.9 | 0.9 | 0.7 | 1.1 | 1.2 | 1.3 | 0.9 | 0.8 | 0.7 |

For corroborative purposes, the mutagenicity of the crosslinker composition was also assessed using the established Ames test (Bacterial Reversion Assay), according to the following guidelines:

OECD Guideline 471. Genetic Toxicology: Bacterial Reverse Mutation Test. (Adopted Jul. 21, 1997).

EC Guideline No. 440/2008. Part B: Methods for the Determination of Toxicity and other health effects, Guideline B.13/14: "Mutagenicity: Reverse Mutation Test using Bacteria". Official Journal of the European Union No. L142, 31 May 2008.

This test showed that the crosslinker composition as described above is not mutagenic.

Example 19

A 20 mL reaction vial was charged with propylene imine (2.97 gram), cyclohexene oxide (4.06 gram), capped, heated to 55° C., after which the mixture was stirred for 8 days at T=55° C. The excess of PI was removed in vacuo, followed by further purification via vacuum distillation, resulting in a white powder. 2.00 grams of Desmodur N 3600, 0.02 grams of bismuth neodecanoate and 3.60 grams of dimethylformamide were charged to a reaction flask equipped with a thermometer. The mixture was stirred with a mechanical upper stirrer under a nitrogen atmosphere and heated to 50° C. A solution of 1.54 grams of the product from the first step in 3.60 grams of dimethylformamide was then added dropwise in 10 minutes to the reaction flask, a further 3.60 grams of dimethylformamide was flushed through the feeding funnel into the reaction mixture, whereafter the mixture was heated further to 80° C. Samples were taken at regular intervals and the reaction progress was monitored using a Bruker Alpha FT-IR spectrometer until no change in NCO-stretch at 2200-2300 cm$^{-1}$ was observed. Subsequently, 0.06 grams of 1-butanol were added to the mixture, followed by further reaction to complete disappearance of aforementioned NCO-stretch peak. The product was a slightly opaque liquid. The calculated molecular weight of the theoretical main component was 969.66 Da, chemical structure is shown below.

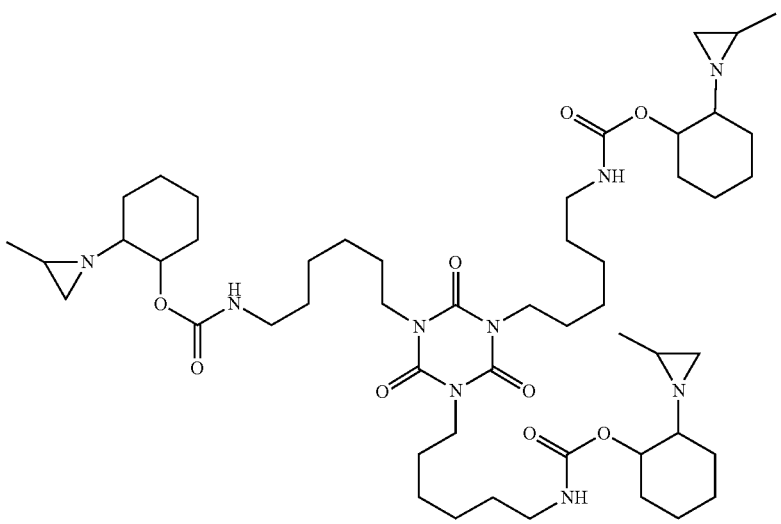

Molecular weight was confirmed by Maldi-TOF-MS: Calcd. [M+Na+]=992.66 Da; Obs. [M+Na+]=992.77 Da. The following components with a mass below 580 Da were determined by LC-MS and quantified:

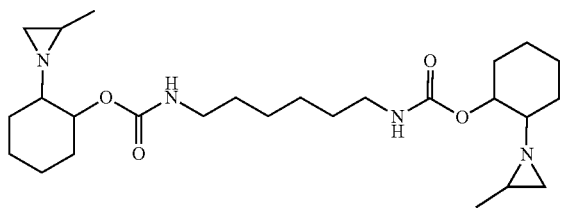 [SMILES: CC1CN1C1CCCCC1OC(=O)NCCCCCCNC(=O)OC1CCCCC1N1CC1C]

was present in the composition at 0.27 wt. % and

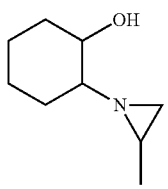

was present at less than 0.01 wt. %.

Performance of the synthesized compound as a crosslinker was assessed using spot tests on coating surfaces, based on procedures from the DIN 68861-1 standard. For these tests, 2.01 parts of the composition (i.e. at 25% solids in dimethylformamide) was added to 15 parts of NeoRez® R-1005 under continuous stirring, and the resulting mixture was further stirred for 30 minutes. Afterwards, this coating composition was filtered and applied to Leneta test cards using 100 μm wire rod applicators (Test 19-1). For reference, films were also cast from the same composition lacking a crosslinker (Test 19-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 19-1 | — | 8 | — | 6 |
| Test 19-2 | — | 1 | — | 1 |

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Ex. 19 1.1 | 1.3 | — | 1.2 | 1.3 | — | 1.1 | 1.2 | 1.2 | 1.2 | 1.3 | 1.3 |

Example 20

A 1 L round bottom flask equipped with a condensor was placed under a $N_2$ atmosphere and charged with propylene imine (91.0 gram), 2-ethylhexylglycidyl ether (201.0 gram) and $K_2CO_3$ (10.00 gram) and heated to 80° C., after which the mixture was stirred for 47 h at T=80° C. After filtration the excess of PI was removed in vacuo, followed by further purification via vacuum distillation, resulting in a colorless low viscous liquid.

130 grams of the resulting material was charged to a reaction flask equipped with a thermometer, together with 0.02 grams of bismuth neodecanoate and 668 grams of dimethylformamide. The mixture was stirred with a mechanical upper stirrer under a nitrogen atmosphere and heated to 50° C. A solution of 107.4 grams of Desmodur N 3600 in 668 grams of dimethylformamide was then added dropwise in 45 minutes to the reaction flask, a further 10 grams of dimethylformamide was flushed through the feeding funnel into the reaction mixture, whereafter the mixture was heated further to 75° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a highly viscous colorless liquid. The calculated molecular weight of the theoretical main component was 1233.93 Da, chemical structure is shown below.

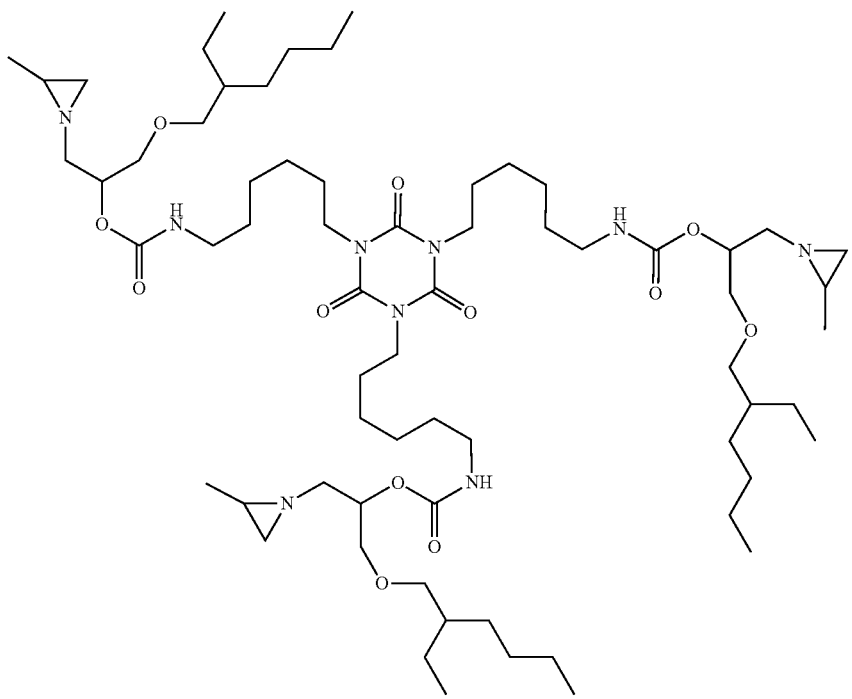 [SMILES: CCCCC(CC)COCC(CN1CC1C)OC(=O)NCCCCCCn1c(=O)n(CCCCCCNC(=O)OC(COCC(CC)CCCC)CN2CC2C)c(=O)n(CCCCCCNC(=O)OC(COCC(CC)CCCC)CN2CC2C)c1=O]

Molecular weight was confirmed by Maldi-TOF-MS: Calcd. [M+Na+]=1256.93 Da; Obs. [M+Na+]=1256.86 Da. The following components with a mass below 580 Da were determined by LC-MS and quantified:

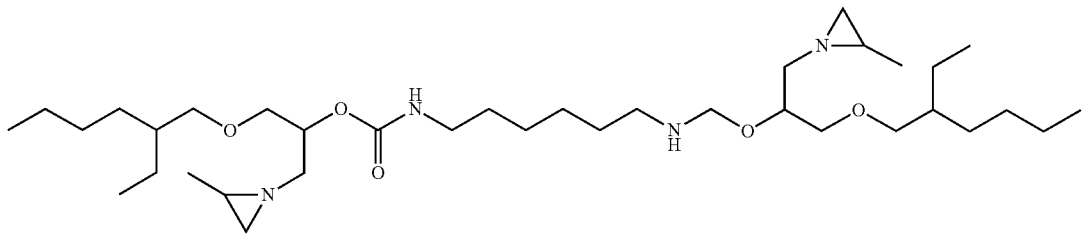 [SMILES: CCCCC(CC)COCC(CN1CC1C)OCNCCCCCCNC(=O)OC(COCC(CC)CCCC)CN1CC1C]

was present in the composition at 0.84 wt. % and IC15C

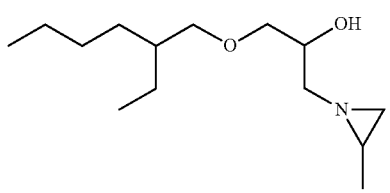 [SMILES: CCCCC(CC)COCC(O)CN1CC1C]

was present at 0.16 wt. %.

Performance of the synthesized compound as a crosslinker was assessed using spot tests on coating surfaces, based on procedures from the DIN 68861-1 standard. For these tests, 0.96 parts of the composition were mixed with 0.96 parts of 1-methoxy-2-propyl acetate and incubated at 80° C. for 10 minutes under regular agitation. Subsequently, the resulting solution was added to 15 parts of NeoRez® R-1005 under continuous stirring, and the resulting mixture was further stirred for 30 minutes. Afterwards, this coating composition was filtered and applied to Leneta test cards using 100 μm wire rod applicators (Test 20-1). For reference, films were also cast from the same composition lacking a crosslinker (Test 20-2). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 20-1 | — | 8 | — | 8 |
| Test 20-2 | — | 1 | — | 1 |

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 20 | 1.0 | 1.0 | 0.7 | 1.1 | 1.3 | 1.2 | 0.9 | 0.8 | 0.7 | 1.0 | 1.1 | 1.1 |

Example 21

A 20 mL reaction vial was charged with propylene imine (1.98 gram), o-cresyl glycidyl ether (5.57 gram), capped, heated to 55° C., after which the mixture was stirred for 20 hours at T=55° C. The excess of PI was removed in vacuo, followed by further purification via vacuum distillation, resulting in a colorless low viscous liquid.

0.90 grams of Desmodur N 3600, 0.02 grams of bismuth neodecanoate and 5.80 grams of dimethylformamide were charged to a reaction flask equipped with a thermometer. The mixture was stirred with a mechanical upper stirrer under a nitrogen atmosphere and heated to 50° C. A solution of 0.99 grams of the product from the first step in 5.80 grams of dimethylformamide was then added dropwise in 5 minutes to the reaction flask, a further 5.80 grams of dimethylformamide was flushed through the feeding funnel into the reaction mixture, whereafter the mixture was heated further to 80° C. Samples were taken at regular intervals and the reaction progress was monitored using a Bruker Alpha FT-IR spectrometer until no NCO-stretch at 2200-2300 cm$^{-1}$ was observed. Evaporation of the solvent in vacuo to 43% solids yielded a low viscosity yellowish liquid. The calculated molecular weight of the theoretical main component was 1167.69 Da, chemical structure is shown below.

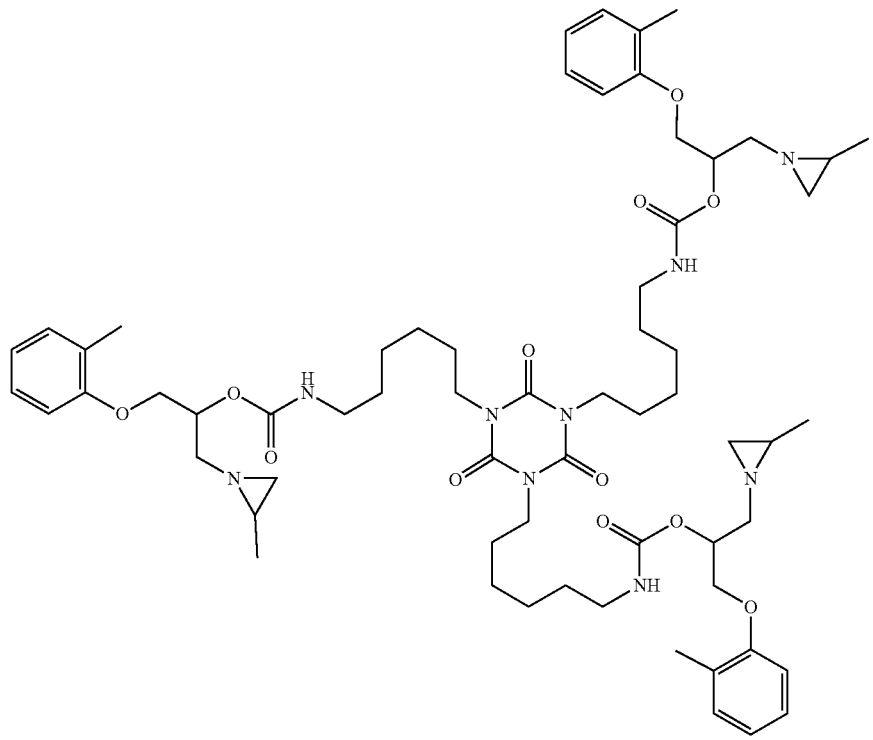 [SMILES: Cc1ccccc1OCC(CN1CC1C)OC(=O)NCCCCCCn1c(=O)n(CCCCCCNC(=O)OC(COc2ccccc2C)CN2CC2C)c(=O)n(CCCCCCNC(=O)OC(COc2ccccc2C)CN2CC2C)c1=O]

Molecular weight was confirmed by Maldi-TOF-MS: Calcd. [M+Na+]=1190.69 Da; Obs. [M+Na+]=1190.77 Da. The following components with a mass below 580 Da were determined by LC-MS and quantified:

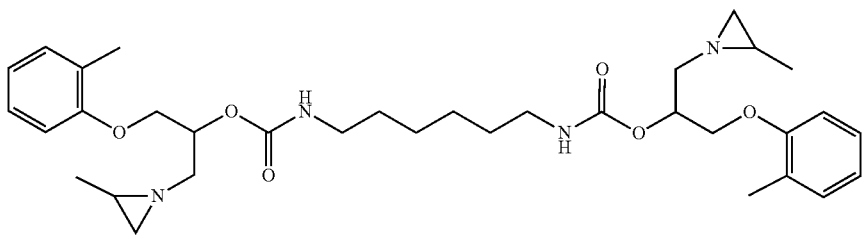 [SMILES: Cc1ccccc1OCC(CN1CC1C)OC(=O)NCCCCCCNC(=O)OC(COc1ccccc1C)CN1CC1C]

was present in the composition at 0.08 wt. % and

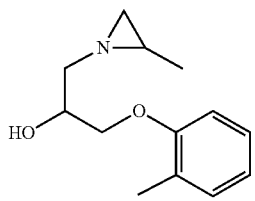 [SMILES: Cc1ccccc1OCC(O)CN1CC1C]

was present at 0.08 wt. %.

Performance of the synthesized compound as a crosslinker was assessed using spot tests on coating surfaces, based on procedures from the DIN 68861-1 standard. For these tests, 0.47 parts of the composition (i.e. at 43% solids in dimethylformamide) was added to 5 parts of NeoRez® R-1005 under continuous stirring, and the resulting mixture was further stirred for 30 minutes. Afterwards, this coating composition was filtered and applied to Leneta test cards using 100 μm wire rod applicators (Test 21-1). For reference, films were also cast from the same composition lacking a crosslinker (Test 21-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 21-1 | — | 8 | — | 8 |
| Test 21-2 | — | 1 | — | 1 |

| | Genotoxicity test | | | | | | | | | | |
|---|---|---|---|---|---|---|---|---|---|---|---|
| | Without S9 rat liver extract | | | | | | With S9 rat liver extract | | | | |
| | Bscl 2 | | | Rtkn | | | Bscl 2 | | | Rtkn | |
| | | | | | concentration | | | | | | |
| | 10 | 25 | 50 | 10 | 25 | 50 | 10 | 25 | 50 | 10 | 25 | 50 |
| Ex. 21 | 1.1 | 1.2 | 1.6 | 1.2 | 1.3 | 1.5 | 1.0 | 1.3 | 1.4 | 1.2 | 1.4 | 1.5 |

Example 22

A 1 L round bottom flask equipped with a condenser was placed under a $N_2$ atmosphere and charged with propylene imine (69.0 gram), Cardura E10P (201.0 gram) and $K_2CO_3$ (7.30 gram) and heated to 80° C., after which the mixture was stirred for 24 h at T=80° C. After filtration the excess of PI was removed in vacuo, resulting in a colorless low viscous liquid.

11.09 grams of the resulting material (2-hydroxy-3-(2-methylaziridin-1-yl)propyl neodecanoate) was charged to a reaction flask equipped with a thermometer, together with 0.02 grams of bismuth neodecanoate and 46 grams of dimethylformamide. The mixture was stirred with a mechanical upper stirrer under a nitrogen atmosphere and heated to 50° C. A solution of 5.00 grams of 1,3-bis(1-isocyanato-1-methylethyl)benzene in 46 grams of dimethylformamide was then added dropwise in 45 minutes to the reaction flask, whereafter the mixture was heated further to 80° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain an opaque viscous liquid. The calculated molecular weight of the theoretical main component was 814.58 Da, chemical structure is shown below.

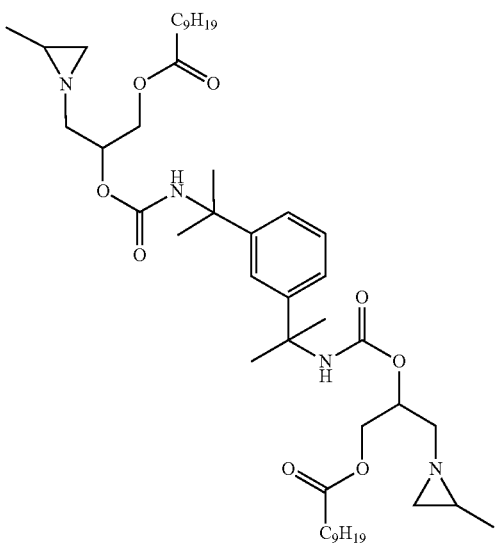

Molecular weight was confirmed by Maldi-TOF-MS: Calcd. [M+Na+]=837.58 Da; Obs. [M+Na+]=837.48 Da. The following components with a mass below 580 Da were determined by LC-MS and quantified:

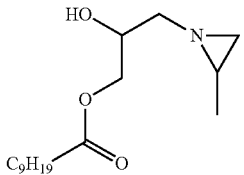

was present in the composition at 1.3 wt. %.

Performance of the synthesized compound as a cross-linker was assessed using spot tests on coating surfaces, based on procedures from the DIN 68861-1 standard. For these tests, 0.61 parts of the composition were mixed with 0.60 parts of Proglyde™ DMM (dipropylene glycol dimethyl ether, mixture of isomers) and incubated at 80° C. for 10 minutes under regular agitation. Subsequently, 0.81 parts of the resulting solution were added to 20 parts of NeoRez® R-1005 under continuous stirring, and the resulting mixture was further stirred for 30 minutes. Afterwards, this coating composition was filtered and applied to Leneta test cards using 100 μm wire rod applicators (Test 22-1). For reference, films were also cast from the same composition lacking a crosslinker (Test 22-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 22-1 | 7 | 7 | 7 | 7 |
| Test 22-2 | 1 | 1 | 1 | 1 |

| Genotoxicity test | | | | | | | | | | | |
|---|---|---|---|---|---|---|---|---|---|---|---|
| | Without S9 rat liver extract | | | | | | With S9 rat liver extract | | | | |
| | Bscl 2 | | | Rtkn | | | Bscl 2 | | | Rtkn | |
| | concentration | | | | | | | | | | |
| | 10 | 25 | 50 | 10 | 25 | 50 | 10 | 25 | 50 | 10 | 25 | 50 |
| Ex. 22 | 1.0 | 1.0 | 0.9 | 1.0 | 1.0 | 1.0 | 1.2 | 1.2 | 1.2 | 1.1 | 1.1 | 1.0 |

Example 23

A 1 L round bottom flask equipped with a condenser was placed under a $N_2$ atmosphere and charged with propylene imine (69.0 gram), Cardura E10P (201.0 gram) and $K_2CO_3$ (7.30 gram) and heated to 80° C., after which the mixture was stirred for 24 h at T=80° C. After filtration the excess of PI was removed in vacuo, resulting in a colorless low viscous liquid.

10.33 grams of the resulting material (2-hydroxy-3-(2-methylaziridin-1-yl)propyl neodecanoate) was charged to a reaction flask equipped with a thermometer, together with 0.02 grams of bismuth neodecanoate and 43 grams of dimethylformamide. The mixture was stirred with a mechanical upper stirrer under a nitrogen atmosphere and heated to 50° C. A solution of 5.00 grams of 4,4'-methylenebis(cyclohexyl isocyanate) in 43 grams of dimethylformamide was then added dropwise in 45 minutes to the reaction flask, whereafter the mixture was heated further to 80° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain an opaque viscous liquid. The calculated molecular weight of the theoretical main component was 832.63 Da, chemical structure is shown below.

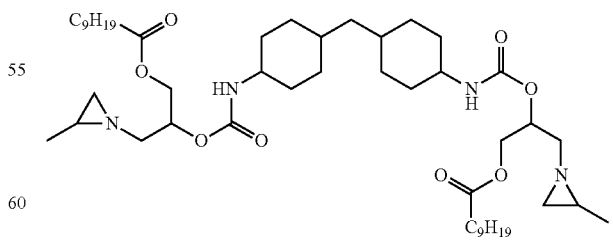

Molecular weight was confirmed by Maldi-TOF-MS: Calcd. [M+Na+]=855.62 Da; Obs. [M+Na+]=855.52 Da. The following components with a mass below 580 Da were determined by LC-MS and quantified:

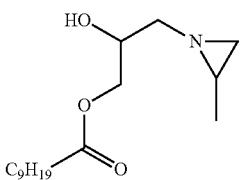

was present in the composition at 0.2 wt. %.

Performance of the synthesized compound as a crosslinker was assessed using spot tests on coating surfaces, based on procedures from the DIN 68861-1 standard. For these tests, 0.64 parts of the composition were mixed with 0.60 parts of Proglyde™ DMM (dipropylene glycol dimethyl ether, mixture of isomers) and incubated at 80° C. for 10 minutes under regular agitation. Subsequently, 0.83 parts of the resulting solution were added to 21 parts of NeoRez® R-1005 under continuous stirring, and the resulting mixture was further stirred for 30 minutes. Afterwards, this coating composition was filtered and applied to Leneta test cards using 100 μm wire rod applicators (Test 23-1). For reference, films were also cast from the same composition lacking a crosslinker (Test 23-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 23-1 | 2 | 2 | 2 | 2 |
| Test 23-2 | 1 | 1 | 1 | 1 |

| Genotoxicity test | | | | | | | | | | | |
|---|---|---|---|---|---|---|---|---|---|---|---|
| | Without S9 rat liver extract | | | | | | With S9 rat liver extract | | | | |
| | Bscl 2 | | | Rtkn | | | Bscl 2 | | | Rtkn | |
| | concentration | | | | | | | | | | |
| | 10 | 25 | 50 | 10 | 25 | 50 | 10 | 25 | 50 | 10 | 25 | 50 |
| Ex. 23 | 1.1 | 1.2 | 1.2 | 1.1 | 1.2 | 1.1 | 1.1 | 1.1 | 1.1 | 1.0 | 1.2 | 1.2 |

Example 24

A 1 L round bottom flask equipped with a condensor was placed under a $N_2$ atmosphere and charged with propylene imine (69.0 gram), Cardura E10P (201.0 gram) and $K_2CO_3$ (7.30 gram) and heated to 80° C., after which the mixture was stirred for 24 h at T=80° C. After filtration the excess of PI was removed in vacuo, resulting in a colorless low viscous liquid.

2.20 grams of the resulting material (2-hydroxy-3-(2-methylaziridin-1-yl)propyl neodecanoate) was charged to a reaction flask equipped with a thermometer, together with 0.02 grams of bismuth neodecanoate and 18 grams of dimethylformamide. The mixture was stirred with a mechanical upper stirrer under a nitrogen atmosphere and heated to 50° C. A solution of 1.50 grams of Desmodur N 3600 in 18 grams of dimethylformamide was then added dropwise in 15 minutes to the reaction flask, whereafter the mixture was heated further to 70° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain an opaque highly viscous liquid. The calculated molecular weight of the theoretical main component was 1359.96 Da, chemical structure is shown below.

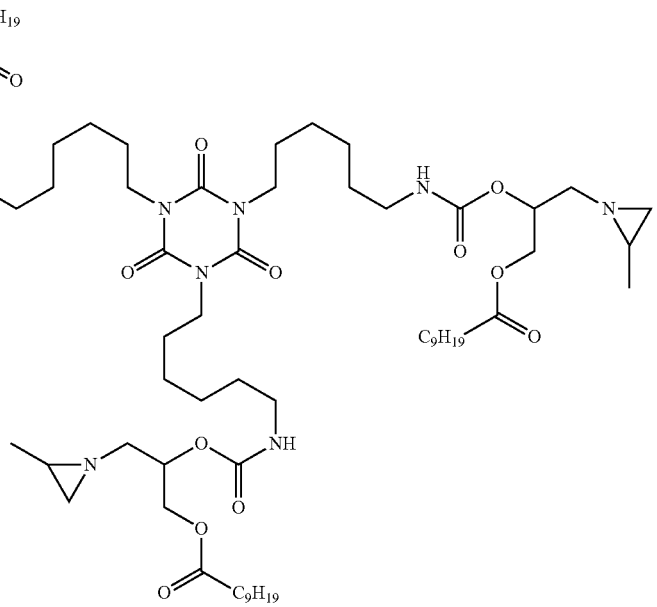

Molecular weight was confirmed by Maldi-TOF-MS: Calcd. [M+Na+]=1382.95 Da; Obs. [M+Na+]=1382.86 Da. The following components with a mass below 580 Da were determined by LC-MS and quantified:

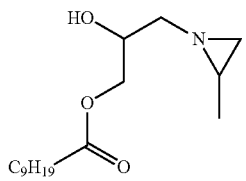

was present in the composition at 0.27 wt. %.

Performance of the synthesized compound as a crosslinker was assessed using spot tests on coating surfaces, based on procedures from the DIN 68861-1 standard. For these tests, 0.68 parts of the composition were mixed with 0.60 parts of Proglyde™ DMM (dipropylene glycol dimethyl ether, mixture of isomers) and incubated at 80° C. for 10 minutes under regular agitation. Subsequently, 0.86 parts of the resulting solution were added to 21 parts of NeoRez® R-1005 under continuous stirring, and the resulting mixture was further stirred for 30 minutes. Afterwards, this coating composition was filtered and applied to Leneta test cards using 100 μm wire rod applicators (Test 24-1). For reference, films were also cast from the same composition lacking a crosslinker (Test 24-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 24-1 | 3 | 2 | 1 | 1 |
| Test 24-2 | 1 | 1 | 1 | 1 |

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Ex. 24 | | | | | | | | | | | |
| 1.1 | 1.2 | 1.0 | 1.1 | 1.2 | 1.0 | 1.0 | 1.1 | 1.1 | 1.1 | 1.1 | 1.2 |

Example 25

A 1 L round bottom flask equipped with a condensor was placed under a $N_2$ atmosphere and charged with propylene imine (69.0 gram), Cardura E10P (201.0 gram) and $K_2CO_3$ (7.30 gram) and heated to 80° C., after which the mixture was stirred for 24 h at T=80° C. After filtration the excess of PI was removed in vacuo, resulting in a colorless low viscous liquid.

A 500 mL round bottom flask equipped with a thermometer and overhead stirrer was placed under a $N_2$ atmosphere and charged with Desmodur W (60.08 gram) and 65.35 gram of the product of the previous step. The resulting mixture was heated to 50° C., after which bismuth neodecanoate (0.05 gram) was added. The mixture was allowed to exotherm followed by further heating to 80° C. and stirring for 2.5 hours at 80° C. To the mixture was then added pTHF650 (74.52 gram) and the mixture was stirred for another 1 hour at 80° C. The solvent was removed in vacuo to obtain a colorless solid.

The calculated molecular weights of the theoretical main components were 832.63 Da (structure 25-a: no pTHF650 repeat unit), 1473.10 (structure 25-b: one pTHF segment with 5 tetramethylene ether glycol repeat units), 1545.15 Da (structure 25-c: one pTHF segment with 6 tetramethylene ether glycol repeat units) and 2257.68 Da (structure 25-d: two pTHF segments with 6 tetramethylene ether glycol repeat units each), chemical structures are shown below.

Structure 25-a:

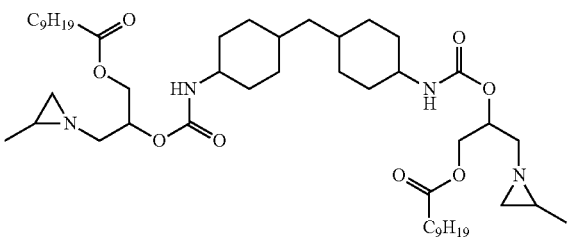

Molecular weight was confirmed by Maldi-TOF-MS: Structure 25-a: Calcd. [M+Na+]=855.63 Da; Obs. [M+Na+]=855.66 Da.

Structure 25-b:
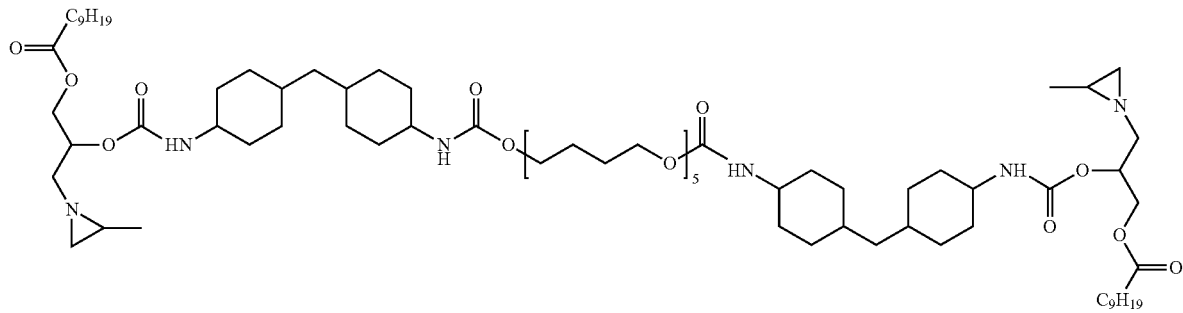
Molecular weight was confirmed by Maldi-TOF-MS: Structure 25-b: Calcd. [M+Na+]=1496.10 Da; Obs. [M+Na+]=1496.16 Da.
Structure 25-c:
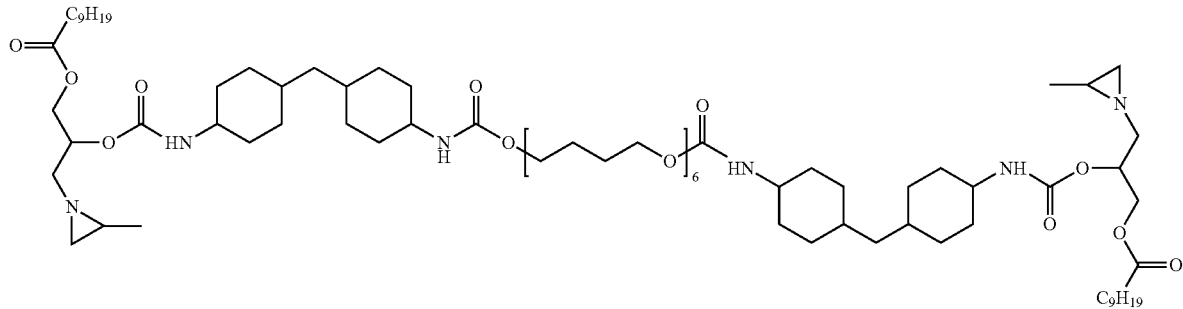
Molecular weight was confirmed by Maldi-TOF-MS: Structure 25-c: Calcd. [M+Na+]=1568.15 Da; Obs. [M+Na+]=1568.21 Da.
Structure 25-d:
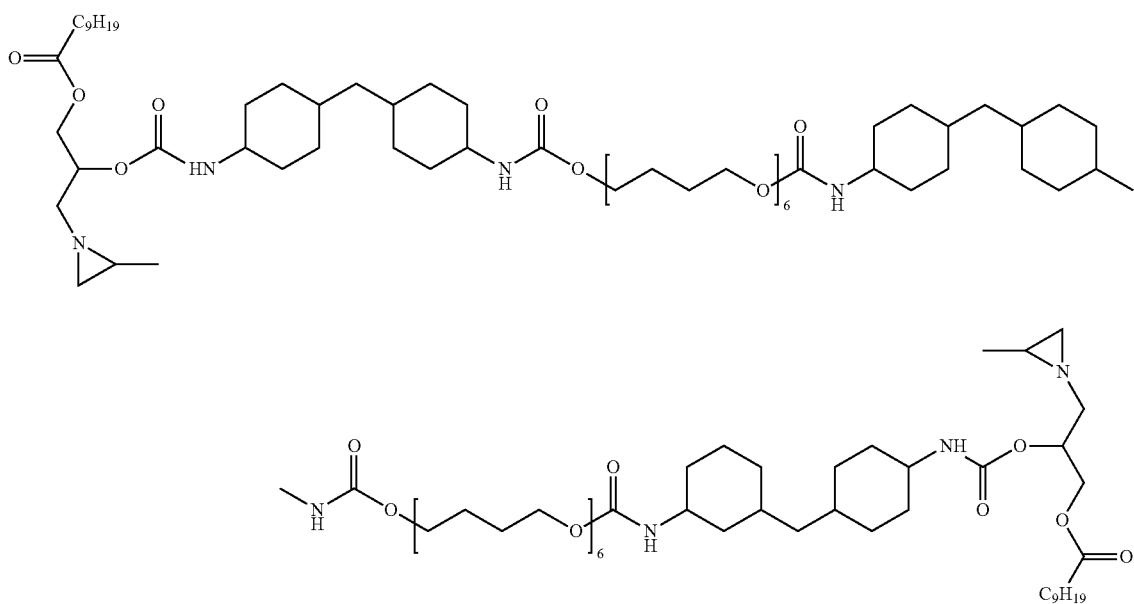

Molecular weight was confirmed by Maldi-TOF-MS: Structure 25-d: Calcd. [M+Na+]=2280.68 Da; Obs. [M+Na+]=2280.78 Da.

Performance of the synthesized compound as a cross-linker was assessed using spot tests on coating surfaces, based on procedures from the DIN 68861-1 standard. For these tests, 1.36 parts of the composition were mixed with 1.36 parts of 1-methoxy-2-propyl acetate and incubated at 80° C. for 10 minutes under regular agitation. Subsequently, the resulting solution was added to 15 parts of NeoRez® R-1005 under continuous stirring, and the resulting mixture was further stirred for 30 minutes. Afterwards, this coating composition was filtered and applied to Leneta test cards using 100 μm wire rod applicators (Test 25-1). For reference, films were also cast from the same composition lacking a crosslinker (Test 25-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 25-1 | — | 8 | — | 8 |
| Test 25-2 | — | 1 | — | 1 |

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 25 | 1.1 | 1.2 | 1.3 | 1.1 | 1.2 | 1.2 | 1.2 | 1.2 | — | 1.1 | 1.4 | — |

Example 26

A 1 L round bottom flask equipped with a condensor was placed under a $N_2$ atmosphere and charged with propylene imine (69.0 gram), Cardura E10P (201.0 gram) and $K_2CO_3$ (7.30 gram) and heated to 80° C., after which the mixture was stirred for 24 h at T=80° C. After filtration the excess of PI was removed in vacuo, resulting in a colorless low viscous liquid.

A 500 mL round bottom flask equipped with a thermometer and overhead stirrer was placed under a $N_2$ atmosphere and charged with Desmodur W (49.60 gram) and 53.95 gram of the product of the previous step. The resulting mixture was heated to 50° C., after which bismuth neodecanoate (0.04 gram) was added. The mixture was allowed to exotherm followed by further heating to 80° C. and stirring for 2 hours at 80° C. To the mixture was then added Durez-ter S 105-110 (96.40 gram). After another 2.5 hours stirring at 80° C. a second charge of Durez-ter S 105-110 (10.00 gram) was added to the mixture and the mixture was stirred for another 11 hours at 80° C. The solvent was removed in vacuo to obtain a white solid.

The calculated molecular weight of the theoretical main components were 832.63 Da (structure 26-a), 1212.90 (structure 26-b: one hexanediol connecting group between two Desmodur W groups coming from the Durez-ter S 105-110), 1441.03 Da (structure 26-c: one polyester repeating unit), 1669.17 Da (structure 26-d: two polyester repeating units), 1897.30 Da (structure 26-e: three polyester repeating units), and 2125.44 Da (structure 26-f: four polyester repeating units), chemical structures are shown below.

Structure 26-a:

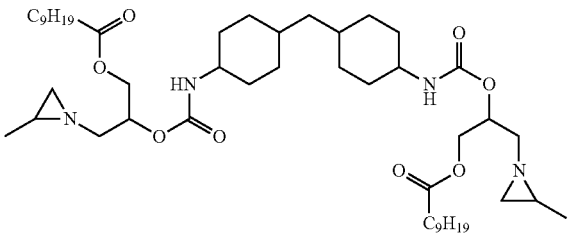

Molecular weight was confirmed by Maldi-TOF-MS: Structure 26-a: Calcd. [M+Na+]=855.63 Da; Obs. [M+Na+]=855.70 Da.

Structure 26-b:

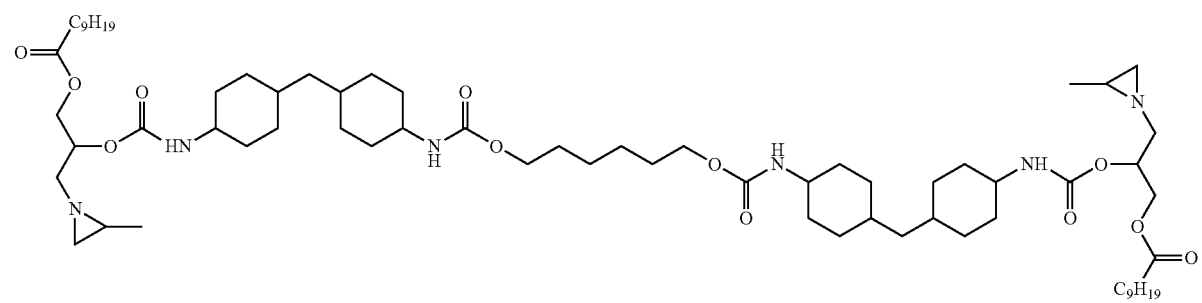

Molecular weight was confirmed by Maldi-TOF-MS:
Structure 26-b: Calcd. [M+Na+]=1235.90 Da; Obs. [M+Na+]=1236.01 Da.
Structure 26-c:
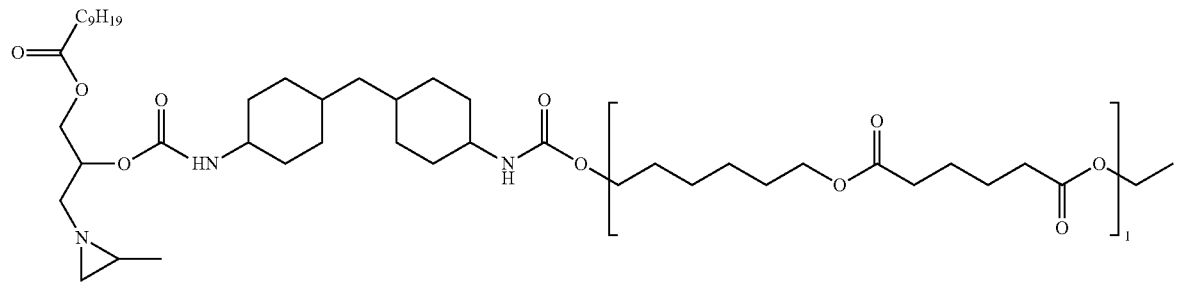
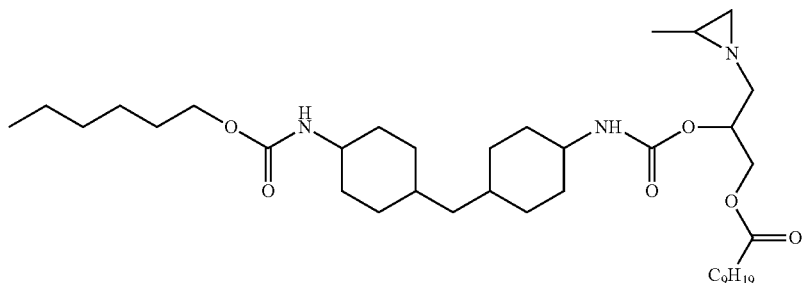
Molecular weight was confirmed by Maldi-TOF-MS:
Structure 26-c: Calcd. [M+Na+]=1464.03 Da; Obs. [M+Na+]=1464.16 Da.
Structure 26-d:
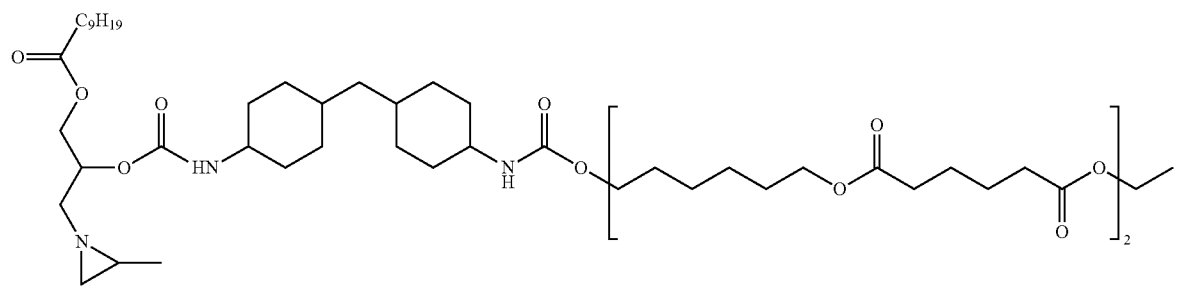
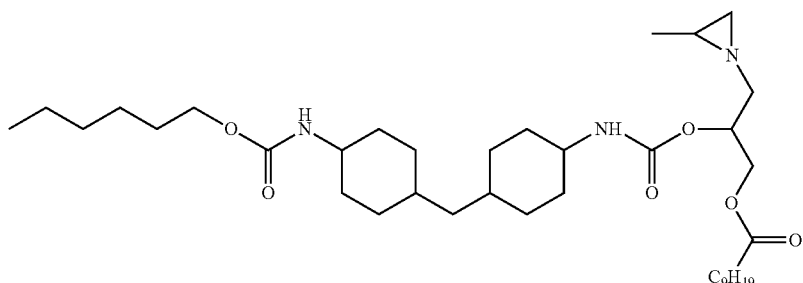

Molecular weight was confirmed by Maldi-TOF-MS:
Structure 26-d: Calcd. [M+Na+]=1692.17 Da; Obs. [M+Na+]=1692.32 Da.
Structure 26-e:
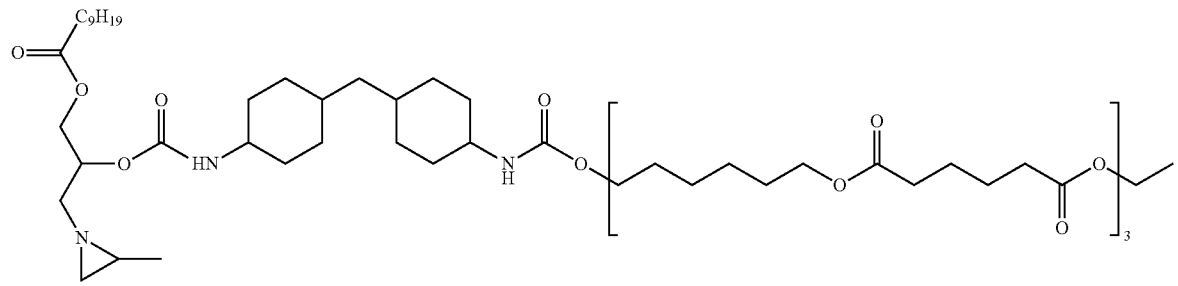
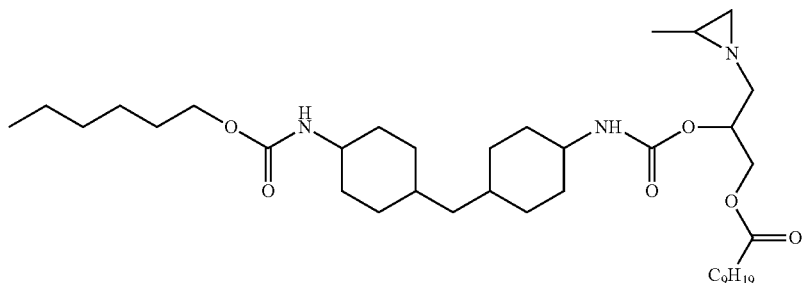
Molecular weight was confirmed by Maldi-TOF-MS:
Structure 26-e: Calcd. [M+Na+]=1920.30 Da; Obs. [M+Na+]=1920.48 Da.
Structure 26-f:
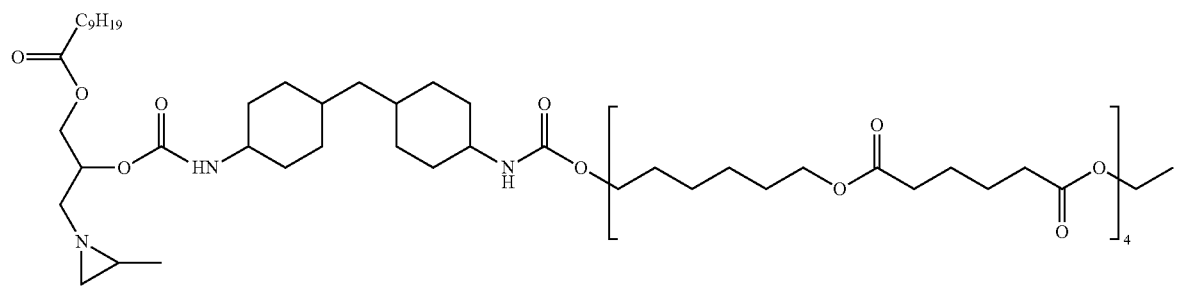
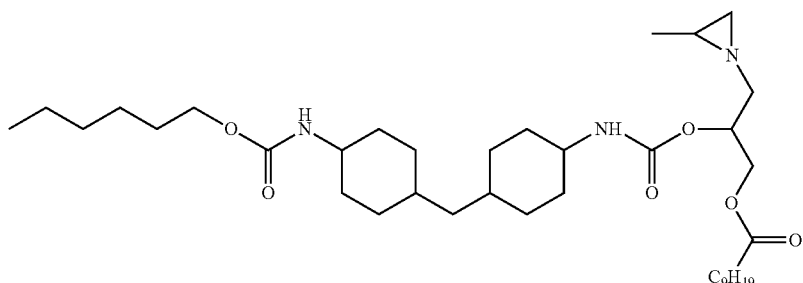

Molecular weight was confirmed by Maldi-TOF-MS: Structure 26-f: Calcd. [M+Na+]=2148.44 Da; Obs. [M+Na+]=2148.62 Da.

Performance of the synthesized compound as a crosslinker was assessed using spot tests on coating surfaces, based on procedures from the DIN 68861-1 standard. For these tests, 1.73 parts of the composition were mixed with 1.73 parts of 1-methoxy-2-propyl acetate and incubated at 80° C. for 10 minutes under regular agitation.

Subsequently, the resulting solution was added to 15 parts of NeoRez® R-1005 under continuous stirring, and the resulting mixture was further stirred for 30 minutes. Afterwards, this coating composition was filtered and applied to Leneta test cards using 100 μm wire rod applicators (Test 26-1). For reference, films were also cast from the same composition lacking a crosslinker (Test 26-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 26-1 | — | 8 | — | 8 |
| Test 26-2 | — | 1 | — | 1 |

| Genotoxicity test | | | | | | | | | | | |
|---|---|---|---|---|---|---|---|---|---|---|---|
| Without S9 rat liver extract | | | | | | With S9 rat liver extract | | | | | |
| Bscl 2 | | | Rtkn | | | Bscl 2 | | | Rtkn | | |
| concentration | | | | | | | | | | | |
| 10 | 25 | 50 | 10 | 25 | 50 | 10 | 25 | 50 | 10 | 25 | 50 |
| Ex. 26 1.0 | 1.1 | 1.4 | 1.2 | 1.3 | 1.5 | 1.1 | 1.2 | 1.2 | 1.3 | 1.4 | 1.3 |

Example 27

A 1 L round bottom flask equipped with a condensor was placed under a $N_2$ atmosphere and charged with propylene imine (69.0 gram), Cardura E10P (201.0 gram) and $K_2CO_3$ (7.30 gram) and heated to 80° C., after which the mixture was stirred for 24 h at T=80° C. After filtration the excess of PI was removed in vacuo, resulting in a colorless low viscous liquid.

2.89 grams of the resulting material (2-hydroxy-3-(2-methylaziridin-1-yl)propyl neodecanoate) was charged to a reaction flask equipped with a thermometer, together with 0.02 grams of bismuth neodecanoate, 1.35 grams of a poly(ethylene glycol) monomethyl ether with an average Mn of 500 Da and 30 grams of dimethylformamide. The mixture was stirred with a mechanical upper stirrer under a nitrogen atmosphere and heated to 50° C. A solution of 2.5 grams of Desmodur N 3600 in 30 grams of dimethylformamide was then added dropwise in 45 minutes to the reaction flask, whereafter the mixture was heated further to 70° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a clear highly viscous liquid. The calculated molecular weight of the theoretical main components were 1359.96 Da (three aziridines) and 1591.04 Da (two aziridines, 11 EG repeating units), chemical structures are shown below.

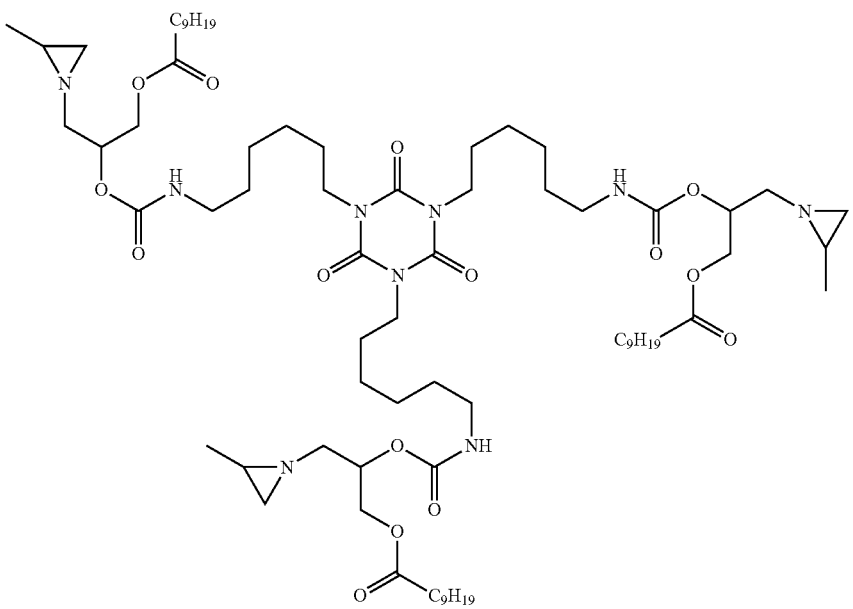

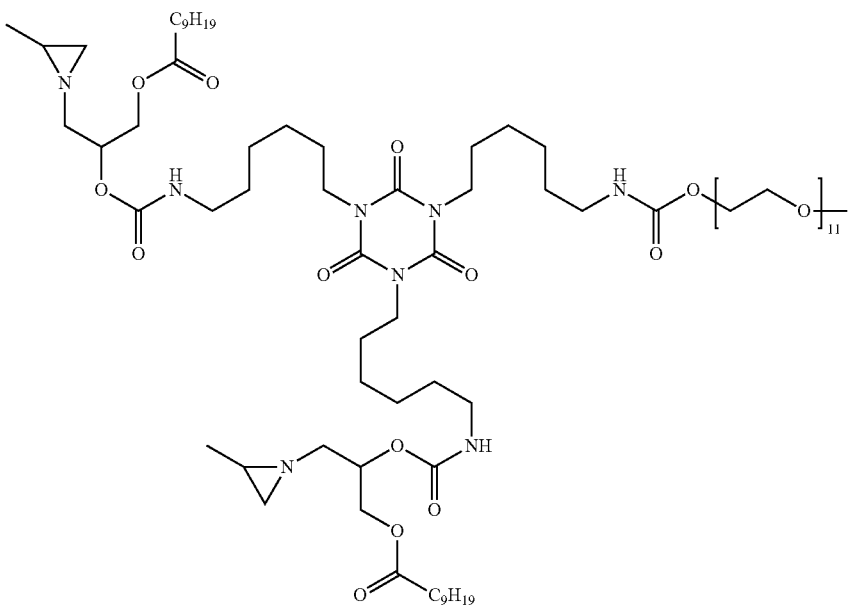

Performance of the synthesized compound as a crosslinker was assessed using spot tests on coating surfaces, based on procedures from the DIN 68861-1 standard. For these tests, 0.93 parts of the composition were mixed with 0.60 parts of Proglyde™ DMM (dipropylene glycol dimethyl ether, mixture of isomers) and incubated at 80° C. for 10 minutes under regular agitation. Subsequently, 1.02 parts of the resulting solution were added to 20 parts of NeoRez® R-1005 under continuous stirring, and the resulting mixture was further stirred for 30 minutes. Afterwards, this coating composition was filtered and applied to Leneta test cards using 100 μm wire rod applicators (Test 27-1). For reference, films were also cast from the same composition lacking a crosslinker (Test 27-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| | Ethanol spot test | | | |
|---|---|---|---|---|
| Sample | 30 min | 60 min | 120 min | 300 min |
| Test 27-1 | 8 | 7 | 7 | 7 |
| Test 27-2 | 1 | 1 | 1 | 1 |

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 27 | 1.1 | 1.1 | 1.1 | 1.1 | 1.0 | 0.8 | 1.1 | 1.1 | 1.0 | 1.0 | 0.9 | 0.8 |

Example 28

A 1 L round bottom flask equipped with a condensor was placed under a $N_2$ atmosphere and charged with propylene imine (69.0 gram), Cardura E10P (201.0 gram) and $K_2CO_3$ (7.30 gram) and heated to 80° C., after which the mixture was stirred for 24 h at T=80° C. After filtration the excess of PI was removed in vacuo, resulting in a colorless low viscous liquid.

19.49 grams of the resulting material (2-hydroxy-3-(2-methylaziridin-1-yl)propyl neodecanoate) was charged to a reaction flask equipped with a thermometer, together with 0.02 grams of bismuth neodecanoate, 37.94 grams of a poly(ethylene glycol) monomethyl ether with an average Mn of 2000 Da and 11.07 grams of 2-methyltetrahydrofuran. The mixture was stirred with a mechanical upper stirrer under a nitrogen atmosphere and heated to 50° C. A solution of 17.55 grams of Desmodur N 3600 in 11.07 grams of 2-methyltetrahydrofuran was then added dropwise in 45 minutes to the reaction flask, a further 10 grams of 2-methyltetrahydrofuran was flushed through the feeding funnel into the reaction mixture, whereafter the mixture was heated further to 70° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain an opaque highly viscous liquid. The calculated molecular weights of the theoretical main components were 1359.96 Da (three aziridines), 3043.91 Da (two aziridines, 44 EG repeating units), 3087.94 Da (two aziridines, 45 EG repeating units) and 3131.96 Da (two aziridines, 46 EG repeating units), chemical structures are shown below.

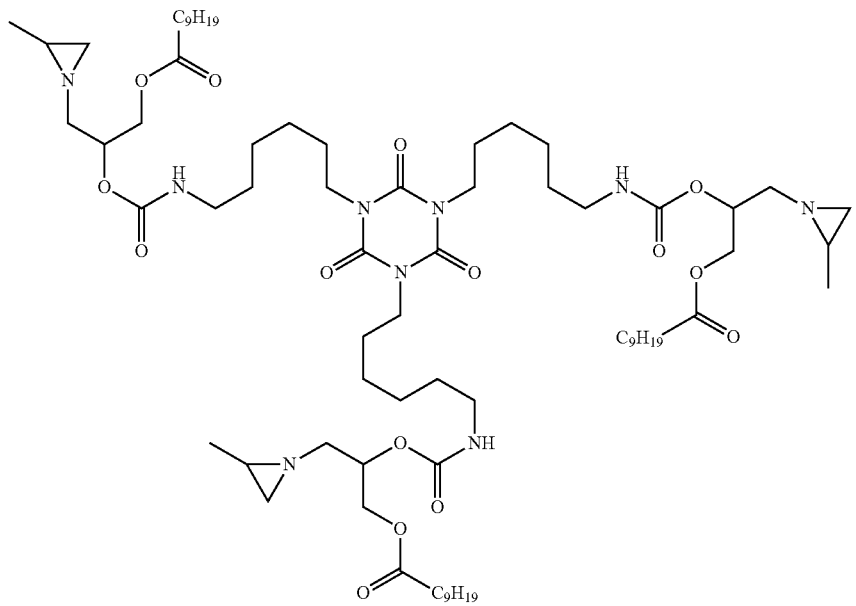

Molecular weight was confirmed by Maldi-TOF-MS:
Calcd. [M+Na+]=1382.96 Da; Obs. [M+Na+]=1382.91 Da.
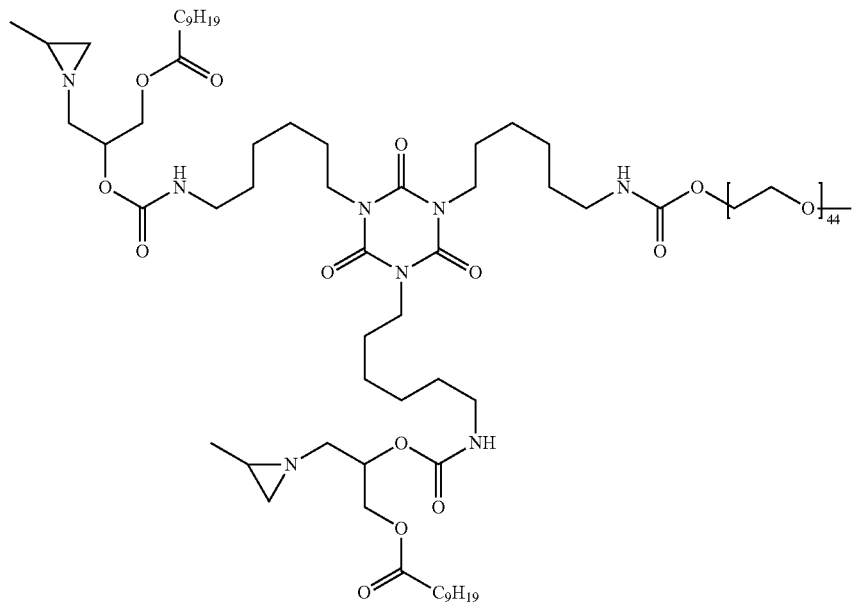
Molecular weight was confirmed by Maldi-TOF-MS:
Calcd. [M+Na+]=3066.91 Da; Obs. [M+Na+]=3066.77 Da.
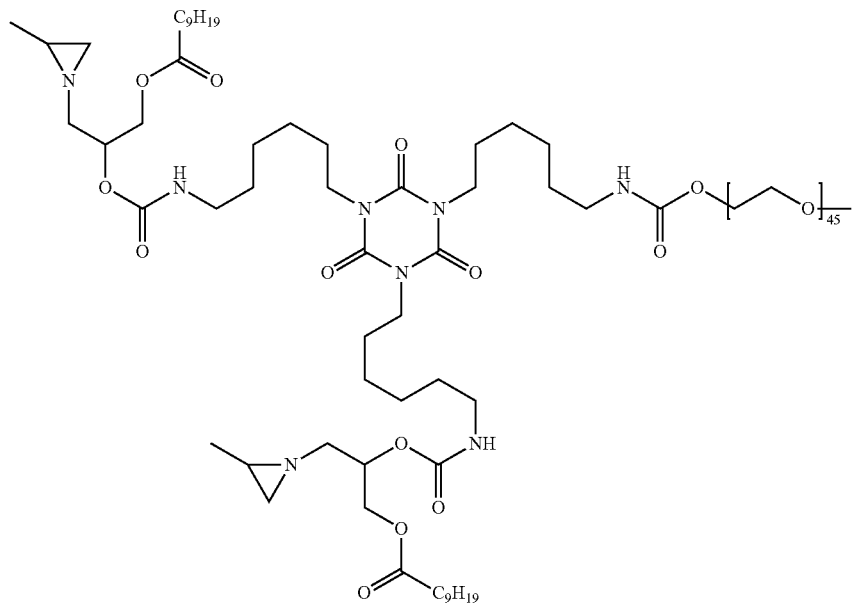

Molecular weight was confirmed by Maldi-TOF-MS: Calcd. [M+Na+]=3110.94 Da; Obs. [M+Na+]=3110.79 Da.

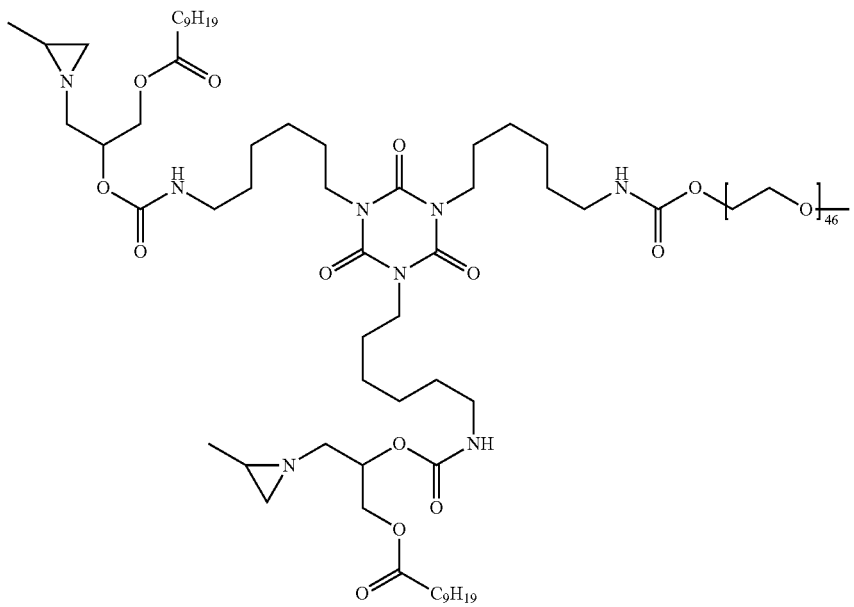

Molecular weight was confirmed by Maldi-TOF-MS: Calcd. [M+Na+]=3154.96 Da; Obs. [M+Na+]=3154.81 Da. The following components with a mass below 580 Da were determined by LC-MS and quantified:

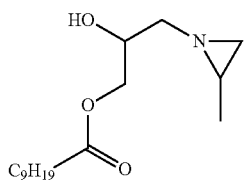

was present in the composition at 0.02 wt. %.

| | Genotoxicity test | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 28 | 1.0 | 1.1 | 1.2 | 1.4 | 1.3 | 1.2 | 1.0 | 1.1 | 1.2 | 1.0 | 1.0 | 1.0 |

Example 29

A 100 mL reactor equipped with a condensor was placed under a $N_2$ atmosphere and charged with propylene imine (2.40 gram), mPEG-Epoxide with an MW of 550 Da (10.1 gram), 2-methyltetrahydrofuran (20 mL), and $K_2CO_3$ (1.1 g) and heated to 80° C., after which the mixture was stirred for 25 h at T=80° C. After filtration the solvent and excess of PI was removed in vacuo, resulting in a dark brown viscous oil. 3.57 grams of the resulting material (1-(w-methoxy(oligo-ethyleneoxide))-3-(2-methylaziridin-1-yl)propan-2-ol with an MW of 550 Da) was charged to a reaction flask equipped with a thermometer, together with 0.02 grams of bismuth neodecanoate and 21 grams of dimethylformamide. The mixture was stirred with a mechanical upper stirrer under a nitrogen atmosphere and heated to 50° C. A solution of 1.00 grams of Desmodur N 3600 in 21 grams of dimethylformamide was then added dropwise in 15 minutes to the reaction flask, whereafter the mixture was heated further to 70° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a brownish highly viscous liquid. The calculated molecular weight of the theoretical main component was 2656.62 Da, chemical structure is shown below.

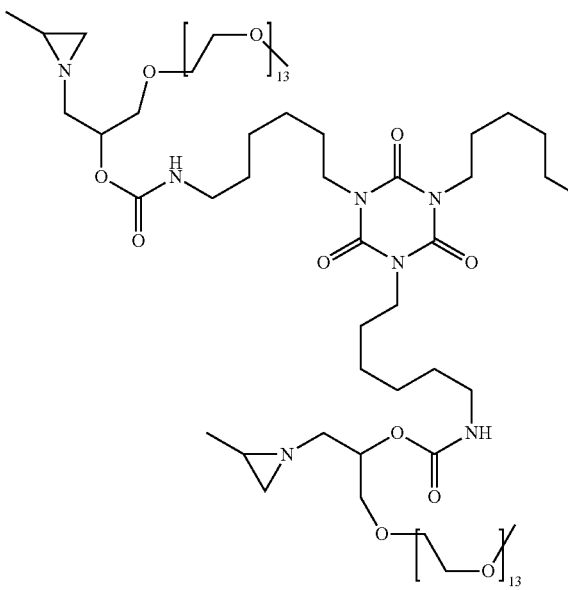

Performance of the synthesized compound as a crosslinker was assessed using spot tests on coating surfaces, based on procedures from the DIN 68861-1 standard. For these tests, 0.70 parts of the composition were mixed with 0.39 parts of Proglyde™ DMM (dipropylene glycol dimethyl ether, mixture of isomers) and incubated at 80° C. for 10 minutes under regular agitation. Subsequently, 0.73 parts of the resulting solution were added to 20 parts of NeoRez® R-1005 under continuous stirring, and the resulting mixture was further stirred for 30 minutes. Afterwards, this coating composition was filtered and applied to Leneta test cards using 100 μm wire rod applicators (Test 29-1). For reference, films were also cast from the same composition lacking a crosslinker (Test 29-2). The films were dried for 16 hours at 25° C., then annealed at 50° C. for 1 hour and further dried for 24 hours at 25° C. Subsequently, a piece of cotton wool was soaked in 1:1 EtOH:demineralizedwater and placed on the film for various timespans. After removal of the EtOH and 60 minutes recovery, the following results were obtained (a score of 1 indicates complete degradation of the film, 10 indicates no damage visible):

| Ethanol spot test | | | | |
|---|---|---|---|---|
| Sample | 30 min | 60 min | 120 min | 300 min |
| Test 29-1 | 6 | 6 | 6 | 5 |
| Test 29-2 | 1 | 1 | 1 | 1 |

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 29 | 1.1 | 1.4 | 1.4 | 1.0 | 1.1 | 1.1 | 1.1 | 1.1 | 1.1 | 1.1 | 1.1 | 1.1 |

Example 30

A 100 mL reactor equipped with a condensor was placed under a $N_2$ atmosphere and charged with propylene imine (1.30 gram), mPEG-Epoxide with an MW of 1 kDa (10.1 gram), 2-methyltetrahydrofuran (50 mL), and $K_2CO_3$ (1.1 g) and heated to 80° C., after which the mixture was stirred for 25 h at T=80° C. After filtration the solvent and excess of PI was removed in vacuo, resulting in a light brown viscous liquid.

5.61 grams of the resulting material (1-(ω-methoxy(oligoethyleneoxide))-3-(2-methylaziridin-1-yl)propan-2-ol with an MW of 1 kDa Da) was charged to a reaction flask equipped with a thermometer, together with 0.02 grams of bismuth neodecanoate and 13.79 grams of 2-methyltetrahydrofuran. The mixture was stirred with a mechanical upper stirrer under a nitrogen atmosphere and heated to 50° C. A solution of 1.00 grams of Desmodur N 3600 in 13.79 grams of 2-methyltetrahydrofuran was then added dropwise in 25 minutes to the reaction flask, a further 10 grams of 2-methyltetrahydrofuran was flushed through the feeding funnel into the reaction mixture, whereafter the mixture was heated further to 70° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a brownish highly viscous liquid. The calculated molecular weight of the theoretical main component was 4241.57 Da, chemical structure is shown below.

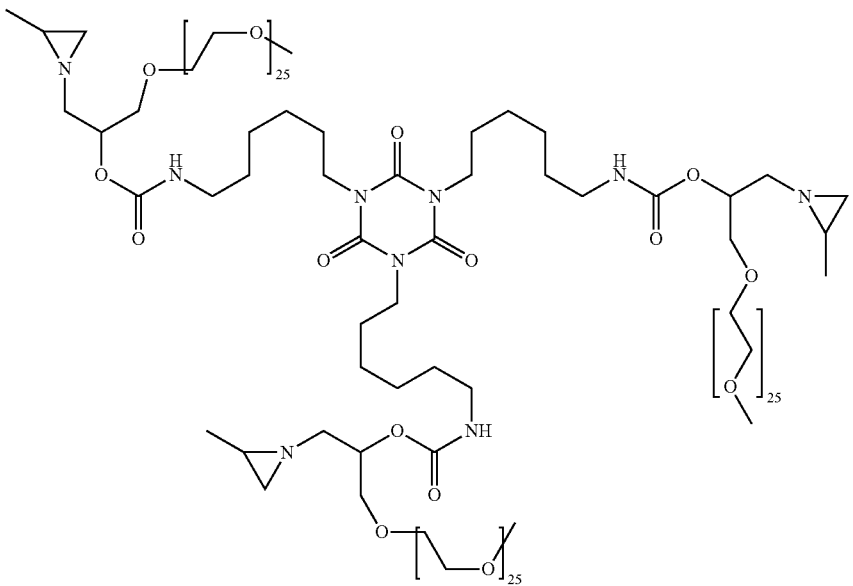

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 30 | 1.0 | 1.3 | 1.6 | 0.9 | 0.9 | 1.0 | 1.0 | 1.5 | 1.8 | 0.8 | 0.9 | 1.0 |

Example 31

A 100 mL reactor equipped with a condensor was placed under a $N_2$ atmosphere and charged with 2,2-dimethylaziridine (8.00 gram), n-butyl glycidyl ether (10.0 gram), 2-methyl tetrahydrofuran (20 mL) and $K_2CO_3$ (0.75 gram) and heated to 80° C. in 30 min, after which the mixture was stirred for 44 h h at T=80° C. After filtration the excess of PI was removed in vacuo, followed by further purification via vacuum distillation, resulting in a colorless low viscous liquid.

0.26 grams of the resulting material (1-butoxy-3-(2,2-dimethylaziridin-1-yl)propan-2-ol) was charged to a reaction flask equipped with a thermometer, together with 0.01 grams of bismuth neodecanoate and 3 grams of dimethylformamide. The mixture was stirred with a mechanical upper stirrer under a nitrogen atmosphere and heated to 50° C. A solution of 0.26 grams of Desmodur N 3600 in 3 grams of dimethylformamide was then added dropwise in 10 minutes to the reaction flask, a further 1 gram of dimethylformamide was flushed through the feeding funnel into the reaction mixture whereafter the mixture was heated further to 80° C. Samples were taken at regular intervals and the reaction progress was monitored using a Bruker Alpha FT-IR spectrometer until no change in NCO-stretch at 2200-2300 $cm^{-1}$ was observed. Subsequently, 0.03 grams of 1-butanol were added to the mixture, followed by further reaction to complete disappearance of aforementioned NCO-stretch peak. The mixture was an opaque liquid. The calculated molecular weight of the theoretical main component was 1107.79 Da, chemical structures are shown below.

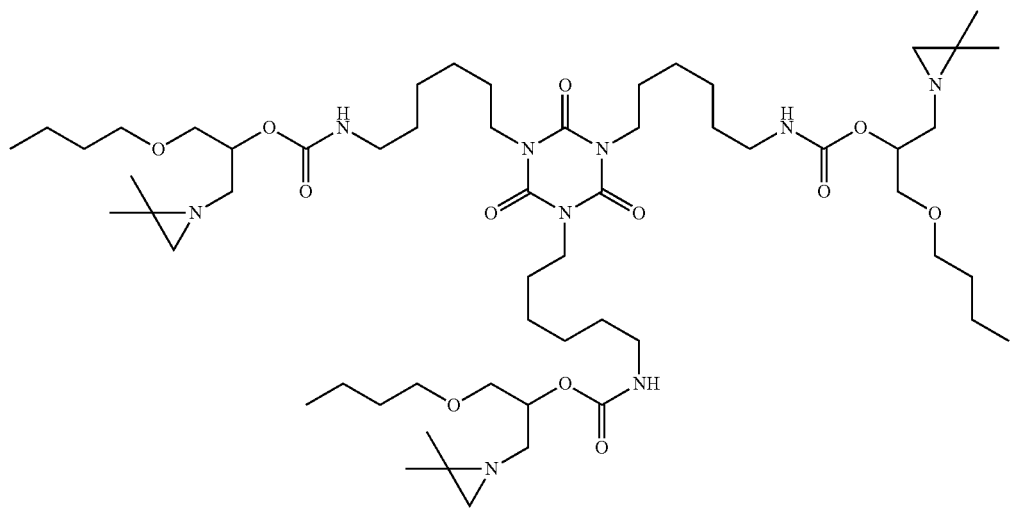 [SMILES: CCCCOCC(CN1CC1(C)C)OC(=O)NCCCCCCn1c(=O)n(CCCCCCNC(=O)OC(COCCCC)CN2CC2(C)C)c(=O)n(CCCCCCNC(=O)OC(COCCCC)CN2CC2(C)C)c1=O]
Molecular weight was confirmed by Maldi-TOF-MS: Calcd. [M+Na+]=1130.79 Da; Obs. [M+Na+]=1130.86 Da. The following components with a mass below 580 Da were determined by LC-MS and quantified:
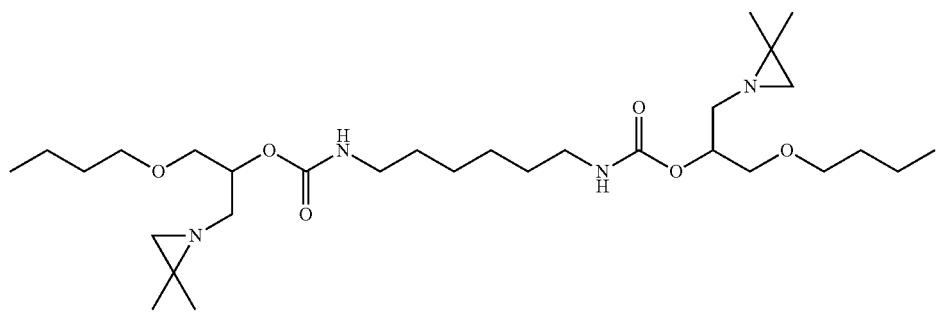 [SMILES: CCCCOCC(CN1CC1(C)C)OC(=O)NCCCCCCNC(=O)OC(COCCCC)CN1CC1(C)C]
was present in the composition at less than 0.01 wt. % and
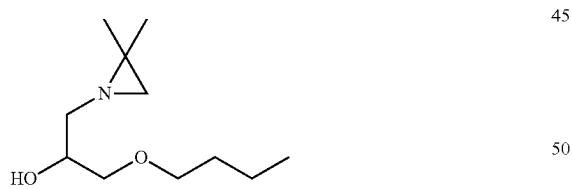
was present in the composition at 0.89 wt. %.
| | Genotoxicity test | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 31 | 1.2 | 1.2 | — | 1.2 | 1.2 | — | 1.1 | 1.1 | 1.1 | 1.2 | 1.2 | 1.3 |

Example 32

A reaction vial was charged with 2-ethylaziridine (2.50 gram), n-butyl glycidyl ether (2.00 gram) and $K_2CO_3$ (0.5 g), capped and heated to 80° C., after which the mixture was stirred for 20 h at T=80° C. After filtration the excess of PI was removed in vacuo, followed by further purification via vacuum distillation, resulting in a colorless low viscous liquid.

4.0 grams of Desmodur N 3600, 0.02 grams of bismuth neodecanoate and 8.10 grams of dimethylformamide were charged to a reaction flask equipped with a thermometer. The mixture was stirred with a mechanical upper stirrer under a nitrogen atmosphere and heated to 50° C. A solution of 4.0 grams of the product from the first step in 8.10 grams of dimethylformamide was then added dropwise in 10 minutes to the reaction flask, a further 8.10 grams of dimethylformamide was flushed through the feeding funnel into the reaction mixture, whereafter the mixture was heated further to 80° C. Samples were taken at regular intervals and the reaction progress was monitored using a Bruker Alpha FT-IR spectrometer until no change in NCO-stretch at 2200-2300 cm$^{-1}$ was observed. Subsequently, 0.13 grams of 1-butanol were added to the mixture, followed by further reaction to complete disappearance of aforementioned NCO-stretch peak. The mixture was a clear liquid. The calculated molecular weight of the theoretical main component was 1107.79 Da, chemical structures are shown below.

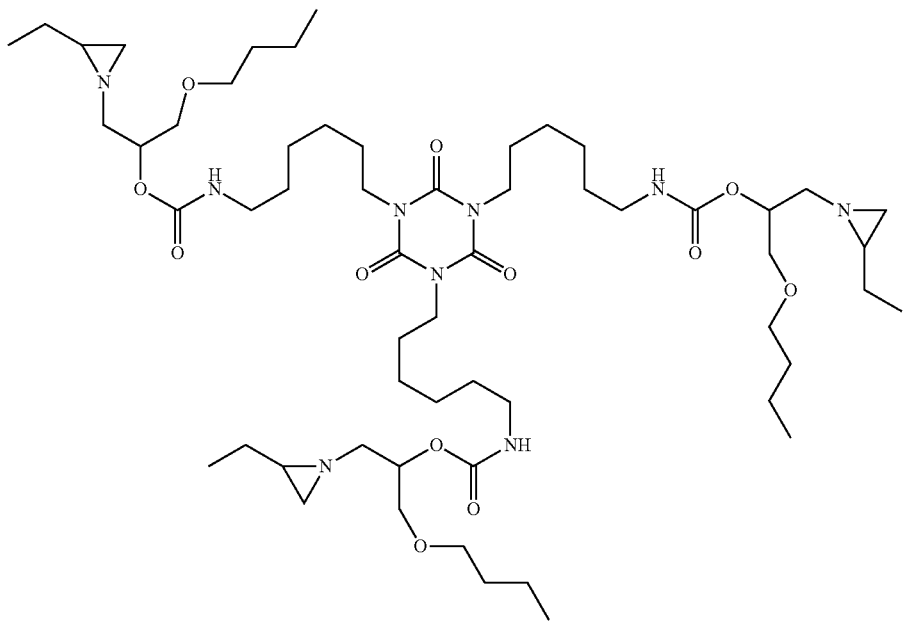 [SMILES: CCCCOCC(CN1CC1CC)OC(=O)NCCCCCCn1c(=O)n(CCCCCCNC(=O)OC(COCCCC)CN2CC2CC)c(=O)n(CCCCCCNC(=O)OC(COCCCC)CN2CC2CC)c1=O]

| Genotoxicity test | | | | | | | | | | | | |
|---|---|---|---|---|---|---|---|---|---|---|---|---|
| | Without S9 rat liver extract | | | | | | With S9 rat liver extract | | | | | |
| | Bscl 2 | | | Rtkn | | | Bscl 2 | | | Rtkn | | |
| | concentration | | | | | | | | | | | |
| | 10 | 25 | 50 | 10 | 25 | 50 | 10 | 25 | 50 | 10 | 25 | 50 |
| Ex. 32 | 1.1 | 1.2 | 1.3 | 1.0 | 1.1 | 1.1 | 1.1 | 1.1 | 1.1 | 1.0 | 1.1 | 1.1 |

The invention claimed is:

1. A multi-aziridine compound having:
a) from 2 to 6 of the following structural units (A):

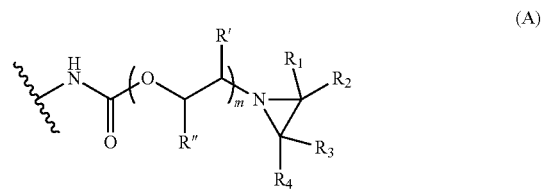

whereby $R_1$ is H;

$R_2$ and $R_4$ are independently chosen from H, a linear group containing from 1 to 8 carbon atoms and optionally containing one or more heteroatoms, a branched or cyclic group containing from 3 to 8 carbon atoms and optionally containing one or more heteroatoms, phenyl, benzyl, or pyridinyl;

$R_3$ is linear group containing from 1 to 8 carbon atoms and optionally containing one or more heteroatoms, a branched or cyclic group containing from 3 to 8 carbon atoms and optionally containing one or more heteroatoms, phenyl, benzyl, or pyridinyl;

or $R_2$ and $R_3$ (in case $R_2$ is different than H) may be part of the same cyclic group containing from 3 to 8 carbon atoms;

R'=H or an aliphatic hydrocarbon group containing from 1 to 12 carbon atoms;

R" is an aliphatic hydrocarbon group containing from 1 to 12 carbon atoms, a cycloaliphatic hydrocarbon group containing from 5 to 12 carbon atoms, an aromatic hydrocarbon group containing from 6 to 12 carbon atoms, $CH_2$—O—(C=O)—R''', $CH_2$—O—R'''', or $CH_2$—(OCR''''HCR''''H)$_n$—OR'''', whereby R''' is an aliphatic hydrocarbon group containing from 1 to 12 carbon atoms and R"" is an aliphatic hydrocarbon group containing from 1 to 12 carbon atoms or an aromatic hydrocarbon group containing from 6 to 12 carbon atoms, n being from 1 to 35, R""' independently being H or an aliphatic hydrocarbon group containing from 1 to 12 carbon atoms and R"""' being an aliphatic hydrocarbon group containing from 1 to 4 carbon atoms;

or R' and R" may be part of the same saturated cycloaliphatic hydrocarbon group containing from 5 to 8 carbon atoms;

m is an integer from 1 to 6;

b) one or more linking chains wherein each one of these linking chains links two of the structural units A and wherein the linking chain is a shortest chain of consecutive atoms that links two structural units A; and c) a molecular weight in the range from 600 Daltons to 5000 Daltons.

2. The multi-aziridine compound according to claim 1, wherein R' is H or an alkyl group containing from 1 to 4 carbon atoms.

3. The multi-aziridine compound according to claim 1, wherein R' is H or an alkyl group containing from 1 to 2 carbon atoms.

4. The multi-aziridine compound according to claim 1, wherein $R_2$ and $R_4$ are independently chosen from H or an aliphatic hydrocarbon group containing from 1 to 2 carbon atoms, and $R_3$ is an aliphatic hydrocarbon group containing from 1 to 4 carbon atoms.

5. The multi-aziridine compound according to claim 1, wherein $R_2$ is H, $R_3$ is $CH_3$ and $R_4$ is H.

6. The multi-aziridine compound according to claim 1, wherein $R_2$ is H, $R_3$ is $CH_3$ and $R_4$ is $CH_3$.

7. The multi-aziridine compound according to claim 1, wherein m is 1.

8. The multi-aziridine compound according to claim 1, wherein

R'=H or an alkyl group containing from 1 to 2 carbon atoms;

R"=an aliphatic hydrocarbon group containing from 1 to 4 carbon atoms, $CH_2$—O—(C=O)—R'", $CH_2$—O—R"", or $CH_2$—(OCR""'HCR""'H)$_n$—OR""'", whereby R'" is an alkyl group containing from 1 to 12 carbon atoms and R"" is an alkyl group containing from 1 to 12 carbon atoms, n being from 1 to 35, R""' independently being H or a methyl group and R""'" being an alkyl group containing from 1 to 4 carbon atoms;

or R' and R" may be part of the same saturated cycloaliphatic hydrocarbon group containing from 5 to 8 carbon atoms;

m is 1.

9. The multi-aziridine compound according to claim 1, wherein R' is H and R"=an alkyl group containing from 1 to 4 carbon atoms, $CH_2$—O—(C=O)—R'", $CH_2$—O—R"", or $CH_2$—(OCH$_2$CH$_2$)$_n$—OCH$_3$, whereby R'" is an alkyl group containing from 3 to 12 carbon atoms and R"" is an alkyl group containing from 1 to 12 carbon atoms.

10. The multi-aziridine compound according to claim 1, wherein the multi-aziridine compound contains 2 or 3 structural units (A).

11. The multi-aziridine compound according to claim 1, wherein the linking chains consist of from 6 to 100 atoms and the atoms of the linking chains are C, N and/or O.

12. The multi-aziridine compound according to claim 1, wherein the multi-aziridine compound has a molecular weight of from 840 to 3800 Daltons.

13. The multi-aziridine compound according to claim 1, wherein the multi-aziridine compound comprises one or more connecting groups wherein each one of these connecting groups connects two of the structural units A, whereby a connecting group is defined as an array of consecutive functionalities connecting two structural units A and whereby the connecting groups consist of at least one functionality selected from:

aliphatic hydrocarbon functionality, cycloaliphatic hydrocarbon functionality, aromatic hydrocarbon functionality, isocyanurate functionality, iminooxadiazindione functionality, ether functionality, ester functionality, amide functionality, carbonate functionality, urethane functionality, urea functionality, biuret functionality, allophanate functionality, uretdione functionality and any combination thereof.

14. The multi-aziridine compound according to claim 12, wherein the connecting groups of the multi-aziridine compound consist of at least one functionality selected from:

aliphatic hydrocarbon functionality, cycloaliphatic hydrocarbon functionality, aromatic hydrocarbon functionality, isocyanurate functionality, iminooxadiazindione functionality, urethane functionality, urea functionality, biuret functionality and any combination thereof.

15. The multi-aziridine compound according to claim 13, wherein the connecting groups consist of at least one aliphatic hydrocarbon functionality and/or at least one cycloaliphatic hydrocarbon functionality and optionally at least one aromatic hydrocarbon functionality and optionally an isocyanurate functionality or an iminooxadiazindione functionality.

16. The multi-aziridine compound according to claim 13, wherein the connecting groups consist of at least one aliphatic hydrocarbon functionality and/or at least one cycloaliphatic hydrocarbon functionality and an isocyanurate functionality or an iminooxadiazindione functionality.

17. The multi-aziridine compound according to claim 1, wherein the multi-aziridine compound is according to the following structural formula:

$$Z\text{—}[D_i]_q$$

in which Z is a molecular residue obtained by removing isocyanate reactive groups XH of a molecule;

q is an integer from 2 to 6;

i is an integer from 1 to q;

$D_i$ independently have the following structural formula

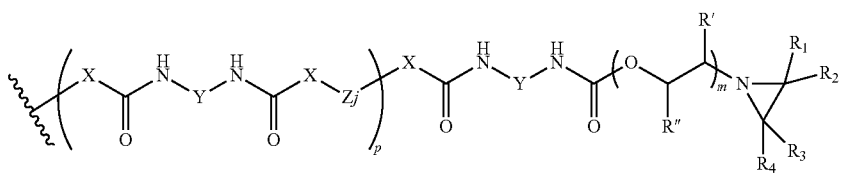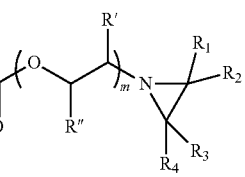

in which X is NR$_{11}$, S or O, whereby R$_{11}$ is H or an alkyl group with 1 to 4 carbon atoms;

Y is an aromatic hydrocarbon group, an aliphatic hydrocarbon group, a cycloaliphatic hydrocarbon group or a combination thereof;

j is an integer from 1 to p;

p is an integer from 0 to 10, m, R', R'', R$_1$, R$_2$, R$_3$ and R$_4$ are as previously defined.

18. The multi-aziridine compound according to claim 17, wherein the molecule from which isocyanate reactive group are removed to obtain Z is a diol, a triol, a polyether with terminal isocyanate reactive groups, a polyamide with terminal isocyanate reactive groups, a polycarbonate with terminal isocyanate reactive groups, or a polysiloxane with terminal isocyanate reactive groups which groups are linked to the siloxane via at least one carbon atom, p is o and m is 1.

19. The multi-aziridine compound according to claim 1, wherein the multi-aziridine compound contains at least 5 wt. % and less than 20 wt. % of urethane bonds.

20. The multi-aziridine compound according to claim 1, wherein the multi-aziridine compound is obtained by reacting at least a polyisocyanate and a compound B with the following structural formula:

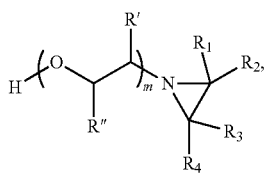

whereby the molar ratio of compound B to polyisocyanate is from 2 to 6, more preferably from 2 to 4 and most preferably from 2 to 3, and whereby m, R', R'', R$_1$, R$_2$, R$_3$ and R$_4$ are as previously defined.

21. The multi-aziridine compound according to claim 20, wherein the polyisocyanate is a polyisocyanate with aliphatic reactivity.

22. The multi-aziridine compound according to claim 20, wherein compound B is obtained by reacting at least a non-OH functional monoepoxide compound with an aziridine with the following structural formula:

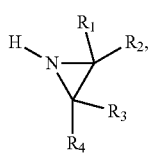

whereby R$_1$, R$_2$, R$_3$ and R$_4$ are as previously defined.

23. The multi-aziridine compound according to claim 22, wherein the non-OH functional monoepoxide compound is selected from the group consisting of propylene oxide, 2-ethyl oxirane, n-butylglycidylether, 2-ethylhexylglycidylether, glycidyl neodecanoate and any mixture thereof.

24. The multi-aziridine compound according to claim 1, wherein the multi-aziridine compound contains polyoxyethylene (—O—CH2-CH2-)$_x$ groups or polyoxypropylene (—O—CHCH3-CH2-)$_x$ groups or polytetrahydrofurane (—O—CH2-CH2-CH2-CH2)$_x$ groups in an amount of at least 0.1 wt. % and in an amount of less than 45 wt. %, relative to the multi-aziridine compound.

25. A crosslinker composition comprising at least one multi-aziridine compound according to claim 1 and further comprising at least one additional component.

26. The crosslinker composition according to claim 25, wherein the molecular weight of the multi-aziridine compounds present in the crosslinker composition is in the range from 600 Daltons to 5000 Daltons.

27. The crosslinker composition according to claim 25, wherein the amount of aziridine functional molecules having a molecular weight lower than 580 Daltons is lower than 5 wt. %, relative to the total weight of the crosslinker composition, whereby the molecular weight is determined using LC-MS as described in the description.

28. The crosslinker composition according to claim 25, wherein the crosslinker composition contains less than 5 wt. % of water.

29. A method for crosslinking a carboxylic acid functional polymer dissolved and/or dispersed in an aqueous medium comprising providing the multi-aziridine compound according to claim 1.

30. A two-component system comprising a first component and a second component each of which is separate and distinct from each other and wherein the first component comprises a carboxylic acid functional polymer dissolved and/or dispersed in an aqueous medium and the second component comprises a multi-aziridine compound according to claim 1.

31. A substrate having a coating obtained by (i) applying a coating composition obtained by mixing the first and second component of the two-component system according to claim 30 to a substrate and (ii) drying the coating composition by evaporation of volatiles.

32. A method for crosslinking a carboxylic acid functional polymer dissolved and/or dispersed in an aqueous medium comprising providing the crosslinker composition according to claim 25.

33. The multi-aziridine compound according to claim 2, wherein m is 1.

34. The multi-aziridine compound according to claim 3, wherein m is 1.

35. The multi-aziridine compound according to claim 4, wherein m is 1.

36. The multi-aziridine compound according to claim 5, wherein m is 1.

37. The multi-aziridine compound according to claim 6, wherein m is 1.

38. The multi-aziridine compound according to claim 9, wherein m is 1.

39. The multi-aziridine compound according to claim 10, wherein m is 1.

40. The multi-aziridine compound according to claim 11, wherein m is 1.

41. The multi-aziridine compound according to claim 12, wherein m is 1.

42. The multi-aziridine compound according to claim 13, wherein m is 1.

43. The multi-aziridine compound according to claim 7, wherein R' is H and R"=an alkyl group containing from 1 to 4 carbon atoms, $CH_2$—O—(C=O)—R''', $CH_2$—O—R'''', or $CH_2$—$(OCH_2CH_2)_n$—$OCH_3$, whereby R''' is an alkyl group containing from 3 to 12 carbon atoms and R'''' is an alkyl group containing from 1 to 12 carbon atoms, wherein the multi-aziridine compound contains 2 or 3 structural units (A), wherein the multi-aziridine compound has a molecular weight of from 840 to 3800 Daltons.

44. The multi-aziridine compound according to claim 17, wherein m is 1.

45. The multi-aziridine compound according to claim 19, wherein m is 1.

46. The multi-aziridine compound according to claim 20, wherein m is 1.

47. The multi-aziridine compound according to claim 21, wherein m is 1.

48. The multi-aziridine compound according to claim 22, wherein m is 1.

49. The multi-aziridine compound according to claim 23, wherein m is 1.

50. The multi-aziridine compound according to claim 24, wherein m is 1.

\* \* \* \* \*